(12) United States Patent
Glimcher et al.

(10) Patent No.: US 10,655,130 B2
(45) Date of Patent: May 19, 2020

(54) MODULATION OF BREAST CANCER GROWTH BY MODULATION OF XBP1 ACTIVITY

(71) Applicant: Cornell University, Ithaca, NY (US)

(72) Inventors: Laurie H. Glimcher, New York, NY (US); Xi Chen, Malden, MA (US)

(73) Assignee: Cornell University, Ithaca, NY (US)

( * ) Notice: Subject to any disclaimer, the term of this patent is extended or adjusted under 35 U.S.C. 154(b) by 261 days.

(21) Appl. No.: 15/441,103

(22) Filed: Feb. 23, 2017

(65) Prior Publication Data

US 2017/0240903 A1 Aug. 24, 2017

Related U.S. Application Data

(62) Division of application No. 14/383,687, filed as application No. PCT/US2013/030251 on Mar. 11, 2013, now abandoned.

(60) Provisional application No. 61/609,130, filed on Mar. 9, 2012.

(51) Int. Cl.
| | | |
|---|---|---|
| *C12N 15/113* | (2010.01) | |
| *A61K 31/7088* | (2006.01) | |
| *A61K 45/06* | (2006.01) | |
| *C12Q 1/6886* | (2018.01) | |
| *G01N 33/50* | (2006.01) | |
| *G01N 33/574* | (2006.01) | |

(52) U.S. Cl.
CPC ...... *C12N 15/1137* (2013.01); *A61K 31/7088* (2013.01); *A61K 45/06* (2013.01); *C12N 15/113* (2013.01); *C12N 15/1135* (2013.01); *C12Q 1/6886* (2013.01); *C12Y 207/11001* (2013.01); *G01N 33/5011* (2013.01); *G01N 33/57415* (2013.01); *C12N 2310/11* (2013.01); *C12N 2310/14* (2013.01); *C12N 2310/531* (2013.01); *C12N 2320/30* (2013.01); *C12N 2320/31* (2013.01); *C12Q 2600/118* (2013.01); *C12Q 2600/136* (2013.01); *G01N 2500/04* (2013.01); *G01N 2800/52* (2013.01)

(58) Field of Classification Search
CPC .. A61K 31/7088; A61K 45/06; C12N 15/113; C12N 15/1135; C12N 15/1137; C12N 2310/11; C12N 2310/14; C12N 2310/531; C12N 2320/30; C12N 2320/31; C12Q 1/6886; C12Q 2600/118; C12Q 2600/136; C12Y 207/11001; G01N 2500/04; G01N 2800/52; G01N 33/5011; G01N 33/57415
See application file for complete search history.

(56) References Cited

U.S. PATENT DOCUMENTS

| | | |
|---|---|---|
| 5,908,762 A | 6/1999 | Ono et al. |
| 5,945,307 A | 8/1999 | Glucksmann et al. |
| 6,037,148 A | 3/2000 | Khodadoust |
| 6,075,181 A | 6/2000 | Kucherlapati et al. |
| 6,410,516 B1 | 6/2002 | Baltimore et al. |
| 6,413,735 B1 | 7/2002 | Lau |
| 6,632,608 B2 | 10/2003 | Glimcher et al. |
| 6,632,641 B1 | 10/2003 | Brennan et al. |
| 7,220,539 B1 | 5/2007 | Du et al. |
| 7,358,415 B2 | 4/2008 | Glimcher et al. |
| 8,227,184 B2 | 7/2012 | Glimcher et al. |
| 8,940,479 B2 | 1/2015 | Lee et al. |
| 2002/0059652 A1 | 5/2002 | Glimcher et al. |
| 2003/0096762 A1 | 5/2003 | Fischer et al. |
| 2003/0224428 A1 | 12/2003 | Ron et al. |
| 2004/0077020 A1 | 4/2004 | Mannick et al. |
| 2004/0110236 A1 | 6/2004 | Glimcher et al. |
| 2004/0170622 A1 | 9/2004 | Glimcher et al. |
| 2004/0197272 A1 | 10/2004 | Fischer et al. |
| 2005/0059052 A1 | 3/2005 | Kaufman et al. |
| 2005/0059652 A1 | 3/2005 | Hamann et al. |
| 2005/0250182 A1 | 11/2005 | Kaufman et al. |
| 2006/0057104 A1 | 3/2006 | Cheng et al. |
| 2006/0063187 A1 | 3/2006 | Hotamisligil et al. |

(Continued)

FOREIGN PATENT DOCUMENTS

| | | |
|---|---|---|
| EP | 0857780 A1 | 8/1998 |
| EP | 1669067 A2 | 6/2006 |

(Continued)

OTHER PUBLICATIONS

A printout "Breast Cancer Stages" retrieved from https://www.breastcancer.org/symptonns/diagnosis/staging?gclid=EAlalQobChMlhcqitOvF4QIVwkSGCh0zWwnKEAAYAiAAEgKklvD_BwE on Apr. 10, 2019.*

Li et al., "microPNA-34a and microPNA-34c promote the activation of human hepatic stellate cells by targeting peroxisome proliferator-activated receptor γ," Mol. Med. Rep., Feb. 2015, vol. 11, No. 2, pp. 1017-1024; Epub Nov. 3, 2014.*

(Continued)

*Primary Examiner* — Galina M. Yakovleva
(74) *Attorney, Agent, or Firm* — Schwegman Lundberg & Woessner, P.A.

(57) ABSTRACT

Described herein is a previously unknown function of XBP1 in triple-negative breast cancer (TNBC). It is shown that XBP1 is preferentially spliced and activated in TNBC, and that deletion of XBP1 significantly blocks triple negative breast tumor growth. Strikingly, XBP1 is required for the self-renewal of breast tumor initiating cells (TICs). Genome-wide mapping of the XBP1 transcriptional regulatory network identified a fundamental role for XBP1 in regulating the response to hypoxia via the transcription factor hypoxia-inducible factor 1α (HIF1α). Importantly, activation of this pathway appears to carry prognostic implications, as expression of the XBP1-dependent signature is associated with shorter survival times in human TNBC.

6 Claims, 27 Drawing Sheets

Specification includes a Sequence Listing.

(56) References Cited

U.S. PATENT DOCUMENTS

| | | | |
|---|---|---|---|
| 2006/0073213 | A1 | 4/2006 | Hotamisligil et al. |
| 2006/0148739 | A1 | 7/2006 | Kotani et al. |
| 2007/0141074 | A1 | 6/2007 | Schubert |
| 2008/0241114 | A1 | 10/2008 | Glimcher et al. |
| 2009/0186893 | A1 | 7/2009 | Patterson et al. |
| 2009/0232738 | A1 | 9/2009 | Glimcher et al. |
| 2009/0275608 | A1* | 11/2009 | Ossovskaya ......... C12Q 1/6886 514/307 |
| 2009/0275638 | A1* | 11/2009 | Fitzgerald ............ C12N 15/113 514/44 A |
| 2009/0291857 | A1 | 11/2009 | Koong et al. |
| 2010/0075894 | A1 | 3/2010 | Hotamisligil et al. |
| 2011/0052669 | A1 | 3/2011 | Lee et al. |
| 2011/0142799 | A1 | 6/2011 | Glimcher et al. |
| 2012/0141539 | A1 | 6/2012 | Glimcher |
| 2012/0270877 | A1 | 10/2012 | Zeng et al. |
| 2012/0322814 | A1 | 12/2012 | Korennykh et al. |
| 2014/0030294 | A1 | 1/2014 | Glimcher |
| 2014/0170622 | A1 | 6/2014 | Pastrick et al. |
| 2015/0018406 | A1 | 1/2015 | Glimcher et al. |

FOREIGN PATENT DOCUMENTS

| | | | |
|---|---|---|---|
| WO | WO-97/39721 | A2 | 10/1997 |
| WO | WO-9918953 | A1 | 4/1999 |
| WO | WO-01/49717 | A2 | 7/2001 |
| WO | WO-01/72783 | A2 | 10/2001 |
| WO | WO-2004/020610 | A2 | 3/2004 |
| WO | WO-2004/037373 | A2 | 5/2004 |
| WO | WO-2005/034737 | A2 | 4/2005 |
| WO | WO-2006/031930 | A2 | 3/2006 |
| WO | WO-2006/031931 | A2 | 3/2006 |
| WO | WO-2007/041282 | A2 | 4/2007 |
| WO | WO-2007/053747 | A2 | 5/2007 |
| WO | WO-2007/101224 | A2 | 9/2007 |
| WO | WO-2008/039445 | A2 | 4/2008 |
| WO | WO-2008/141129 | A1 | 11/2008 |
| WO | WO-2008/143876 | A2 | 11/2008 |
| WO | WO-2009/091815 | A2 | 7/2009 |
| WO | WO-2009/129465 | A2 | 10/2009 |
| WO | WO-2010/008860 | A1 | 1/2010 |
| WO | WO-2010/014905 | A2 | 2/2010 |
| WO | WO-2010/031056 | A2 | 3/2010 |
| WO | WO-2010/088498 | A1 | 8/2010 |
| WO | WO-2010/141619 | A1 | 12/2010 |
| WO | WO-2010/151827 | A1 | 12/2010 |
| WO | WO-2011/022316 | A1 | 2/2011 |
| WO | WO-2012/109238 | A2 | 8/2012 |
| WO | WO-2012/138715 | A2 | 10/2012 |
| WO | WO-2013/134774 | A1 | 9/2013 |
| WO | WO-2015/048331 | A1 | 4/2015 |

OTHER PUBLICATIONS

Rao et al., "siRNA vs. shRNA: Similarities and differences," Advanced Drug Delivery Reviews, 2009, vol. 61, issue 9, pp. 746-759.*

Boudreau et al., "Minimizing variables among hairpin-based RNAi vectors reveals the potency of shRNAs," RNA, 2008, vol. 14, No. 9 pp. 1834-1844.*

"U.S. Appl. No. 14/383,687, Non-Final Office Action dated Sep. 23, 2016", 14 pgs.

"U.S. Appl. No. 14/383,687, Notice of Non-Compliant Amendment dated Oct. 21, 2014", 2 pgs.

"U.S. Appl. No. 14/383,687, Preliminary Amendment filed Dec. 19, 2014", 6 pgs.

"U.S. Appl. No. 14/383,687, Response filed Aug. 8, 2016 to Restriction Requirement dated Feb. 8, 2016", 7 pgs.

"U.S. Appl. No. 14/383,687, Restriction Requirement dated Feb. 8, 2016", 12 pgs.

"GenBank Accession No. BAA82600 for hepatocarcinogenesis-related transcription factor (HTF) [Rattus norvegicus]", (Apr. 14, 2000), 2 pgs.

"GenBank Accession No. CAA39149 for TREB protein [Homo sapiens].", (Apr. 18, 2005), 2 pgs.

"GenBank Accession No. P17861 for X Box Binding Protein-1 (XBP-1) (TREB5 Protein)", (Apr. 24, 1993).

"International Application Serial No. PCT/US2012/024140, International Preliminary Report on Patentability dated Aug. 22, 2013", 7 pgs.

"International Application Serial No. PCT/US2012/024140, International Search Report dated Aug. 17, 2012", 4 pgs.

"International Application Serial No. PCT/US2012/024140, Written Opinion dated Aug. 17, 2012", 5 pgs.

"International Application Serial No. PCT/US2013/030251, International Preliminary Report on Patentability dated Sep. 18, 2014", 8 pgs.

"International Application Serial No. PCT/US2013/030251, International Search Report dated Jun. 26, 2013", 7 pgs.

"International Application Serial No. PCT/US2013/030251, Written Opinion dated Jun. 26, 2013", 7 pgs.

"Thermo Scientific Pierce Protein Interaction Technical Handbook", Version 2, (2010), 73 pgs.

"Wikipedia, Autophagy", [Online] Retrieved from the Internet: <http://en.wikipedia.org/wiki/Autophagy>, (2012), 6 pgs.

"Wikipedia, Statin", [Online] retrieved from the internet: <http://en.wikipedia.org/wiki/Statin>, (2008), 8 pgs.

Abcam, "IRE1 antibody (ab45973)", [Online] Retrieved from the Internet: <http://www.abcam.com/IRE1-antibody-ab45973.html>, (2011), 4 pgs.

Abcam®, "XBP1 antibody (ab37152)", [Online] Retrieved from the Internet: :<http://www.abcam.com/XBP1-antibody-ab37152.html>, (2011), 4 pgs.

Acosta-Alvear, D., et al., "XBP1 controls diverse cell type- and condition specific-transcriptional regulatory networks", Molecular Cell, vol. 27, (2007), 53-66.

Acsadi, G., et al., "Human Dystrophin Expression in mdx Mice Aller Intramuscular Injection of DNA Constructs", Nature, 333, (1991), 815-818.

Aghajanian, C., et al., "A phase I trial of the novel proteasome inhibitor PS341 in advanced solid tumor malignancies", Clin Cancer Res, vol. 8, (2002), 2505-2511.

Ahern, H, "Biochemical Reagent kits offer scientists good return on investment", The Scientist, vol. 9(15), (1995), 20 pgs.

Akira, et al., "NF-IL6 and NF-Kappa B in Cytokine Gene Regulation", Adv Immunol., 65:, (1997), 1-46.

Alton, et al., "Nucleotide Sequence Analysis of the Chloramphenicol Resistance Transposon Tn9", Nature 282, (1979), 864-869.

Amit, I, et al., "Unbiased Reconstruction of a Mammalian Transcriptional Network Mediating Pathogen Responses", Science, vol. 326, (2009), 257-263.

Aragon, T, et al., "Messenger RNA targeting to endoplasmic reticulum stress signalling sites", Nature, 457, (2009), 736-740.

Araki, E, et al., "Endoplasmic reticulum stress and diabetes mellitus", Internal Medicine, 42(1), (2003), 7-14.

Arpin, et al., "Generation of Memory B Cells and Plasma Cells In Vitro", Science 268, (1995), 720.

Askari, et al., "Molecular Medicine Antisense-Oligonucleotide Therapy", N. Engl. J. Med., 334, (1996), 316-311.

Atkin, J, et al., "Endoplasmic reticulum stress and induction of the unfolded protein response in human sporadic amyotrophic lateral sclerosis", Neurobiology of Disease, vol. 30, (2008), 400-407.

Atkin, J, et al., "Induction of the Unfolded Protein Response in Familial Amyotrophic Lateral Sclerosis and Association of Protein-disulfide Isomerase with Superoxide Dismutase 1", The Journal of Biological Chemistry, vol. 281 (40), (2006), 30152-30165.

Atkinson, et al., "The NOD mouse model of type 1 diabetes: As good as it gets?", Nature Medicine, 5(6), (1999), 601-604.

Attisano, et al., "Signal Transduction by the TGF-β Superfamily", Science 296, (2002), 1646-1647.

Auf, G, et al., "Inositol-requiring enzyme 1 is a key regulator of angiogenesis and invasion in malignant glioma", Proc. Natl. Acad. Sci. USA, 107(35), (2010), 15553-15558.

Bagchi, Aranya, et al., "MyD88-Dependent and MyD88-Independent Pathways in Synergy, Priming, and Tolerance between TLR Agonists", J. Immun., 178, (2007), 1164-1171.

(56) References Cited

OTHER PUBLICATIONS

Bai, et al., "A Mouse Model to Test the In Vivo Efficacy of Chemical Chaperones", J. of Pharm. and Toxicol. Methods, 40(1), (1998), 39-45.
Baldwin, et al., "Cloning of the Luciferase Structural Genes From Vibrio Harveyi and Expression of Bioluminescence in *Escherichia coli*", Biochemistry 23, (1984), 3663-366.
Bancroft, A J, et al., "Cytokine Production in BALB/c Mice Immunized with Radiation Attenuated Third Stage Larvae of the Filarial Nematode, Brigia pahangi", J. Immunol., 150(4), (1993), 1395-1402.
Banerji, et al., "A Lymphocyte-Specific Cellular Enhancer Is Located Downstream of The Joining Region in Immunoglobulin Heavy Chain Genes", Cell 33, (1983), 729-740.
Bantignies, et al., "Genetic characterization of transactivation of the human T-cell leukemia virus type 1 promoter: Binding of Tax to Tax-responsive element 1 is mediated by the cyclic AMP responsive members of the CREB/ATF family of transcription factors", Mol Cell Biol.,16(5), (1996), 2174-2182.
Barouch, D H, et al., "Immunogenicity of recombinant adenovirus serotype 35 vaccine in the presence of pre-existing anti-Ad5 immunity", J Immunol., vol. 172, (2004), 6290-6297.
Barr, R. K., et al., "Identification of the Critical Features of a Small Peptide Inhibitor of JNK Activity", J. Biol. Chem., 277, (2002), 10987-10997.
Barski, A, et al., "High-resolution profiling of histone methylations in the human genome", Cell, vol. 129, (2007), 823-837.
Bartel, et al., "Elimination of False Positives That Arise in Using the Two-Hybrid Systems", Biotechniques, 14, (1993), 920-924.
Bartel, David P., et al., "Isolation of New Ribozymes from a Large Pool of Random Sequence", Science, 261(5127), (1993), 1411-1418.
Barthel, et al., "RNA Interference-based Strategies for Metabolic Syndrome Treatment", Horm. Metab. Res., 37, (2005), 59-62.
Beerli, et al., "Autocrine Inhibition of The Epidermal Growth Factor Receptor by Intracellular Expression of a Single-Chain Antibody", Biochem. Biophys. Res. Commun. 204, (1994), 666-672.
Beg, Amer A., et al., "Embryonic lethality and liver degeneration in mice lacking the RelA component of NF-kB", Nature, 376(6536), (1995), 167-170.
Bennet, et al., "Antisense Therapy for Angioplasty Restenosis. Some Critical Considerations", Circulation, 92, (1995), 1981-1993.
Bennet, et al., "JNK: A New Therapeutic Target for Diabetes", Current Opinion in Pharmacology, 3, (2003), 420-425.
Berkner, K., "Development of adenovirus vectors for the expression of heterologous genes", BioTechniques, 6(7), (Jul.-Aug. 1988), 616-629.
Bertolotti, A, et al., "Dynamic interaction of BiP and ER stress transducers in the unfolded-protein response", Nat Cell Biol., 2, (2000), 326-332.
Biocca, et al., "Intracellular Immunization with Cytosolic Recombinant Antibodies", Biotechnology 12, (1994), 396-399.
Blackman, et al., "A Model System for Peptide Hormone Action in Differentiation: Interleukin 2 Induces a B Lymphoma to Transcribe the J Chain Gene", Cell 47, (1986), 609-617.
Blumenthal, A, et al., "Common and unique gene expression signatures of human macrophages in response to four strains of *Mycobacterium avium* that differ in their growth and persistence characteristics", Infect Immun., 73, (2005), 3330-3341.
Boeglin, et al., "Soluble CD40L and TLR Agonist synergize Murine B Cell Proliferation", Eur. J. Immunol., (2009), S55-S279.
Boes, et al., "Enhanced B-1 Cell Development, But Impaired IgG Antibody Responses in Mice Deficient in Secreted IgM", J Immunol., 160, (1998), 4776-4787.
Bogoyevitch, et al., "Targeting the JNK MAPK Cascade for Inhibition: Basic Science and Therapeutic Potential", Biochimica et Biophysica Acta, 1697, (2004), 89-101.
Boldrick, J C, et al., "Stereotyped and specific gene expression programs in human innate immune responses to bacteria", Proc Natl Acad Sci USA, vol. 99, (2002), 972-977.

Bonapace, et al., "Chemical Chaperones protect from the effect of apoptosis-inducing mutation in carbonic anhydrase IV identified in retinitis pigmentosa 17", Proc. Natl. Acad. Sci. USA, 101(33), (2004), 12300-12305.
Boobbyer, et al., "New Hydrogen-Bond Potentials for Use in Determining Energetically Favorable Binding Sites on Molecules of Known Structure", J Med. Chern. 32, (1989), 1083.
Bossy-Weyzel, et al., "Assay for Cytochrome c Release From Mitochondria During Apoptosis", Methods in Enzymol., 322, (2000), 235-242.
Brauweiler, et al., "A molecular mechanism for human T-cell leukemia virus latency and Tax transactivation", J Biol Chem., 270(21), (1994), 12814-12822.
Brown, et al., "Structural Characterization of Human Melanoma-Associated Antigen p97 With Monoclonal Antibodies", J Immunol., 127, (1981), 539-546.
Burdin, et al., "Endogenous IL-6 and IL-10 Contribute to the Differentiation of CD40-Activated Human B", J Immunol., 154, (1995), 2533-2544.
Bush, et al., "Proteasome inhibition leads to a heat-shock response, induction of endoplasmic reticulum chaperones, and thermotolerance", J Biol Chem., vol. 272(141),, (1997), 9086-9092.
Calfon, m. et al., "IRE1 couples endoplasmic reticulum load to secretory capacity by processing the XBP-1 mRNA", (2002), 92-96.
Campanero, M, et al., "Regulation of E2F through ubiquitin-proteasome-dependent degradation: Stabilization by the pRB tumor suppressor protein", Proc. Natl. Acad. Sci. USA, vol. 94, (1997), 2221-2226.
Chen, et al., "Intracellular Antibodies as a New Class of Therapeutic Molecules for Gene Therapy", Human Gene Therapy, 5, (1994), 595-601.
Chen, B P, et al., "Analysis of ATF3, a transcription factor induced by physiological stresses and modulated by Jadd153/Chop10", Mol. Cell Biol., vol. 16, (1996), 1157-1168.
Chen, C, et al., "In Vitro Induction of T Cell Anergy by Blocking B7 and Early T Cell Costimulatory Molecule ETC-1/B7-2", Immunity, vol. 1, (1994), 147-154.
Chen, H, et al., "Regulation and Activities of alpha-Fetoprotein", Critical Reviews in Eukaryotic Gene Expression 7(1&2), (1997), 11-41.
Chen, L, et al., "HIV protease inhibitor lopinavir-induced TNF-alpha and IL-6 expression is coupled to the unfolded protein response and ERK signaling pathways in macrophages", Biochem Pharmacol., vol. 78, (2009), 70-77.
Chen, X, et al., "Integration of external signaling pathways with the core transcriptional network in embryonic stem cells", Cell, vol. 133, (2008), 1106-1117.
Chevalier, et al., "Interaction of murine BiP/GRP78 with the Dna homologue MTJ1", J Biol Chem., vol. 275(26), (2000), 19620-1962.
Choe, et al., "IL-10 Interrupts Memory B Cell Expansion in the Germinal Center by Inducing Differentiation Into Plasma Cells", Eur J Immunol., 28, (1998), 508-515.
Chow, et al., "Anti-HIV drugs for cancer therapeutics: back to the future?", Lancet Oncol., (2009), 61-71.
Clackson, T., et al., "Making Antibody Fragments Using Phage Display Libraries", Nature, 352(6336), (1991), 624-628.
Clerici, Mario, et al., "A TH1-TH2 switch is a critical step in the etiology of HIV infection", Immunology Today, 14(3), (1993), 107-111.
Cohen, et al., "Emerging Technologies for Sequencing Antisense Oligonucleotides: Capillary Electrophoresis and Mass Spectrometry", Adv. Chromatgr. 36, (1996), 127-162.
Cotton, "Current Methods of Mutation Detection", Mulot Res., 285, (1992), 125-144.
Cottrell, et al., "Silence of the Strands: RNA Interference in Eukaryotic Pathogens", Trends Microbioll., (2003), 37-43.
Cox, J, et al., "Transcriptional induction of genes encoding endoplasmic reticulum resident proteins requires a transmembrane protein kinase", Cell, 73, (1993), 1197-1206.
Cressman, et al., "Liver Failure and Defective Hepatocyte Regeneration in Interleukin-6-Deficient Mice", Science, 274, (1996), 1379-1383.

(56) References Cited

OTHER PUBLICATIONS

Dallman, M J, "Cytokines and transplantation: Th1/Th2 regulation of the immune response to solid organ transplants in the adult", Curr. Opin. Immunol. vol. 7,, (1995), 632-638.

Darzynkiewicz, et al., "Analysis of Apoptotic Cells by Flow and Laser Scanning Cytometry", Methods in Enzymol 322, (2000), 18-39.

Daugherty, et al., "Flow Cytometric Screening of Cell-Based Libraries", J Immunol. Methods, 243, (2000), 211-227.

Davies, Michael P.A., et al., "Expression and splicing of the unfolded protein response gene XBP-1 are significantly associated with clinical outcome of endocrine-treated breast cancer", International Journal of Cancer, 123(1), (2008), 85-88.

De, Paula Daniel, et al., "Hydrophobization and bioconjugation for enhanced siRNA delivery and targeting", RNA, vol. 13, (2007), 431-456.

Delepine, et al., "EIF2AK3, Encoding Translation Initiation Factor 2-a Kinase 3, Is Mutated in Patients with Wolcotl-Rallison Syndrome", Nat. Genet, 25, (2000), 406-409.

Desjarlais, et al., "Using Shape Complementarity as an Initial Screen in Designing Ligands for a Receptor Binding Site of Known Three-Dimensional Structure", J. Med. Chem., 31, (1988), 722-729.

Didierlaurent, A M, et al., "AS04, an aluminum salt- and TLR4 agonist-based adjuvant system, induces a transient localized innate immune response leading to enhanced adaptive immunity", J Immunol., vol. 183, (2009), 6186-6197.

Ding, Wen-Xing, et al., "Differential Effects of Endoplasmic Reticulum Stress-Induced Autophagy on Cell Survival", The Journal of Biological Chemistry, 282(7), (2007), 4702-4710.

Ding, Wen-Xing, et al., "Linking of Autophagy to Ubiquitin-Proteasome System Is Important for the Regulation of Endoplasmic Reticulum Stress and Cell Viability", The American Journal, 171(2), (2007), 513-524.

Dioufa, N, et al., "Atypical induction of the unfolded protein response by mifepristone", Endocrine, 38(2), (Jul. 11, 2010), 167-173.

Douglasj, Mahoney, et al., "Virus-tumor interactome screen reveals ER stress response can reprogram resistant cancers for oncolytic virus-triggered Caspase-2 cell death", Cancer Cell, 20(4), (Sep. 13, 2011), 443-456.

Edlund, et al., "Cell Specific Expression of the Rat Insulin Gene: Evidence for Role of Two Distinct 5' Flanking Elements", Science, 230, (1985), 912-916.

Eggerding, et al., "Fluorescence-Based Oligonucleotide Ligation Assay for Analysis of Cystic Fibrosis Tranmembrane Conductance Regulator Gene Mutations", Hum. Mutat., 5, (1995), 153-165.

Eglitis, et al., "Gene Expression in Mice After High Efficiency Retrovirai-Mediated Gene Transfer", Science, 230, (1985), 1395-1398.

Else, K J, et al., "Cytokine-mediated Regulation of Chronic Intestinal Helminth Infection", The Journal of Experimental Medicine, vol. 179, (1994), 347-351.

Engel, et al., "Unfolding new roles for XBP1 in immunity", Nature Immunology, (2010), 365-367.

Falo, L D, et al., "Targeting antigen into the phagocytic pathway in vivo induces protective tumour immunity", Nat Med. 1, (1995), 649-653.

Fassler, R, et al., "Consequences of lack of β1 integrin gene expression in mice", Genes & Development 9, (1995), 1896-1908.

Fauci, A. S., "The human immunodeficiency virus: infectivity and mechanisms of pathogenesis", Science, 239(4840), (1988), 617-22.

Feldman, Douglas E, et al., "The unfolded protein response: A novel component of the hypoxic stress response in tumors", Molecular Cancer Research, American Association for Cancer Research, US, 3(11), (Nov. 1, 2005), 597-605.

Foti, et al., "Conservation and divergence of the yeast and mammalian unfolded protein response. Activation of specific mammalian endoplasmic reticulum stress element of the grp78/BiP promoter by yeast Hac1", J Biol Chem., 274(43), (1999), 30402-30409.

Fowler, D H, et al., "Donor CD4-Enriched Cells of Th2 Cytokine Phenotype Regulate Grall-Versus-Host Disease Nithout Impairing Allogeneic Engrallment in Sublethally Irradiated Mice", Blood, 84(10), (1994), 3540-3549.

Fowler, D H, et al., "Donor Lymphoid Cells of Th2 Cytokine Phenotype Reduce Lethal Grall Versus Host Disease and Facilitate Fully Allogeneic Cell Transfers in Sublethally Irradiated Mice", Advances in Bone Marrow Purging and Processing: FourthIntemational Symposium. Prog. Clin. Biol. Res., vol. 389, (1994), 533-540.

Frank-Kamenetsky, Maria, "Therapeutic RNAi targeting PCSK9 acutely lowers plasma cholesterol in rodents and LDL cholesterol in nonhuman primates", Proc. Natl. Acad.Sci. USA, 105(33), (2008), 11915-11920.

Friedlander, R, et al., "A regulatory link between ER-associated protein degradation and the unfolded protein response", Nature Cell Biology, 2, (2000), 379-384.

Fuchs, et al., "Targeting Recombinant Antibodies to the Surface of *Escherichia coli*: Fusion to a Peptidoglycan Associated Lipoprotein", Bio/Technology, 9, (1991), 1370-1372.

Fujimoto, T, et al., "Upregulation and overexpression of human x-box binding protein 1 (hXBP-1) gene in primary breast cancers", Breast Cancer, 10(4), (2003), 301-306.

Gabay, C, et al., "Acute-Phase Proteins and Other Systemic Responses to Inflammation", New England Journal of Medicine, vol. 340(6), (1999), 448-454.

Garrett, W S, et al., "Communicable ulcerative colitis induced by T-bet deficiency in the innate immune system", Cell, vol. 131, (2007), 33-45.

Gass, J, et al., "The unfolded protein response of B-lymphocytes: PERK-independent development of antibodysecreting cells", Molecular Immunology, vol. 45, (2008), 1035-1043.

Gasser, S, et al., "The DNA damage pathway regulates innate immune system ligands of the NKG2D receptor", Nature, vol. 436, (2005), 1186-1190.

Gefter, Malcolm L, et al., "A Simple Method for Polyethylene Glycol-Promoted Hybridization of Mouse Myeloma Cells", Somatic Cell Genetics, 3, (1977), 231-236.

Genestier, et al., "TLR Agonists Selectively Promote Terminal Plasma Cell Differentiation of B Cell Subsets Specialized in Thymus-Independent Responses", The Journal of Immunology, vol. 178, (2007), 7779-7786.

Gething, et al., "Protein Folding in the Cell", Nature 355, (1992), 33-45.

Ghosh, R, et al., "Transcriptional regulation of VEGF-A by the unfolded protein response pathway", Plos One, 5(3), (2010), 1-12.

Gilchrist, M, et al., "Systems biology approaches identify ATF3 as a negative regulator of Toll-like receptor 4", Nature, 441, (2006), 173-178.

Ginsberg, Henry N, et al., "Metabolic Syndrome: Focus on Dyslipidemia", Obesity, vol. 14, (2006), 41S-49S.

Glimcher, et al., "From Sugar to Fat: How the Transcription Factor XBP1 Regulates Hepatic Lipogenesis", Ann. NY. Acad. Sci., vol. 1173, (2009), E2-E9.

Gorczynski, R M, et al., "Interleukin 12 in Combination With Anti-Interleukin 10 Reverses Graft Prolongation After Portal Venous Immunization", Transplantation, vol. 60(11),, (1995), 1337-1341.

Gossen, M., et al., "Transcriptional Activation by Tetracyclines in Mammalian Cells", Science, 268(5218), (1995), 1766-1769.

Greenbaum, "Insulin resistance in type 1 diabetes", Diabetes/Metabolism Research and Reviews, (2002), 192-200.

Griffin, et al., "DNA Sequencing: Recent Innovations and Future Trends", Appl. Biochem. Biotechnol, 38, (1993), 147-159.

Grzych, J M, et al., "Egg Deposition is the Major Stimulus for the Production of Th2 Cytokines in Murine Schistosomiasis Mansoni", J. Immunol., 146(4), (1991), 1322-1327.

Gu, F, et al., "Protein-tyrosine phosphatase 1B potentiates IRE1 signaling during endoplasmic reticulum stress", Journal of Biological Chemistry, 279(48), (2004), 49689-49693.

Gualdi, Rossana, et al., "Hepatic specification of the gut endoderm in vitro: cell signaling and transcriptional control", Genes & Development, 10, (1996), 1670-1682.

(56) References Cited

OTHER PUBLICATIONS

Gunes, C, et al., "Embryonic lethality and liver degeneration in mice lackin the metal-responsive transcriptional activator MTF-1", EMBO J., vol. 17, (1998), 2846-2854.
Hampton, et al., "ER Stress Response: Getting the UPR Hand on Misfolded Proteins", Curro; Biol., 10, (2000), R518.
Han, et al., "IRE1a Kinase Activation Modes Control Alternate Endoribonuclease Outputs to Determine Divergent Cell Fates", (2009), 1-21.
Hanes, Jozef, et al., "Picomolar affinity antibodies from a fully synthetic naive library selected and evolved by ribosome display", Nature Biotechnology, 18(12), (Dec. 2000), 1287-1291.
Harding, et al., "An integrated stress response regulates amino acid metabolism and resistance to oxidative stress", Mol Cell., 11(3), (2003), 619-633.
Harding, et al., "Diabetes Mellitus and Exocrine Pancreatic Dysfunctional Perk-1-Mice Reveals a Role for Translational Control in Secretary Cell Survival", Molecular Cell, 7, (2001), 1153-1163.
Harding, et al., "Protein Translation and Folding Are Coupled by an Endoplasmic-Reticulum-Resident Kinase", Nature, 397, (1999), 271-274.
Harding, et al., "Regulated translation initiation controls stress-induced gene expression in mammalian cells", Mol Cell,6(5), (2000), 1099-1108.
Haseloff, Jim, et al., "Simple RNA enzymes with new and highly specific endoribonuclease activities", Nature, 344, (1988), 585-591.
Hayashi, "PCR-SSCP: A Simple and Sensitive Method for Detection of Mutations in the Genomic DNA", Genome Res.,1, (1991), 34-38.
Heikkila, et al., "The prevention of alloxan-induced diabetes in mice by dimethyl sulfoxide", European Journal of Pharmacology, Elsvier, BV, NL, 44(2), (1977), 191-193.
Helene, et al., "The Anti-Gene Strategy: Control of Gene Expression by Triplex-Forming-Oligonucleotides", Anticancer Drug Des., 6(6), (1991), 569-584.
Hentsch, B, et al., "Hlx homeo box gene is essential for an inductive tissue interaction that drives expansion of embryonic liver and gut", Genes Dev., vol. 10, (1996), 70-79.
Hetz, et al., "Fine-Tuning of the Unfolded Protein Response: Assembling the IRE1 a Interactome", Mol. Cell, (2009), 551-561.
Hetz, C, et al., "Proapoptotic BAX and BAK modulate the unfolded protein response by a direct interaction with IRE1alpha", Science, 31, (2006), 572-576.
Hetz, Claudio, et al., "The Unfolded Protein Response: Intergrating Stress Signals Through the Stress Sensor IRE1 alpha", Physiol Rev., vol. 91, (2011), 1219-1243.
Hetz, Claudio, et al., "Unfolded protein response transcription factor XBP-1 does not influence prion replication of pathogenesis", Proc. Natl. Acad. Sci. USA, 105(2), (2008), 757-762.
Hetz, Claudio, et al., "XBP-1 and the UPRosome: Mastering Secretory Cell Function", Current Immunology Reviews, vol. 4, (2008), 1-10.
Hetz, Claudio, et al., "XBP-1 deficiency in the nervous system protects against amyotrophic lateral sclerosis by increasing autophagy", Genes & Development, vol. 23, (2009), 2294-2306.
Hirano, et al., "Excessive Production of Interleukin 61B Cell Stimulatory Factor-2 in Rheumatoid Arthritis", Eur. J. Immunol.18, (1988), 1797-1801.
Hirano, et al., "Interleukin 6 and Plasma Cell Neoplasias", Prog. Growth Fact Res., 1, (1989), 133-142.
Hirosumi, et al., "A Central Role for JNK. In Obesity and Insulin Resistance", Nature, 420, (2002), 333-336.
Hirsch, Emilio, et al., "Impaired migration but not differentiation of haematopoietic stem cells in the absence of $\beta_1$ Integrins", Nature, vol. 380, (1996), 171-175.
Hollien, J, et al., "Decay of endoplasmic reticulum-localized mRNAs during the unfolded protein response", Science, 313, (2006), 104-107.
Hollien, J, et al., "Regulated Ire1-dependent decay of messenger RNAs in mammalian cells", J Cell Biol., vol. 186, (2009), 323-331.
Horii, et al., "Involvement of IL-6 in Mesangial Proliferative Glomerulonephritis", J Immunol., 143 (12), (1989), 3949-3955.
Hosokawa, et al., "A novel ER a-mannosidase-like protein accelerates ER-associated degradation", EMBO Rep., 2(5), (2001), 415-422.
Hosokawa, N, et al., "EDEM accelerates ERAD by preventing aberrant dimer formation of misfolded alpha1-antitrypsin", Genes to Cells, vol. 11, (2006), 465-476.
Hosseini, Hassan, et al., "Protection against experimental autoimmune encephalomyelitis by a proteasome modulator", Journal of Neuroimmunology, 188, (2001), 233-244.
Hotamisligil, "Inflammatory Pathways and Insulin Action", International Journal of Obesity, 27, (2003), S53-S55.
Hoyer-Hansen, M, et al., "Connecting endoplasmic reticulum stress to autophagy by unfolded protein response and Calcium", Cell Death and Differentiation, vol. 14, (2007), 1576-1582.
Hu, Fanlei, et al., "ER stress and its regulator X-box-binding protein-1 enhance polyIC-induced innate immune response in dendritic cells", European Journal of Immunology, 41(4), (Apr. 14, 2011), 1086-1097.
Huang, Q, et al., "The plasticity of dendritic cell responses to pathogens and their components", Science, vol. 294, (2001), 870-875.
Ilieva, E, et al., "Oxidative and endoplasmic reticulum stress interplay in sporadic amyotrophic lateral sclerosis", Brain, vol. 130, (2007), 3111-3123.
Iwakoshi, et al., "Plasma cell differentiation and the unfolded protein response intersect at the transcription factor XBP-1", Nat Immunol., 4(4), (2003), 321-329.
Iwakoshi, et al., "The transcription factor XBP-1 is essential for the development and survival of dendritic cells", J Exp Med. vol. 204, (2007), 2267-2275.
Iwawaki, T, et al., "Function of IRE1 alpha in the placenta is essential for placental development and embryonic viabilily", PNAS, vol. 106, (2009), 16657-16662.
Jacks, T, et al., "Effects of an Rb mutation in the mouse", Nature, vol. 359, (1992), 295-300.
Johnson, C P, et al., "Forced unfolding of proteins within cells", Science, vol. 317, (2007), 663-666.
Kakiuchi, et al., "Impaired feedback regulation of XBP1 as a genetic risk factor for bipolar disorder", Nat Genet. 35(2), (2003), 171-175.
Karin, et al., "Phosphorylation meets ubiquitination: the control of NF-[kappa]B activity", Annu Rev Immunol., vol. 18, (2000), 621-663.
Kaser, a, et al., "Endoplasmic reticulum stress in the intestinal epithelium and inflammatory bowel disease", Seminars in Immunology, W.B. Saunders Company, PA, US, 21(3), (2009), 156-163.
Kaser, A, et al., "XBP1 links ER stress to intestinal inflammation and confers genetic risk for human inflammatory bowel disease", Cell, vol. 134, (2008), 743-756.
Katze, "Regulation of the interferon-induced PKR: can viruses cope?", Trends Microbiol. 3(2), (1995), 75-78.
Kaufman, D R, et al., "Route of adenovirus-based HIV-1 vaccine delivery impacts the phenotype and trafficking of vaccine-elicited COB+ T lymphocytes", J Virol, vol. 84, (2010), 5986-5996.
Kaufman, D R, et al., "Trafficking of antigen-specific COB+ T lymphocytes to mucosal surfaces following intramuscular vaccination", J Immunol., 181, (2008), 4188-4198.
Kaufman, R J, et al., "Inositol-requiring 1/X-box-binding protein 1 is a regulatory hub that links endoplasmic reticulum homeostasis with innate immunity and metabolism", EMBO Mol Med., vol. 2, (2010), 189-192.
Kaufman, R J, "Orchestrating the unfolded protein response in health and disease", The Journal of Clinical Investigation, vol. 110(10), (2002), 389-1398.
Kawai, T, et al., "TLR signaling", Semin Immunol., 19, (2007), 24-32.
Khoury, S J, et al., "Oral Tolerance to Myelin Basic Protein and Natural Recovery from Experimental Autoimmune Encephalomyelitis Are Associated with Downregulation of Inflammatory Cytokines and Differential Upregulation of Transforming Growth Factor.beta., Interleukin 4, and Pr", J. Exp. Med., vol. 176, (1992), 1355-1364.

(56) References Cited

OTHER PUBLICATIONS

Kieran, D, et al., "Deletion of the BH3-only protein puma protects motoneurons from ER stress-induced apoptosis and delays motoneuron loss in ALS mice", Proc. Natl. Acad. Sci. USA, 104(51), (2007), 20606-20611.
Kikuchi, et al., "Functional analysis of human P5, a protein disulfide isomerase homologue", J Biochem (Tokyo).,132(3), (2002), 451-455.
Kikuchi, H, et al., "Spinal cord endoplasmic reticulum stress associated with a microsomal accumuilation of mutant superoxide dismutase-1 in an ALS model", Proc. Acad. Sci. USA, 103(15), (2006), 6025-6030.
Kinnebrew, M A, et al., "Bacterial flagellin stimulates Toll-like receptor 5-dependent defense against vancomycinesistant Enterococcus infection", J Infect Dis., 201(4), (2010), 534-543.
Kishimoto, T, et al., "Enhanced Expression of a New Class of Liver-enriched b-Zip Transcription Factors Hepatocarcinogenesis-related Transcription Factor, in Hepatocellular Carcinomas of Rats and Humans", Cell Growth & Differentiation, 9, (1998), 337-334.
Kisselev, et al., "Proteasome inhibitors: from research tools to drug candidates", Chem Biol., 8(8), (2001), 739-758.
Kokura, K, et al., "Identity between rat htf and human xbp-1 genes: determination of gene structure, target sequence, and transcription promotion function for HTF", GenBank Accession No. BAA82600, Gene, 241(2), (2000), 297-307.
Komatsu, M, et al., "Loss of autophagy in the central nervous system causes neurodegeneration in mice", Nature, vol. 441, (2006), 880-884.
Kono, H, et al., "How dying cells alert the immune system to danger", Nat Rev Immunol., 8(4), (2008), 279-289.
Koong, Albert C, "Targeting XBP-1 as a novel anti-cancer strategy", Cancer Biology & Therapy, 5(7), (2006), 756-759.
Korennykh, A V, et al., "The unfolded protein response signals through high-order assembly of Ire1", Nature, 457, (2009), 687-693.
Kovacsovics-Bankowski, M, et al., "Efficient major histocompatibility complex class I presentation of exogenous antigen upon phagocytosis by macrophages", Proc. Natl. Acad. Sci. USA, 90, (1993), 4942-4946.
Kullberg, M. C., et al., "Infection With *Schislosoma mansoni* Allers Th1/Th2 Cytokine Responses to a Non-Parasite Antigen", J. Immunol., 148(10), (1992), 3264-3270.
Kurisu, et al., "MDG1/ERdj4, an ER-resident DnaJ family member, suppresses cell death induced by ER stress", Genes Cells, 8(2), (2003), 189-202.
Lee, A H, et al., "Prolesome inhibitors disrupt the unfolded protein response in myeloma cells", Proc. Natl. Acad. Sci. USA,100(17), (2003), 9946-9951.
Lee, A H, et al., "Regulation of Hepatic Lipogenesis by the Transcription Factor XBP1", Science, 320, (2008), 1492-1496.
Lee, A H, et al., "Tumour necrosis factor-alpha and interferon-gamma synergistically activate the RANTES promoter through nuclear factor kappaB and interferon regulatory factor 1 (IRF-1) transcription factors", Biochem J., 350, (2000), 131-8.
Lee, A H, et al., "XBP-1 is required for biogenesis of cellular secretory machinery of exocrine glands", EMBO J., 24, (2005), 4368-4380.
Lee, A H, et al., "XBP-1 regulates a subset of endoplasmic reticulum resident chaperone genes in the unfolded protein response", Mol Cell Biol., 23, (2003), 7448-7459.
Lee, Eva Y-H-P, et al., "Mice deficient for Rb are nonviable and show defects in neurogenesis and haemalopoiesis", Nature, 359, (1992), 288-294.
Lee, T G, et al., "Purification and partial characterization of a cellular inhibitor of the inlerferoninduced protein kinase of M, 68,000 from influenza virus-infected cells", Proc Nall Acad Sci USA, 87(16), (1990), 6208-6812.

Levy, Adam E, et al., "Administration of Ingraft Inlerleukin-4 Prolongs Cardiac Allografl Survival in Rais Treated With Donor-specific Transfusion/Cyclosporine", Transplantation,. 60(5), (1995), 405-406.
Lindsten, et al., "A transgenic mouse model of the ubiquitin/proteasome system", Nat Biolechnol, 21(8), (2003), 897-902.
Liou, H C, et al.,GenBank Accession No. P17861, Science, vol. 247, (1990), 1581-1584.
Liou, H C, et al., "A new member of the leucine zipper class of proteins that binds to the HLA DR alpha promoter", Science, vol. 247, (1990), 1581-1584.
Lisbona, F, et al., "BAX inhibitor-1 is a negative regulator of the ER stress sensor IRE1alpha", Mol Cell, 33(6), (2009), 679-691.
Litvak, V, et al., "Function of C/EBP delta in a regulatory circuit that discriminates between transient and persistent TLR4-induced signals", Nat Immunol., vol. 10, (2009), 437-443.
Liu, C Y, et al., "Ligand-independent dimerization activates the stress response kinases IRE1 and PERK in the lumen of the endoplasmic reticulum", J Biol Chem., vol. 275(32), (2000), 24881-24885.
Liu, J, et al., "Modulation of DNA vaccine-elicited COB+ T-lymphocyte epitope immunodominance hierarchies", J Virol,80, (2006), 11991-11997.
Locksley, R M, et al., "Helper T-cell subsets in mouse leishmaniasis: induction, expansion and effector function", Immunoparasitiology Today, vol. 1, (1991), A58-A61.
Luo, D, et al., "AIP1 is critical in transducing IRE1-mediated endoplasmic reticulum stress response", Journal of Biological Chemistry, 283(18), (2008), 11905-11912.
Luo, H C, et al., "Spontaneous calcification of arteries and cartilage in mice lacking matrix GLA protein", Nature,386(6620), (1997), 78-81.
Luo, Hongyu, et al., "A Proteasome Inhibitor Effectively Prevents Mouse Heart Allograft Rejection", Transplantation, 72(2), (Jul. 27, 2001), 196-202.
Ma, Y, et al., "Plasma cell differentiation initiates a limited ER stress response by specifically suppressing the PERK-dependent branch of the unfolded protein response", Cell Stress and Chaperones, vol. 15, (2010), 281-293.
Ma, Y, et al., "The unfolding tale of the unfolded protein response", Cell, 107(7), (2001).
Maeda, H, et al., "Adoptive transfer of a Th2-like cell line prolongs MHC class II antigen disparate skin allografl survival in the mouse", International Immunology, 6(6), (1994), 855-862.
Maekawa, T, et al., "Mouse ATF-2 null mutants display features of a severe type of meconium aspiration syndrome", The Journal of Biological Chemistry, 274(25), (1999), 17813-17819.
Malyala, P, et al., "Enhancing the therapeutic efficacy of CpG oligonucleotides using biodegradable microparticles", Adv Drug Deliv Rev., 61, (2009), 218-225.
Malyala, P, et al., "The potency of the adjuvant, CpG oligos, is enhanced by encapsulation in PLG microparticles", Pharm Sci., 97, (2008), 1155-1164.
Martinon, F, et al., "Regulation of innate immunity by signaling pathways emerging from the endoplasmic reticulum", Current Opinion in Immunology, 23, (2010), 1-6.
Martinon, F, et al., "TLR activation of the transcription factor XBP1 regulates innate immune responses in macrophages", NalImmunol. 11, (2010), 411-418.
Matus, S, et al., "The Stress Rheostat: An Interplay Between the Unfolded Protein Response (UPR) and Autophagy in Neurodegeneration", Current Molecular Medicine, vol. 8, (2008), 157-172.
McLean, Cory Y., et al., "GREAT improves functional interpretation of cis-regulatory regions", Nature Biotechnology, 28(5), (May 2010), 495-501.
Medzhitov, R, "Origin and physiological roles of inflammation", Nature, 454, (2008), 428-435.
Melville, et al., "The cellular inhibitor of the PKR protein kinase, P58$^{IPK}$, is an inftuenza virus activated co-chaperone that modulates heat shock protein activity", J Biol Chem., 274(6), (1999), 3797-3803.

(56) References Cited

OTHER PUBLICATIONS

Meng, et al., "Exponemycin exerts its antitumor effect through the inhibition of proteasome function", Cancer Res., 59(12), (1999), 2798-2801.

Meng, Lihao, et al., "Epoxomicin, a potent and selective proteasome inhibitor, exhibits in vivo antiinflammatory activity", Proc Natl Acad Sci USA, 96(18), (Aug. 31, 1999), 10403-8.

Meusser, B, et al., "ERAD: the long road to destruction", Nature Cell Biology, 7(8), (2005), 766-772.

Mikkelsen, T S, et al., "Genome-wide maps of chromatin state in pluripotent and lineage-committed cells", Nature, 448, (2007), 553-560.

Molinari, et al., "Role of EDEM in the release of misfolded glycoproteins from the calnexin cycle", Science, 299, (2000), 1397-1400.

Moore, M W, et al., "Introduction of soluble protein into the class I pathway of antigen processing and presentation", Cell, 54, (1988), 777-785.

Mucenski, M L, et al., "A Functional c-myb Gene Is Required for Nonrnal Murine Fetal Hepatic Hematopoiesis", Cell, 65, (1991), 677-689.

Nagata, T, et al., "Increased ER stress during motor neuron degeneration in a transgenic mouse model of amyotrophic lateral sclerosis", Neurological Research, 29, (2007), 767-771.

Nau, G J, et al., "Human macrophage activation programs induced by bacterial pathogens", PNAS, USA, vol. 99, (2002), 1503-1508.

Newman, J, et al., "Comprehensive identification of Human bZIP Interactions with Coiled-Coil Arrays", Science, 300, (2003), 2097-2101.

Nishiloh, H, et al., "ASK1 is essential for endoplasmic reticulum stress-induced neuronal cell death triggered by expanded polyglutamine repeats", Genes and Development, vol. 16, (2003), 1394-1397.

Oda, et al., "EDEM as an acceptor of terminally misfolded glycoproleins released from calnexin", Science, 299, (2003), 1394-1397.

Ogata, M, et al., "Autophagy Is Activated for Cell Survival after Endoplasmic Reticulum Stress", Molecular and Cellular Biology, 26(24), (2006), 9220-9231.

Ohtsuka, et al., "Mammalian HSP40/DNAJ homologs: cloning of novel cDNAs and a proposal for their classification and nomenclature", Cell Stress Chaperones, 5(2), (2000), 98-112.

Okada, et al., "Distinct roles of activating transcription factor 6 {ATF6) and double-stranded RNA-activated protein kinase-like endoplasmic reticulum kinase {PERK) in transcription during the mammalian unfolded protein response", Biochem J., 366(Pt 2), (2002), 585-594.

O'Neill, L, et al., "The family of five: TIR-domain-containing adaptors in Toll-like receptor signalling", Nat Rev Immunol, vol. 7, (2007), 353-364.

Ota, T, et al., "Inhibition of apolipoprolein B100 secretion by lipid-induced hepatic endoplasmic reticulum stress in rodents", The Journal of Clinical Investigation, vol. 118(1), (2008), 316-332.

Ozcan, et al., "Chemical Chaperones Reduce ER Stress and Restore Glucose Homeostasis in a Mouse Model of Type 2 Diabetes", Science, (2006), 1137-1140.

Parker, R, et al., "Endoplasmic Reticulum Stress Links Dyslipidemia to Inhibition of Proteasome Activity and Glucose transport by HIV Protease Inhibitors", Molecular Pharmacology, vol. 67(6), (2005), 1909-1919.

Pati, et al., "Antitumorigenic effects of HIV protease inhibitor rilonavir: inhibition of Kaposi sarcoma", Blood, 99(10), (2002), 3771-3779.

Paul, W, et al., "Lymphocyte Responses and Cytokines", Cell, vol. 76, (1994), 241-251.

Pearce, E J, et al., "Downregulation of Th1 Cytokine Production Accompanies Induction of Th2 Responses by a Parasitic Helminth, *Schistosoma mansoni*", J. Exp. Med., 173, (1991), 159-166.

Pearlman, E, et al., "Induction of Murine T-Helper-Cell Responses to the Filarial Nematode *Brugia malayi*", Infection and Immunity, 61(3), (1993), 1105-1112.

Peisach, E, et al., "Interaction of a peptidomimetic aminimide inhibitor with elastase", Science, 269{5220), (1995), 66-69.

Peng, et al., "NFATc1 and NFATc2 together control both T and B cell activation and differentiation", Immunity, 14, (2001), 13-20.

Persing, D H, et al., "Taking toll: lipid A mimelics as adjuvanls and immunomodulalors", Trends Microbiol., 10, (2002), S32-37.

Pisa, P, et al., "Selective expression of interleukin 10, interferon y, and granulocyte-macrophage colony-stimulating actor in ovarian cancer biopsies", Proc. Natl. Acad. Sci. USA, 89, (1992), 7708-7712.

Ranger, et al., "Inhibitory function of two NFAT family members in lymphoid homeostasis and Th2 development", Immunity, 9(5), (1998), 627-635.

Rao, R, et al., "Misfolded proteins, endoplasmic reticulum stress and neurodegeneration", Current Opinion in Cell Biology, 16, (2004), 653-662.

Rapoport, M, et al., "Interleukin 4 Reverses T Cell Proliferative Unresponsiveness and Prevents the Onset of diabetes in Nonobese Diabetic Mice", J. Exp. Med., 178, (1993), 87-99.

Ravasi, T, et al., "Systems biology of transcription control in macrophages", Bioessays, vol. 29, (2007), 1215-1226.

Raychaudhuri, S, et al., "Fully mobilizing host defense: building better vaccines", Nat Biotechnol., vol. 16, (1998), 1025-1031.

Raychaudhuri, S, et al., "Identifying relationships among genomic disease regions: predicting genes at pathogenic SNP associations and rare deletions", PLoS Genet 5, e1000534, (2009), 15 pgs.

Reddy, J, et al., "Lipid Metabolism and Liver Inflammation II. Fatty liver disease and fatty acid oxidation", Am. J. Physiol. Gastrointest Liver Physiol., 290, (2006), G852-G858.

Reimold, et al., "Plasma cell differentiation requires the transcription factor XBP-1", Nature, 412(6844), (2001), 300-307.

Reimold, A M, et al., "An essential role in liver development for transcription factor XBP-1", Genes & Development 14, (2000), 152-157.

Reimold, A, et al., "Chondrodysplasia and neurological abnormalities in ATF-2-deficient mice", Nature, 379, (1996), 262-265.

Reimold, A, et al., "Control of Terminal B Cell Differentiation by Transcription Factor XBP-1", vol. 42(9 Suppl.):S58, Poster No. 52, (1999).

Reimold, A, et al., "Transcription Factor B Cell Lineage-specific Activator Protein Regulates the Gene for Human XBox Binding Protein 1", J. Exp. Med., 183, (1996), 393-401.

Richardson, C E, et al., "An essential role for XBP-1 in host protection against immune activation in *C.elegans*", Nature, 463, (2010), 1092-1095.

Roach, J C, et al., "Transcription factor expression in lipopolysaccharide-activated peripheral-blood-derived mononuclear cells", Proc. Natl. Acad. Sci. USA, 104, (2007), 16245-16250.

Robertson, G, et al., "Genome-wide profiles of STAT1 DNA association using chromatin immunoprecipitation and massively parallel sequencing", Nat Methods, 4, (2007), 651-657.

Rock, et al., "Degradation of cell proteins and the generation of MHC class I-presented peptides", Annu Rev Immunol, vol. 17, (1999), 739-779.

Rock, K L, et al., "Analysis of the role of MHC class II presentation in the stimulation of cytotoxic T lymphocytes by antigens targeted into the exogenous antigen-MHC class I presentation pathway", J Immunol., vol. 156, (1996), 3721-3726.

Romero-Ramirez, Lorenzo, et al., "XBP1 is essential for survival under hypoxic conditions and is required for tumor growth", Cancer Research, American Association for Cancer Research, US, vol. 64, No. 17, (Sep. 1, 2004), 5943-5947.

Rong, J, et al., "BAR, an endoplasmic reticulum-associated E3 ubiquitin ligase, modulates BI-1 protein stability and function in ER stress", Journal of Biological Chemistry, vol. 286 (2),, (2010), 1453-1463.

Rudolph, D, et al., "Impaired fetal T cell development and perinatal lethality in mice lacking the cAMP response element binding protein", Proc. Natl. Acad. Sci. USA., 95(8), (1998), 4481-4486.

Ruegsegger, et al., "Block of HAC1 mRNA Translation by Long-Range Base Pairing Is Released by Cytoplasmic Splicing Upon Induction of the Unfolded Protein Response", Cell, vol. 107, (2001), 103-114.

(56) References Cited

OTHER PUBLICATIONS

Samuel, "The eIF-2a protein kinases, regulators of translation in eukaryotes from yeasts to humans", J Biol Chem., 268(11), (1993), 7603-7606.
Schmidt, C, et al., "Scatter factor/hepatocyte growth factor is essential for liver development", Nature, 373, (1995), 699-702.
Schmitz, et al., "Transcriptional activation induced in Macrophages by toll-like receptor {TLR} ligands: from expression Profiling to a model of TLR signaling", European Journal of Immunology 34, (2004), 2863-2873.
Schroder, et al., "Control of glycosylation of MHC class II-associated invariant chain Cy transloco-associaled RAMP4", EMBO J, 18(17), (1999), 4804-4815.
Schurr, J R, et al., "Central role of toll-like receptor 4 signaling and host defense in experimental pneumonia caused by Gram-negative bacteria", Infect Immun., 73, (2005), 532-545.
Semir, Vranic, et al., "Angiogenesis in triple-negative adenoid cystic carcinomas of the breast", Virchows Archiv, Springer, Berlin, DE, 459(4), (Sep. 4, 2011), 377-382.
Servillo, G, et al., "Transcription factor CREM coordinates the liming of hepatocyte proliferation in the regenerating liver", Genes & Development, 12, (1998), 3639-3643.
Sgadari, et al., "HIV protease inhibitors are potent anti-angiogenic molecules and promote regression of Kaposi sarcoma", Nat Med. 8(3), (2002), 225-232.
Sha, H, et al., "The IRE1-XBP1 pathway of the unfolded protein response is required for adipogenesis", Cell Metabolism, 9(6), (2009), 556-564.
Shaffer, et al., "XBP1, Downstream of Blimp-1, Expands the Secretory Apparatus and Other Organelles, and Increases Protein Synthesis in Plasma Cell Differentiation", Immunity, 21, (2004), 81-93.
Shapira, S D, et al., "A physical and regulatory map of host-influenza interactions reveals pathways in H1N1 infection", Cell, 139, (2009), 1255-1267.
Shearer, G, et al., "T helper cell immune dysfunction in asymptomatic, HIV-1-seropositive individuals: the role of TH1-TH2 cross-regulation", Chem. Immunol., 54, (1992), 21-43.
Shen, et al., "Complementary Signaling Pathways Regulate the Unfolded Protein Response and Are Required for C. Elegans Development", Cell, 107, (2001), 893-903.
Shen, et al., "Identification and Characterization of a Novel Endoplasmic Reticulum (ER) Dnaj Homologue which Stimulates ATPase Activity of BiP in vitro and is Induced by ER Stress", J. Bio Chem., 277(18), (2001), 15947-15956.
Sigma-Aldrich, "Lipoprotein Function and Lipid Transport", http://www.sigmaaldrich.com/Area.sub.Jf.sub.Interest/Biochemicals/Enzyme, (2008), 3 pgs.
Simon, A K, et al., "Divergent T-cell cytokine patterns in inflammatory arthritis", Proc. Natl. Acad. Sci. USA, 91, (1994), 8562-8566.
Singh, M, et al., "Polylactide-co-glycolide microparticles with surface adsorbed antigens as vaccine delivery systems", Curr Drug Deliv., 3, (2006), 115-120.
Sriburi, R, et al., "Coordinate Regulation of Phospholipid Biosynthesis and Secretory Pathway Gene Expression in KBP-1{S)-induced Endoplasmic Reticulum Biogenesis", The Journal of Biological Chemistry, 282(10), (2007), 7024-7034.
Sriburi, R, et al., "XBP1: a link between the unfolded protein response, lipid biosynthesis, and biogenesis of the endoplasmic reticulum", The Journal of Cell Biology, 167(1), (2004), 35-41.
Struhl, K, "Transcriptional noise and the fidelity of initiation by RNA polymerase II", Nat Struct Mol Bioi.,14, (2007), 103-105.
Sullivan, B M, et al., "Antigen-driven effector CD8 T cell function regulated by T-bet", Proc Nall Acad Sci USA, 100, (2003), 15818-15823.
Takahashi, T, et al., "Antiobesity agent for treating and preventing obesity, comprises extract of betaine, dandelion, turmeric, red pepper and/or Lonicera japonoica, as active ingredients", Derwent, (Jan. 1, 1900), 1 pg.

Takeuchi, T., et al., "Heart allografts in murine systems. The differential activation of Th2-like effector cells in peripheral tolerance.", Transplantation. 53(6), (1992), 1281-91.
Taub, R, "Transcriptional control of liver regeneration", FASEB J., vol. 10, (1996), 413-427.
Thai, N, et al., "Cytokine mRNA Profiles in Mouse Orthotopic Liver Transplantation", Transplantation, 59(2), (1995), 274-281.
Thomas, Karn, et al., "Homogeneous Datasets of Triple Negative Breast Cancers Enable the Identification of Novel Prognostic and Predictive Signatures", PLOS ONE, 6(12), (Dec. 29, 2011), e28403-e28403.
Todd, D, et al., "XBP1 governs late events in plasma cell differentiation and is not required for antigen specific memory B cell development", J Exp Med., 206, (2009), 2151-2159.
Turner, B, et al., "ER Stress and UPR in Familial Amyotrophic Lateral Sclerosis", Current Molecular Medicine, vol. 6, (2006), 79-86.
Turner, M, et al., "HLA-B27 misfolding in transgenic rats is associated with activation of the unfolded protein response", Journal of Immunology, vol. 175, (2005), 2438-2448.
Tzakis, A G, et al., "Early Tolerance in Pediatric Liver Allografl Recipients", J. Pediatr. Surg., 29(6), (1994), 754-756.
Uehara, Y, et al., "Placental defect and embryonic lethality in mice lacking hepatocyte growth factor/scatter factor", Nature, 373, (1995), 702-705.
Urano, et al., "A survival pathway for Caenorhabditis elegans with a blocked unfolded protein response", J Cell Biol. 158(4), (2002), 639-646.
Urano, F, et al., "Coupling of stress in the ER to activation of JNK protein kinases by transmembrane protein kinase IRE1", Science, 287, (2000), 664-666.
Urushitani, M, et al., "Chromogranin-mediated secretion of mutant superoxide dismutase proteins linked to amyotrophic lateral sclerosis", Nature Neuroscience, 9(1), (2006), 108-118.
Van, Beusechem, et al., "Long-Term Expression of Human Adenosine Deaminase in Rhesus Monkeys Transplanted Nith Retrovirus-Infected Bone-Marrow Cells", Proc. Natl. Acad. Sci. USA 89, (1992), 7640-7644.
Van, Huizen R, et al., "P581PK, a novel endoplasmic reticulum stress-inducible protein and potential negative regulator of eIF2alpha signaling", Journal of Biological Chemistry, 278(18), (2003), 15558-15564.
Van, Limbergen J, et al., "The genetics of Crohn's disease", Annual Review of Genomics and Human Genetics 2009 vol. 10, (May 2009), 89-116.
Vlug, A, et al., "ATF3 expression precedes death of spinal motoneurons in amyotrophic lateral sclerosis-SOD1 transgenic mice and correlates with c-Jun phosphorylation, CHOP expression, somatodendritic ubiquitination and Golgi fragmentation", European Journal of Neuroscience, vol. 22, (2005), 1881-1894.
Wang, et al., "Oligomeric complexes involved in translocation of proteins across the membrane of the endoplasmic reticulum", FECS Lett., 457(3), (1999), 316-322.
Wiseman, R, et al., "Flavonol activation defines an unanticipated ligand-binding site in the kinase-RNase domain of IRE1", Molecular Cell, 38(2), (2009), 291-304.
Wong, C C, et al., "Hypoxia-inducible factor 1 is a master regulator of breast cancer metastatic niche formation", Proceedings of the National Academy of Sciences, vol. 108, No. 39, (Sep. 27, 2011), 16369-16374.
Woo, C W, et al., "Adaptive suppression of the ATF4-CHOP branch of the unfolded protein response by toll-like receptor signalling", Nat Cell Biol. 11, (2009), 1473-1480.
Wootz, H, et al., "Caspase-12 cleavage and increased oxidative stress during mononeuron degeneration in transgenic mouse model of ALS", Biochemical and Biophysical Research Communications, 322, (2004), 281-286.
Wootz, H, et al., "XIAP decreases caspase-12 cleavage and calpain activity in spinal cord of ALS transgenic mice", Experimental Cell Research, 312, (1890-1898), 2006.
Wu, X, et al., "HIV protease inhibitors induce endoplasmic reticulum stress and disrupt barrier integrity in intestinal epithelial cells", Gastroenterology, Gastroenterology, vol. 138, (2010), 197-209.

(56) References Cited

OTHER PUBLICATIONS

Xiao-Mei, Zhu, et al., "Endoplasmic reticulum stress and its regulator XBP-1 contributes to dendritic cell maturation and activation induced by high mobility group box-1 protein", International Journal of Biochemistry and Cell Biology, Pergamon, GB, 44(7), (Mar. 27, 2012), 1097-1105.
Xu, et al., "The Role of CD40-CD 154 Interaction in Cell Immunoregulation", J Biomed Sci, (2004), 426-438.
Xu, Y, "DNA damage: a trigger of innate immunity but a requirement for adaptive immune homeostasis", Nat Rev Immunol., vol. 6, (2006), 261-270.
Yamaguchi, et al., "Stress-associated endoplasmic reticulum protein 1 (SERP1)/Ribosomel associated membrane protein 4 (RAMP4) stabilizes membrane proteins during stress and facilitates subsequent glycosylation", J Cell Biol. vol. 147(6), (1999), 1195-1204.
Yamamura, M, et al., "Local Expression of Antiinflammatory Cytokines in Cancer", The Journal of Clinical Investigation, 91, (1993), 1005-1010.
Yan, et al., "Control of PERK eIF2a kinase activity by the endoplasmic reticulum stress-induced molecular chaperone P581PK", Proc. Natl. Acad. Sci. USA., 99(25), (2002), 15920-15925.
Yanagitani, K, et al., "Cotranslational targeting of XBP1 protein to the membrane promotes cytoplasmic splicing of its own mRNA", Mol Cell, vol. 34, (2009), 191-200.
Yang, et al., "Ubiquitin protein ligase activity of IAPs and their degradation in proteasomes in response to apoptotic stimuli", Science, 88(5467), (2000), 874-877.
Yang, L, et al., "FZD7 has a critical role in cell proliferation in triple negative breast cancer", Oncogene, 30(43), (Oct. 27, 2011), 4437-4446.
Yoneda, T, et al., "Activation of caspase-12, an endoplasmic reticulum {ER} resident caspase, through tumor necrosis actor receptor-associated factor 2-dependent mechanism in response to ER stress", Journal of Biological Chemistry, 276(17), (2001), 13935-13940.
Yoshida, et al., "A Time-Dependent Phase Shift in the Mammalian Unfolded Protein Response", Dev Cell, 4(2), (2003), 265-271.
Yoshida, et al., "ATF6 Activated by Proteolysis Binds in the Presence of NF-Y {CBF} Directly to the cis-Acting Element Responsible for the Mammalian Unfolded Protein Response", Molecular and Cellular Biology, vol. 20(18), (2000), 6755-6767.
Yoshida, et al., "XBP1 mRNA Is Induced by ATF6 and Spliced by IRE1 in Response to ER Stress to Produce a Highly Active Transcription Factor", Cell, 107, (2001), 881-891.
Yoshizaki, et al., "Pathogenic Significance of Interleukin-6 (IL-60/BSF-2) in Castleman's Disease", Blood 74, (1989), 1360-1367.
Zhang, K, et al., "From endoplasmic-reticulum stress to the inflammatory response", Nature, 454, (2008), 455-462.
Zhang, K, et al., "The unfolded protein response sensor IRE1alpha is required at 2 distinct steps in B cell lymphopoiesis", J Clin Invest.,115, (2005), 268-281.
Zhou, H, et al., "HIV protease inhibitors increase TNF-alpha and IL-6 expression in macrophages: involvement of the RNA-binding protein HuR", 195, (2007), 134-143.
Zhu, et al., "Interaction of ATF6 and serum response factor", Mol Cell Biol. 17(9), (1997), 4957-4966.
Zollner, et al., "Proteasome inhibition reduces superantigen-mediated T cell activation and the severity of psoriasis in a SCID-hu model", J Clin Invest. 109(5), (2002), 671-679.

\* cited by examiner

Fig. 2A  Fig. 2B

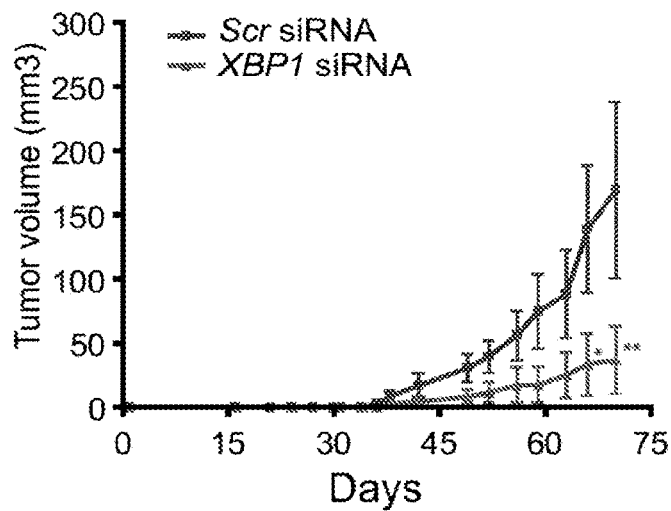
Fig. 3H
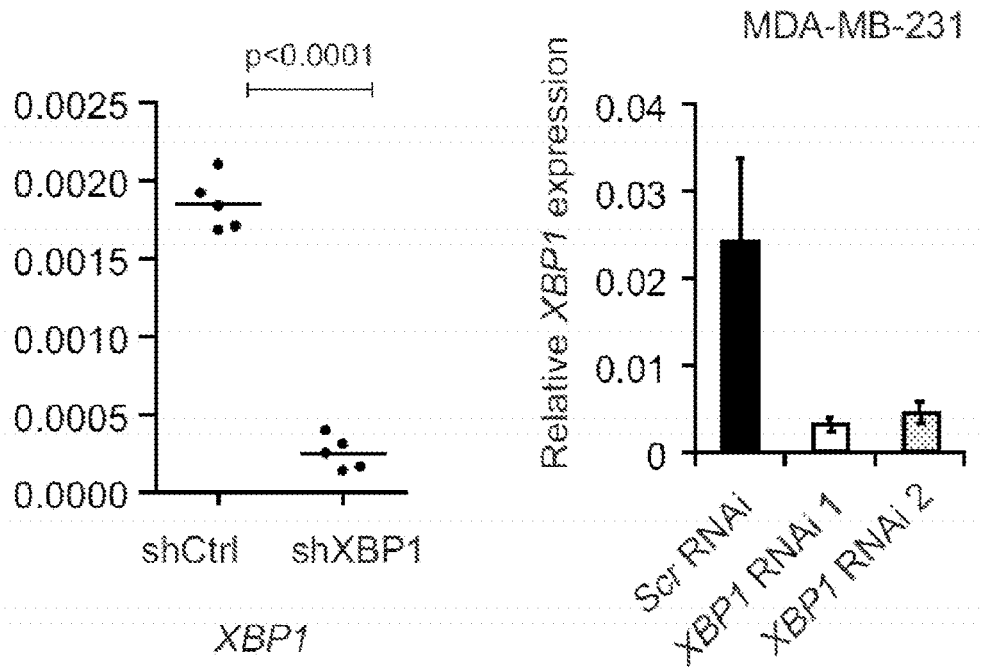
Fig. 3I
Fig. 3J

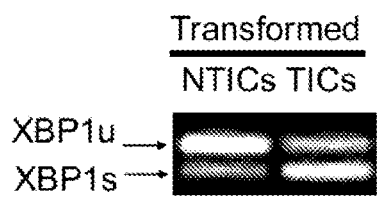
Fig. 4A
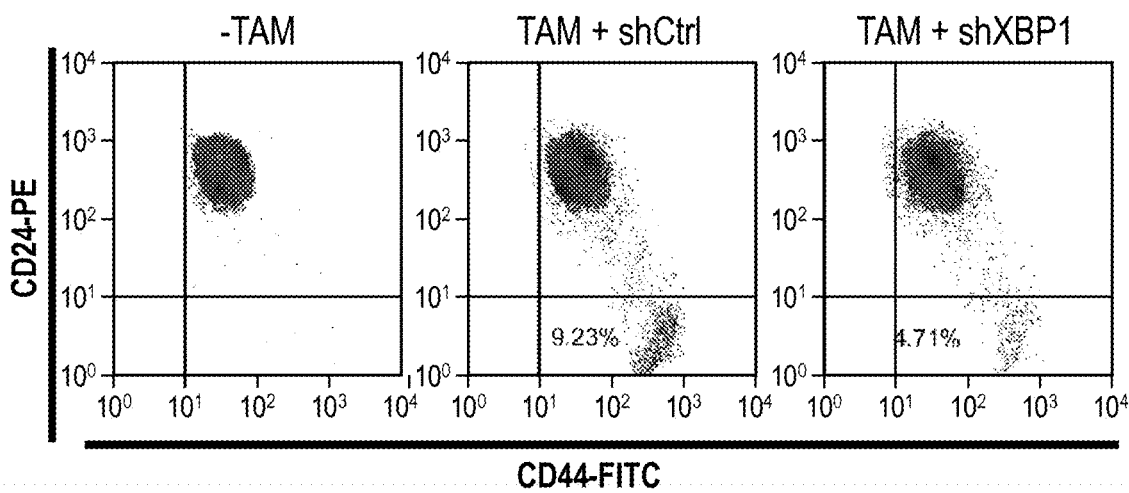
Fig. 4B
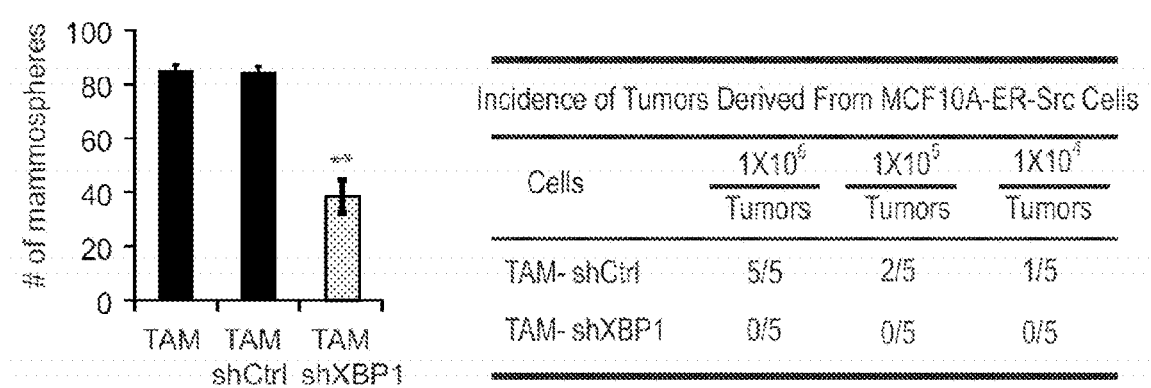
Fig. 4C          Fig. 4D

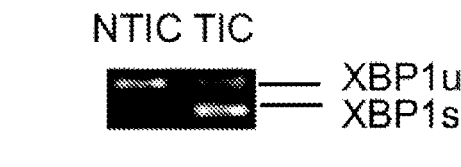
Br Ca1 TNBC Patient
*Fig. 4E*
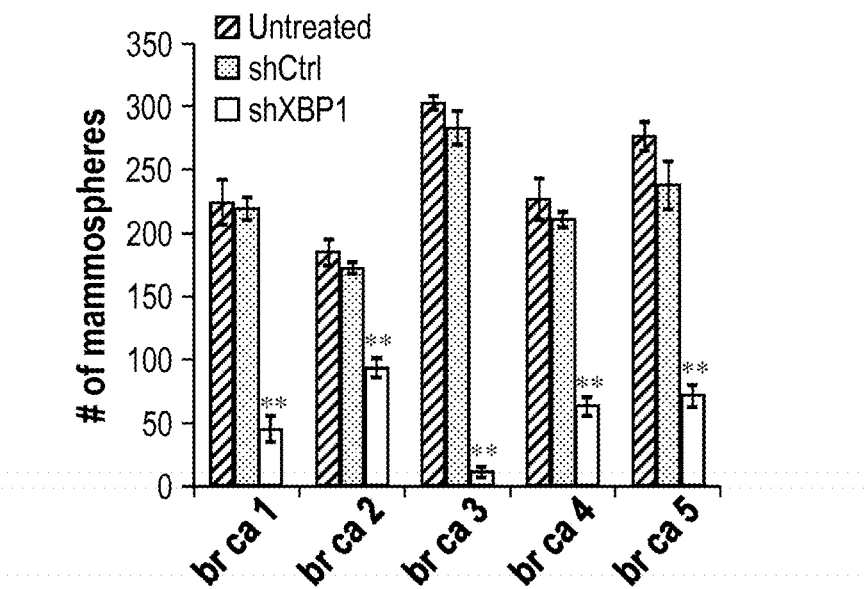
*Fig. 4F*
| Incidence of Tumors in NOD/SCID/IL2Rγ-/- mice | | | |
|---|---|---|---|
| Cell line | Purified cells | 10/Tumors | Weeks to first palpability |
| Br ca 1 | NTICs | 0/10 | 0 |
| | XBP1s-NTICs | 7/10 | 10 ± 2 |
| Br ca 2 | NTICs | 0/12 | 0 |
| | XBP1s-NTICs | 10/12 | 11 ± 2 |
*Fig. 4G*

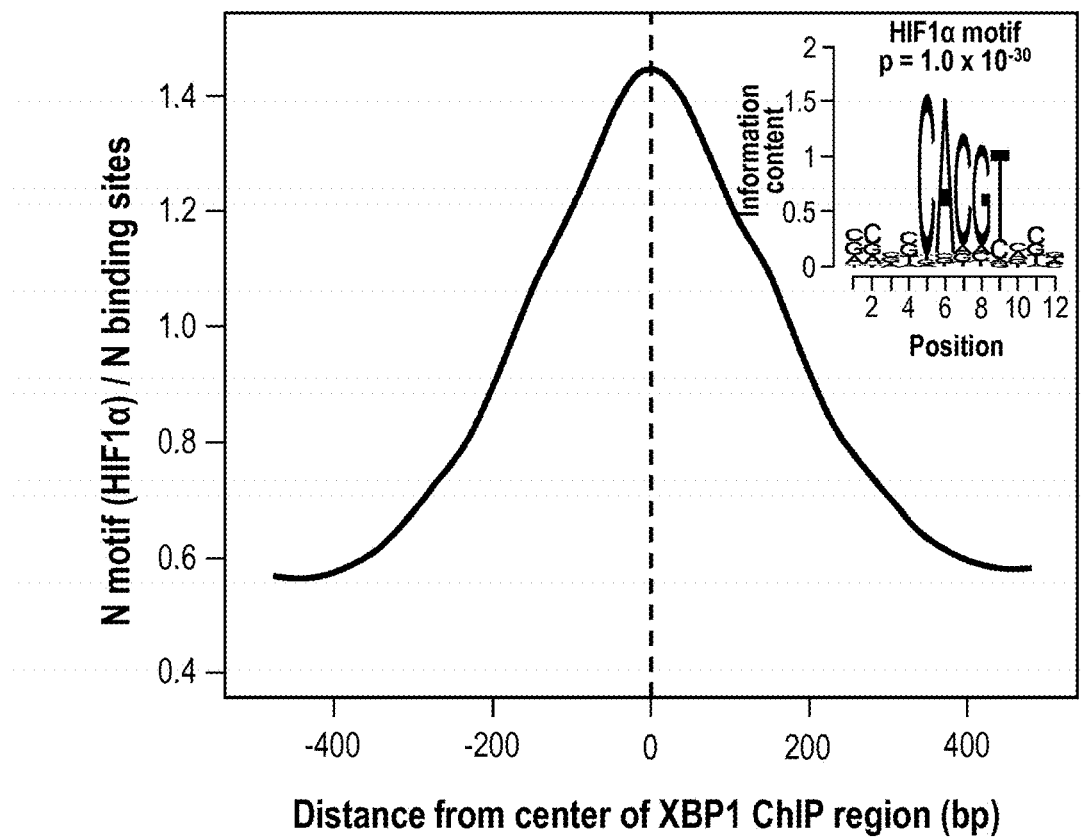
Fig. 5A
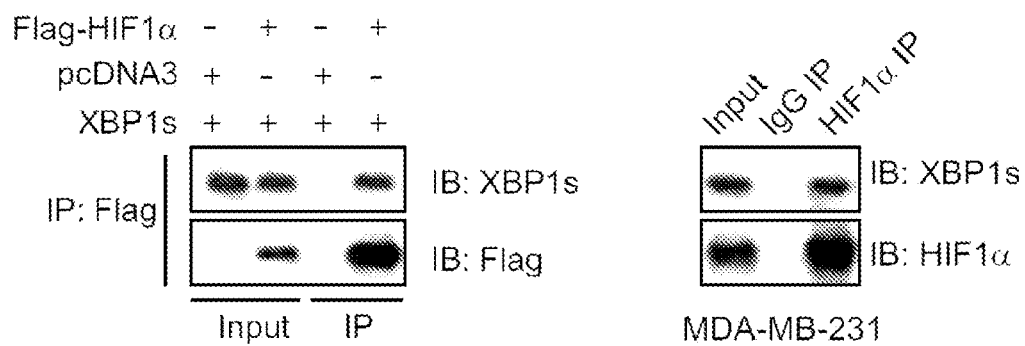
Fig. 5B  Fig. 5C

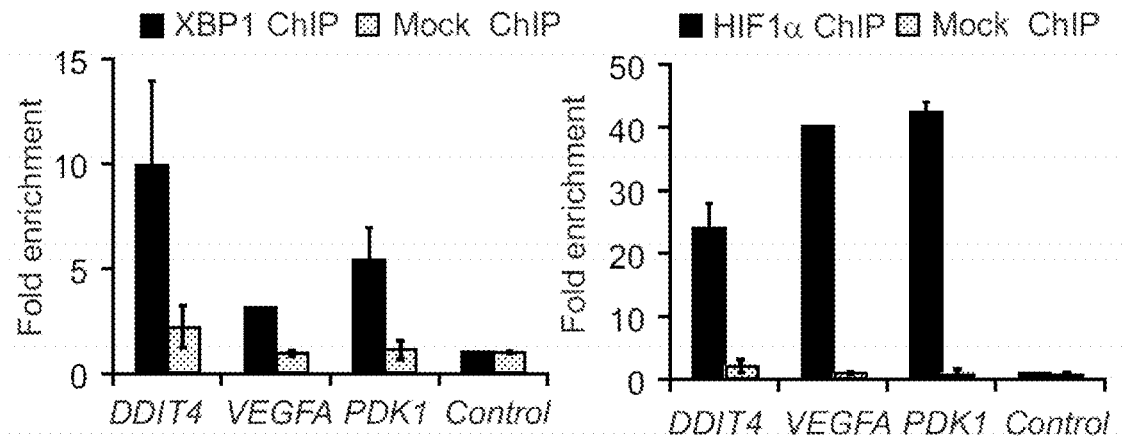
Fig. 5E  Fig. 5F
Fig. 5G
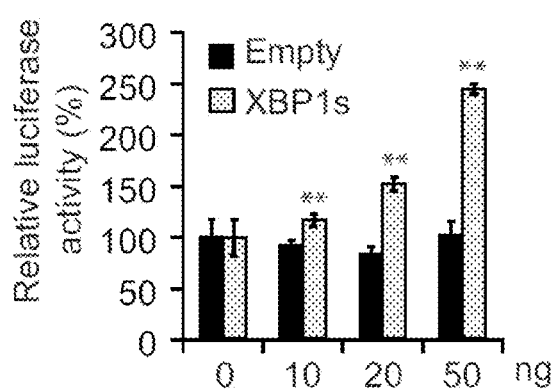  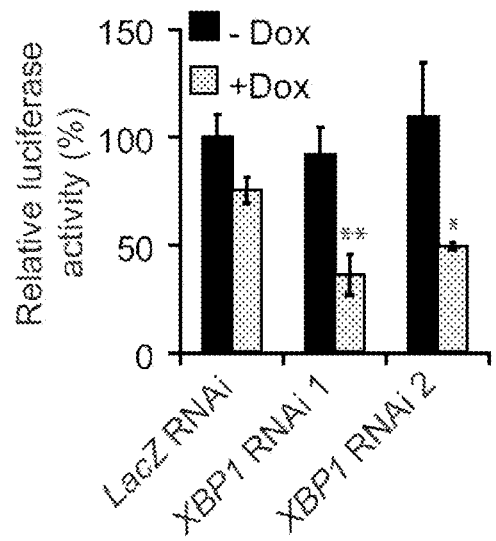
Fig. 5H  Fig. 5I

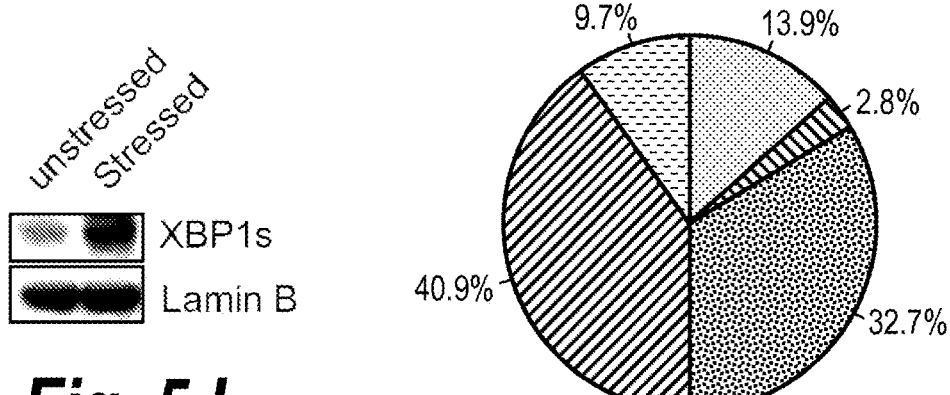
*Fig. 5J*
*Fig. 5K*
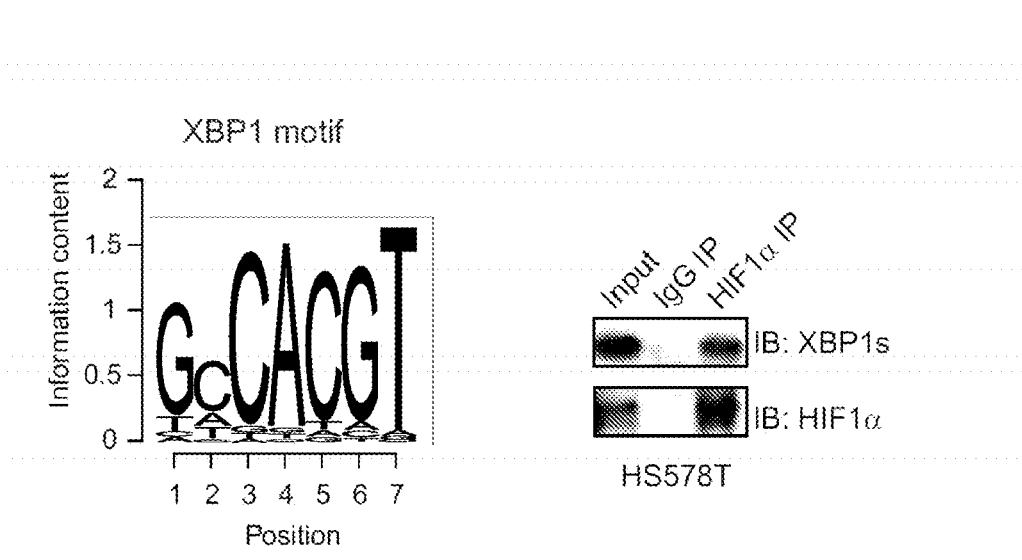
*Fig. 5L*
*Fig. 5M*

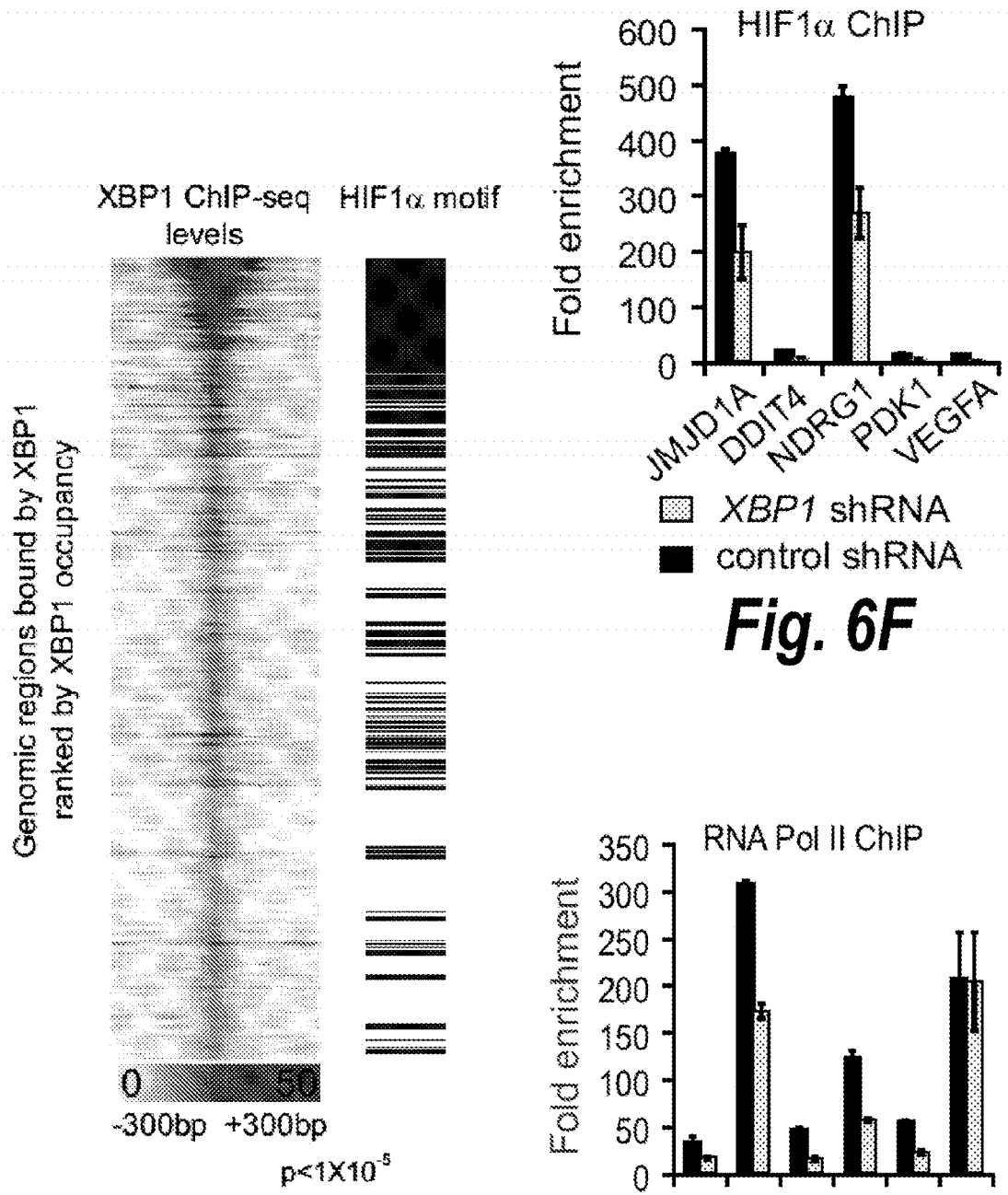

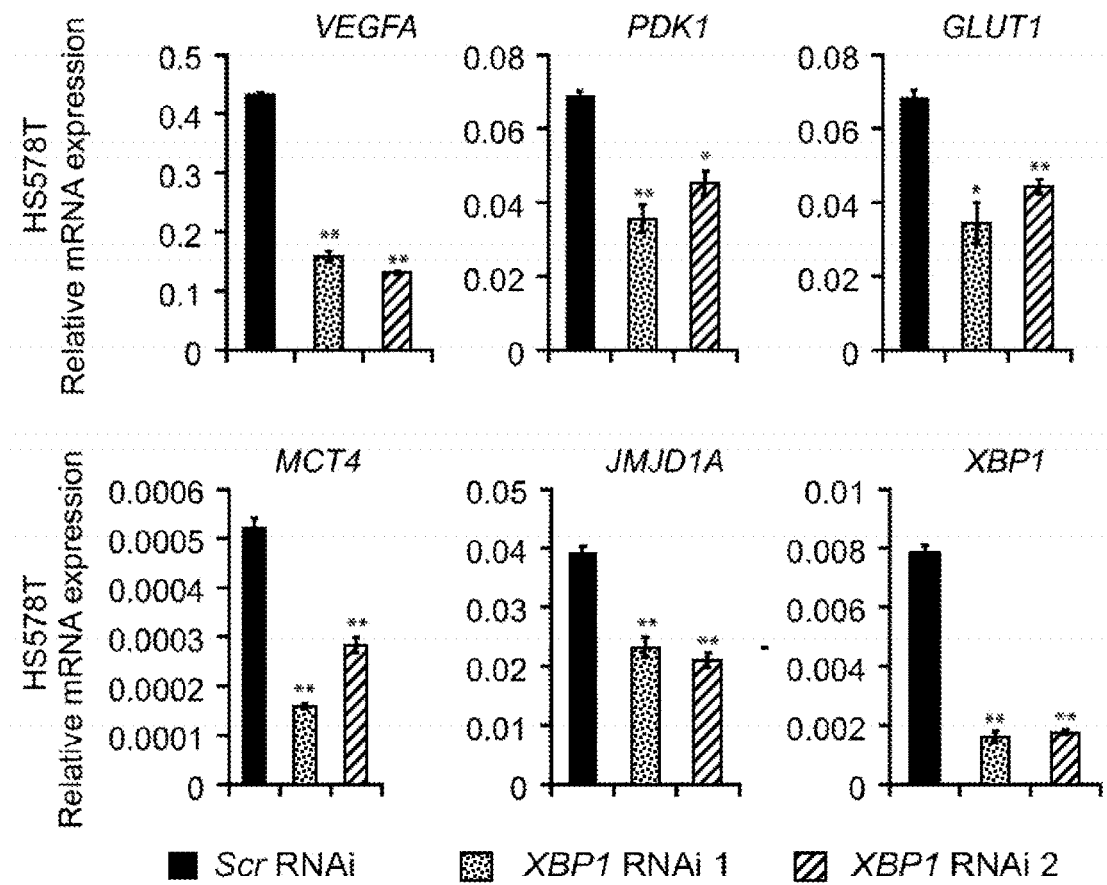
Fig. 6H
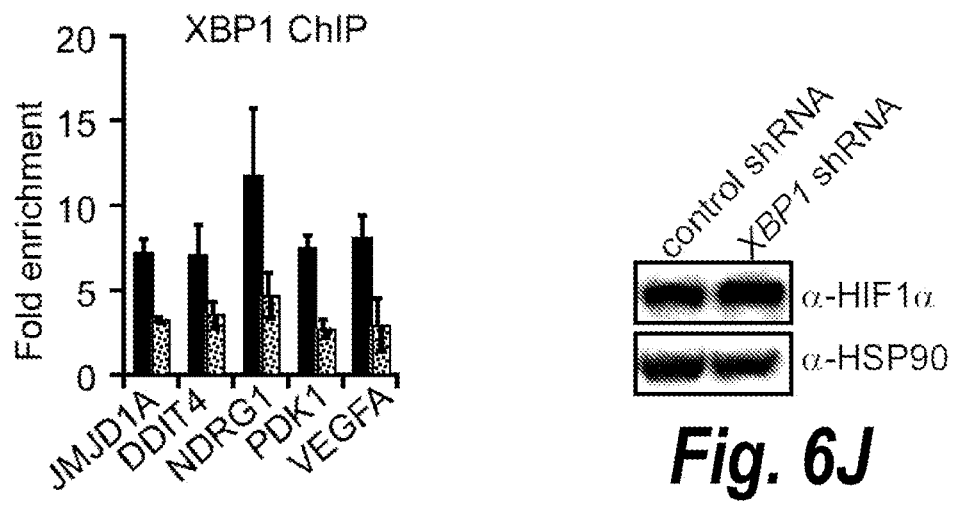
Fig. 6I
Fig. 6J

MODULATION OF BREAST CANCER GROWTH BY MODULATION OF XBP1 ACTIVITY

CROSS-REFERENCED TO RELATED APPLICATIONS

This Application is a Division of Application 14/383,687 filed on Sep. 8, 2014, now pending, which is a National Stage Entry of PCT Application No. PCT/US2013/030251, filed Mar. 11, 2013, which claims the benefit of U.S. Provisional Application 61/609,130 filed on Mar. 9, 2012. The entire contents of each of these applications are incorporated herein by reference in their entireties.

GOVERNMENT SUPPORT

This invention was made with government support under CA112663 and AI032412 awarded by National Institutes of Health. The government has certain rights in the invention.

BACKGROUND OF THE INVENTION

During tumor development and progression, cancer cells encounter cytotoxic conditions such as hypoxia, nutrient deprivation, and low pH due to inadequate vascularization (Hanahan, D., et al. 2011. Cell 144, 646-674). To maintain survival and growth in the face of these physiologic stressors, a set of adaptive response pathways are induced. One adaptive pathway well studied in other contexts is the unfolded protein response (UPR), which is induced by factors affecting the endoplasmic reticulum (ER) such as changes in glycosylation, redox status, glucose availability, calcium homeostasis or the accumulation of unfolded or misfolded proteins (Hetz, C., et al. 2001. Physiol Rev 91, 1219-1243). Notably, features of the tumor microenvironment, such as hypoxia and nutrient deprivation, can disrupt ER homeostasis by the perturbation of aerobic processes such as oligosaccharide modification, disulphide bond formation, isomerization, and protein quality control and export (Wouters, B. G., et al. 2008. Nat Rev Cancer 8, 851-864).

In mammalian cells, the UPR is mediated by three ER-localized transmembrane protein sensors: Inositol-requiring transmembrane kinase/endonuclease-1 (IRE1), PKR-like ER kinase (PERK) and activating transcription factor 6 (ATF6) (Walter, P., et al. 2011. Science 334, 1081-1086). Of these, IRE1 is the most evolutionarily conserved branch. An increase in the load of folding proteins in the ER activates IRE1, an ER-resident kinase and endoribonuclease that acts as an ER-stress sensor (Walter, P., et al. 2011. Science 334, 1081-1086). Activated IRE1 removes a 26 bp intron from XBP1 mRNA and results in a frame shift in the coding sequence, with the spliced form encoding a 226 amino acid transcriptional activation domain (Calfon, M., et al. 2002. Nature 415, 92-96; Yoshida, H., et al. 2001. Cell 107, 881-891). In contrast to the unspliced XBP1 (XBP1u), which is unstable and quickly degraded, spliced XBP1 (XBP1s) is stable and is a potent inducer of target genes that orchestrate the cellular response to ER stress (Hetz, C., et al. 2011. Physiol Rev 91, 1219-1243). XBP1 deficient mice display severe abnormalities in differentiation of several lineages of specialized secretory cells, including plasma cells (Reimold, A. M., et al. 2001. Nature 412, 300-307), exocrine pancreas cells (Lee, A. H., et al. 2005. EMBO J 24, 4368-4380) and intestinal epithelial cells (Kaser, A., et al. 2008. Cell 134, 743-756). As the mammary gland is a secretory tissue that undergoes extensive secretory compartment expansion during the transition from pregnancy to lactation, the function of XBP1 in the normal mammary gland and in breast cancer is of special interest. XBP1 expression was reported to be regulated by estrogen receptor and induced in primary human breast cancer (Fujimoto, T., et al. 2003. Breast Cancer 10, 301-306), however, the functional role of the UPR and XBP1 in the normal and malignant mammary gland is largely unknown.

SUMMARY OF THE INVENTION

The unfolded protein response (UPR) is essential for tumor cells to survive the pathologic stresses intrinsic to the tumor microenvironment. The instant invention is based, at least in part, on the new finding of an unexpected function of XBP1 (X box binding protein1), a key component of the UPR, in human triple negative breast cancer (TNBC). In particular, the instant inventors have discovered that XBP1 promotes TNBC and does so by controlling the hypoxia response. Triple negative breast cancer (TNBC) is a highly aggressive malignancy with limited treatment options and TNBC-targeted therapies do not yet exist. Here, it is reported that XBP1, a key component of the Unfolded Protein Response (UPR), is activated in TNBC and plays a pivotal role in the tumorigenicity and progression of this human breast cancer subtype. The instant inventors show that XBP1 is required for the transformation of immortalized mammary epithelial cells. Silencing of XBP1 significantly suppressed the growth and invasiveness of TNBCs. Activation of the XBP1 pathway is associated with poor prognosis in human TNBC patients. Intriguingly, XBP1 is preferentially activated in tumor initiating cells (TICs) and is essential for sustaining TIC self-renewal. Moreover, overexpression of the active form of XBP1 (XBP1s) in non-TICs is sufficient to confer stem-like or tumor-initiating properties on them, while depletion of XBP1 inhibited tumor relapse due to a preferential depletion of TICs (by reducing the population of chemotherapy-resistant TICs).

Genome-wide mapping of the XBP1 transcriptional regulatory network revealed that XBP1 regulates the hypoxia response through controlling HIF1α transcriptional activity and the expression of HIF1α targets. The instant inventors have identified a genetic fingerprint (gene expression signature) indicative of XBP1 pathway activation that is associated with poor prognosis in human TNBC patients. These findings, for the first time, reveal a key function for this branch of the UPR in TNBC (linking the UPR pathway with TNBC and TIC), opening new avenues for therapeutics for TNBC patients.

Figure 1A:
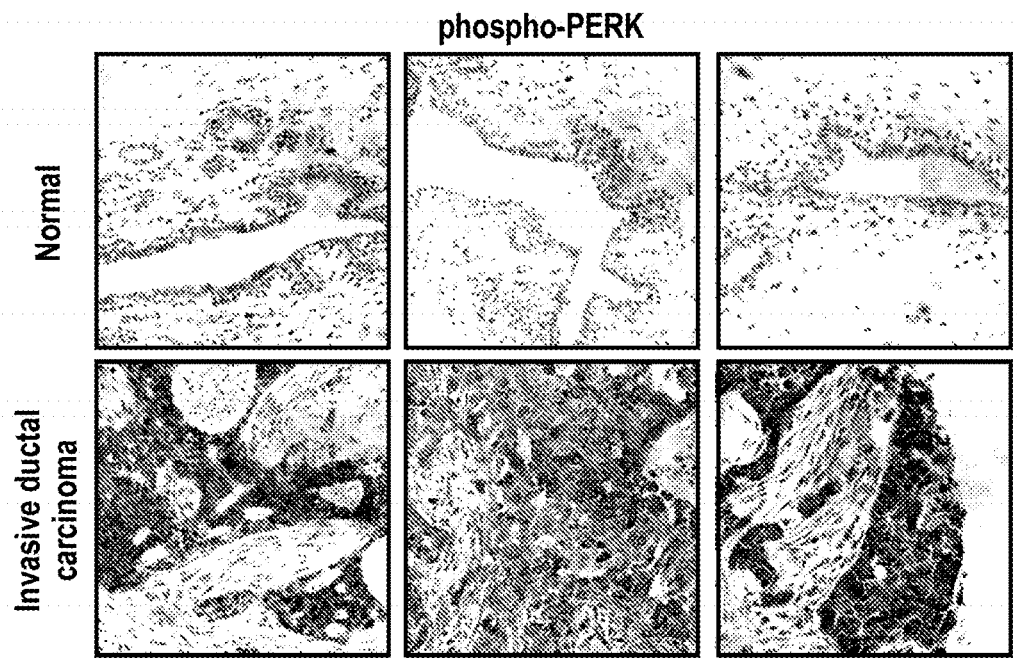
FIG. 1. The UPR is activated in human breast cancer.

(A) A TMA containing normal breast tissue or breast cancer tissue sections was subjected to IHC for phospho-PERK (Thr980) (DAB staining, brown). Representative pictures are shown from normal and human breast cancer tissues.

(B). Comparison of PERK phosphorylation in normal breast tissue samples and breast cancer samples. 66 normal human breast tissues and 40 human breast cancer tissues were evaluated.

(C) The TMA were subjected to IHC for phospho-EIF2α (Ser51) (DAB staining, brown). Representative pictures are shown from normal and human breast cancer tissues.

(D) Comparison of EIF2α phosphorylation in normal breast tissue samples and breast cancer samples. 59 normal human breast tissues and 41 human breast cancer tissues were evaluated.

FIG. 2. XBP1 is required for transformation of immortalized mammary epithelial cells (A) XBP1 silencing blocks the phenotypic transformation of MCF10A ER-Src cells. MCF10A ER-Src cells were infected with lentivirus encoding XBP1 shRNA (shXBP1) or control shRNA (shCtrl), and treated with tamoxifen (TAM) for 36 hr. Phase-contrast images are shown.

(B) Quantification of invasive cells in untreated and TAM-treated MCF10A ER-Src cells in the presence or absence of control or XBP1 shRNA.

(C) Quantification of soft agar colony formation in untreated and TAM-treated MCF10A ER-Src cells in the presence or absence of control or XBP1 shRNA. Experiments were performed in triplicate and data are shown as mean±SD.

(D) Tumor growth (mean±SD) of untreated, control shRNA, and XBP1 shRNA treated MCF10A ER-Src (TAM treated) cells. TX: treatment with shRNA.

(E) MCF10A ER-Src cells were infected with retrovirus encoding XBP1s or empty vector. Phase-contrast images are shown.

(F) Quantification of soft agar colonies in MCF10A ER-Src cells infected with empty vector or spliced XBP1 (XBP1s) expressing retroviruses. Phase-contrast images are shown in the lower panel.

All experiments were performed in triplicate and data are shown as mean±SD.

FIG. 3. XBP1 inhibition blocks breast cancer cell growth and invasiveness in vitro and in vivo.

(A) RT-PCR analysis of XBP1 splicing in different luminal and basal-like cell lines. XBP1u: unspliced XBP1, XBP1s: spliced XBP1.

(B) Quantification of soft agar colony formation in untreated and control shRNA or XBP1 shRNA infected breast cancer cells.

(C) Quantification of invasive cells in untreated and control shRNA or XBP1 shRNA infected breast cancer cells. **p,0.01

(D) Quantitative RT-PCR analysis of XBP1 expression in MDA-MB-231 cells infected with doxycycline (DOX) inducible lentiviruses encoding shRNAs against XBP1 or scrambled LACZ control, in the presence or absence of doxycycline for 48 h. Data are presented relative to β-actin. Experiments were performed in triplicate and data are shown as mean±SD.

(E) Representative bioluminescent images of orthotopic tumors formed by MDA-MB-231 cells as in (D) that were then superinfected with a retrovirus encoding firefly luciferase. A total of 1.5×10$^6$ cells were injected into the fourth mammary glands of NOD/SCID/IL2Rγ–/– mice. Bioluminescent images were obtained 5 days later and serially after mice were begun on chow containing doxycycline (day 19). Pictures shown are the day 19 image (Before Dox) and day 64 image (After Dox).

(F) Quantitation of imaging studies as in (E). *p<0.05. **p<0.01.

(G) Tumor incidence of TNBC patient-derived BCM-2147 tumor treated with scrambled siRNA (n=11) or XBP1 siRNA (n=9). Tumor incidence is reported at 10 weeks post-transplantation. Statistical significance was determined by Barnard's test. (Barnard, G. A., 1945. *Nature* 156, 177; Barnard, G. A., 1947. *Biometrika* 34, 123-138).

(H) Tumor growth (mean±SD) of BCM-2147 tumors as in (G). *p<0.05, **p<0.01.

Figure 3A:
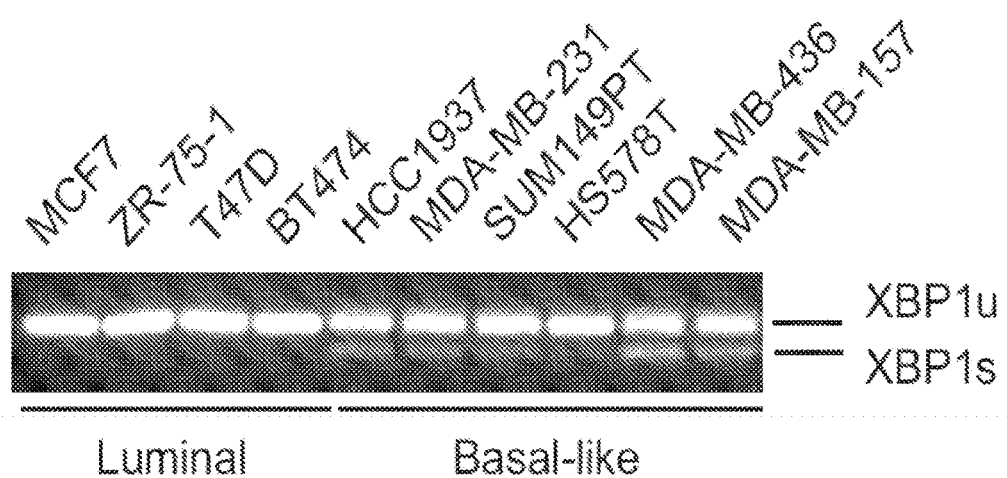
Figure 3B:
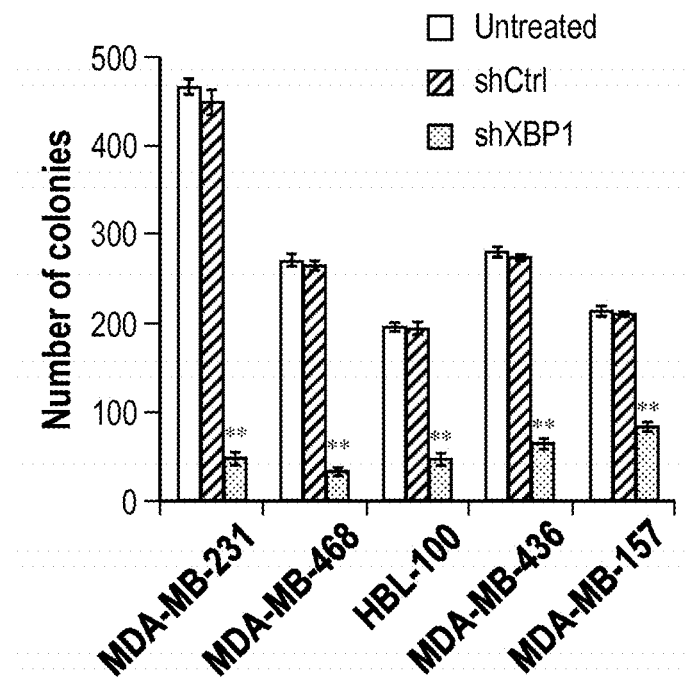
Figure 3C:
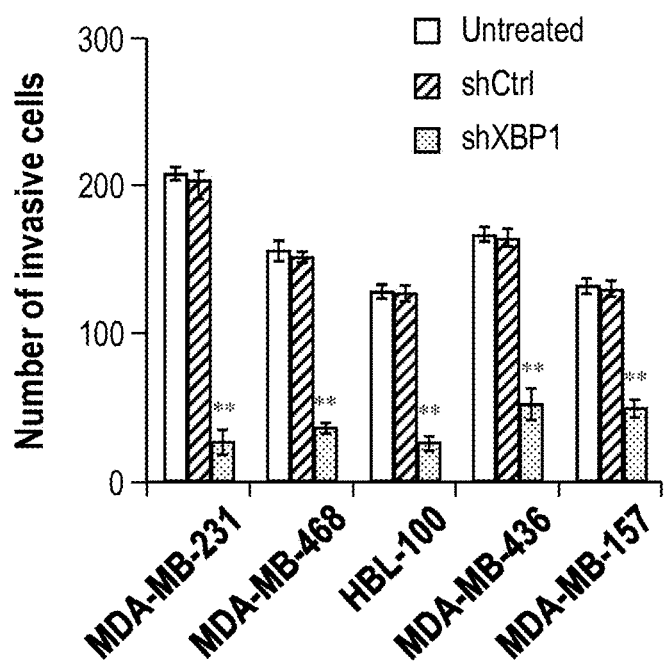
Figure 3D:
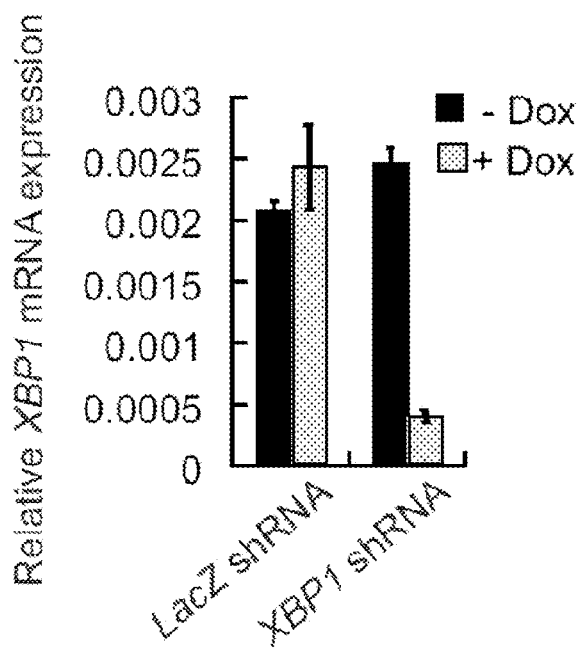
Figure 3E:
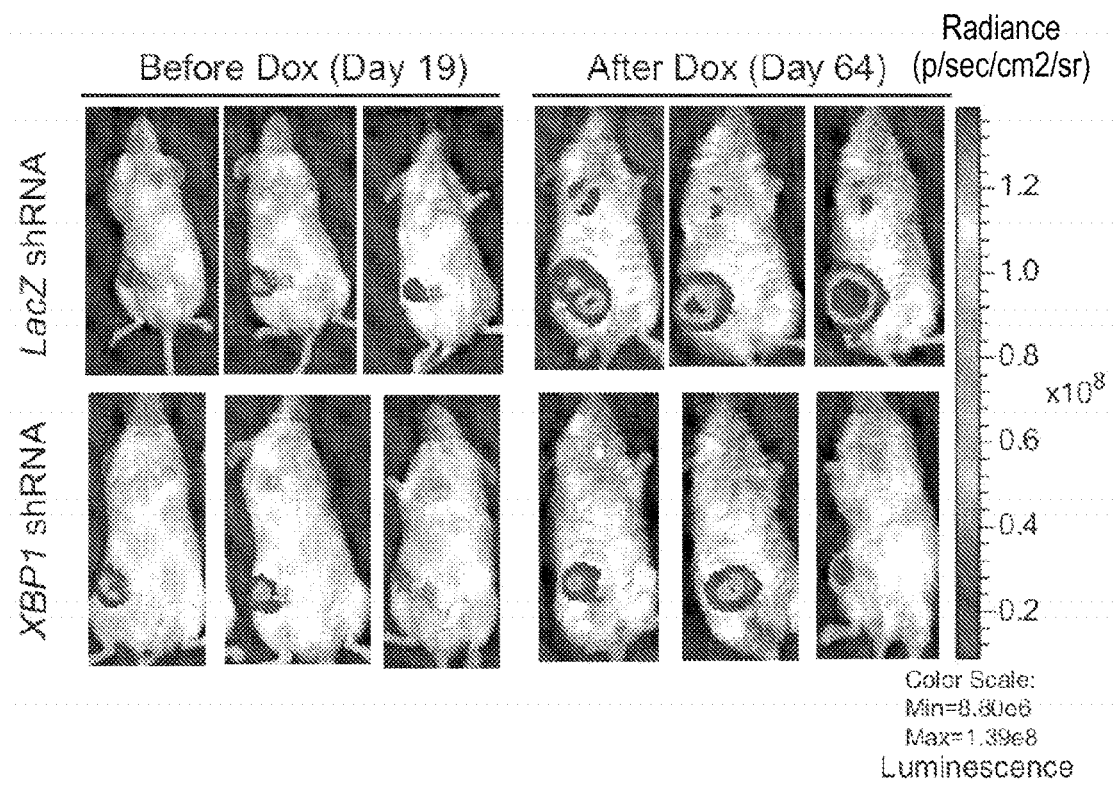

(I) Knockdown efficiency of XBP1 in MDA-MB-231 derived xenograft tumor (as in FIG. 3E). Quantitative RT-PCR analysis of XBP1 expression in shCtrl or shXBP1 xenograft tumor. Data are presented relative to β-actin. There are 5 mice in each group and data are shown as mean±SD.

(J) Knockdown efficiency of XBP1 in MDA-MB-231 cells with two shRNA constructs targeting different regions of XBP1.

(K) Bioluminescent images of orthotopic tumors formed by luciferase-expressing MDA-MB-231 cells infected with different lentiviruses. A total of 1.5×10 cells were injected into the fourth mammary glands of nude mice. Bioluminescent images were obtained 1 week later and serially after mice were begun on chow containing doxycycline (Dox) (day 10). Pictures shown are the day 10 images (Before Dox) and day 45 images (After Dox).

(L) Tumor growth (mean±SD) of untreated or control shRNA, and XBP1 shRNA treated MDA-MB-436 cells. *p<0.01.

(M) Tumor growth (mean±SD) of untreated or control shRNA, and XBP1 shRNA treated HBL-100 cells. **p<0.01. TX: treatment with shRNA.

FIG. 4. XBP1 is required to sustain cancer stem cell self-renewal (A) RT-PCR analysis of XBP1 splicing in untreated and TAM treated NTICs (CD4$^{low}$/CD24$^{high}$) and TICs (CD44$^{high}$/CD24$^{low}$). XBP1u: unspliced XBP1, XBP1s: spliced XBP1.

(B) Flow cytometry analyzing CD44 and CD24 expression of untreated and TAM treated (36 h) MCF10A ER-Src cells infected with control GFP shRNA or XBP1 shRNA encoding lentivirus.

(C) Number of mammospheres per 1,000 cells generated by TAM treated MCF10A ER-Src cells uninfected, or infected with control shRNA or XBP1 shRNA encoding lentivirus.

(D) The indicated number of TAM-treated MCF10A-ER-Src cells infected with control shRNA or XBP1 shRNA were injected into NOD/SCID/IL2Rα–/– mice and the tumor incidence was reported at 12 weeks post-transplantation.

(E) RT-PCR analysis of XBP1 splicing in NTICs and TICS purified from TNBC patient. XBP1u: unspliced XBP1, XBP1s: spliced XBP1.

(F) Number of mammospheres per 1,000 cells generated from untreated and control shRNA or XBP1 shRNA encoding lentivirus infected primary tissue samples from five patients with TNBC (G) 10 NTIC sorted from two human TNBC patients or NTIC overexpressing XBP1s were injected into NOD/SCID/IL2Rγ–/– mice and the incidence of tumors was monitored.

(H) Knockdown efficiency of XBP1 in MCF10A-ER-Src cells.

(I) Percentage of TICs (CD44high/CD24low) in TAM treated MCF10A-ER-Src cells infected with control shRNA or XBP1 shRNA encoding lentivirus.

(J) Cell viability assay (Cell-titer Glo) on TICs (CD44high/CD24low) isolated from transformed MCF10A-ER-Src cells infected with control shRNA or XBP1 shRNA encoding lentivirus (72 h after infection). Data were normalized to the control (cell infected with shCtrl). Experiments were performed in triplicate and data are shown as mean±SD.

(K) Cell viability assay (Cell-titer Glo) on NTICs (CD44low/CD24high). Data analysis is the same as (J).

(L) Tumor growth (mean±SD) of MDA-MB-231 cells untreated or treated with doxorubicin, or doxorubicin (dox)+ control shRNA, or doxorubicin+XBP1 shRNA. TX: treatment with Dox or Dox+shRNA.

(M) Number of mammospheres per 1,000 cells generated from day 20 xenograft tumors under different treatments as indicated. Data are shown as mean±SD.

FIG. 5. XBP1 interacts with HIF1α and co-occupies promoters of HIF1α target genes.

(A) Motif enrichment analysis in the XBP1 binding sites. The average HIF1α motif enrichment signal is shown for the 1 kb region surrounding the center of the XBP1 binding site.

(B) FLAG-tagged HIF1α and XBP1s were co-expressed in 293T cells and the cells were treated in 0.1% O2 for 16 h. Co-IP was performed with M2 anti-FLAG antibody. Western blot was carried out with anti-XBP1s antibody or anti-FLAG antibody. Empty vector was used as negative control.

(C) Nuclear extracts from MDA-MB-231 cells treated with TM (1 ug/ml, 6 h) in 0.1% O2 (16 h) were subjected to co-IP with anti-HIF1α antibody or rabbit IgG. Western blot was carried out with anti-XBP1s antibody or anti-HIF1α antibody.

(D-F) Schematic diagram of the primer locations across the JMJD1A promoter (D). XBP1 and HIF1α cobind to JMJD1A, DDIT4, VEGFA, and PDK1 promoters under hypoxic conditions. A ChIP assay was performed using anti-XBP1 polyclonal antibody (D-E) or anti-HIF1α polyclonal antibody (D, F) to detect enriched fragments. Fold enrichment is the relative abundance of DNA fragments at the amplified region over a control amplified region. GST antibody was used as mock ChIP control (D-F). Primer locations correspond to (D).

(G) Schematic of the luciferase reporter constructs containing three copies of HRE (3×HRE)

(H) 3×HRE reporter was co-transfected with XBP1s expression plasmid or empty vector into MDA-MB-231 cells and luciferase activity measured.

(I) 3×HRE reporter was co-transfected with doxycycline (DOX) inducible constructs encoding two shRNAs targeting different regions of XBP1 or scrambled LACZ control into MDA-MB-231 cells. Cells were treated in 0.1% O2 for 24 h in the presence or absence of doxycycline, and luciferase activity assayed. All luciferase activity was measured relative to the *renilla* luciferase internal control. Experiments were performed in triplicate and data are shown as mean±SD. *p<0.05, *'p<0.01.

(J) Western blotting analysis of XBP1s expression in nuclear extract of MDA-MB-231 cells cultured under unstressed or stressed condition (0.1% O2 and glucose deprivation) for 16 h. Lamin B was used as loading control.

(K) Distribution of XBP1 binding sites. Locations of XBP1 binding sites relative to the nearest tran transcription units. The percentages of binding sites at the respective locations are shown (L) Identification of XBP1 motif in ChIP-seq. Matrices predicted by the de novo motif-discovery algorithm Seqpos. $p=1\times10^{-30}$.

(M) Nuclear extracts from Hs578T cells treated with TM (1 ug/ml, 6 h) in 0.1% O2 (16 h) were subjected to co-IP with anti-HIF1α antibody or rabbit IgG. Western blot was carried out with anti-XBP1s antibody or anti-HIF1α antibody.

(N) XBP1 and HIF1α co-bind to the JMJD2C promoter under hypoxic conditions.

FIG. 6. XBP1 regulates the hypoxia response.

(A) Plot from GSEA showing enrichment of the HIF1α mediated hypoxia response pathway in XBP1-upreuglated genes.

(B) Gene expression microarray heatmap showing that genes involved in the HIF1α mediated hypoxia responses were differentially expressed after XBP1 knockdown.

(C-D) Quantitative RT-PCR analysis of VEGFA, PDK1, GLUT1, JMJD1A and DDIT4 expression after knockdown of XBP1 in MDA-MB-231 under hypoxic conditions (C) or MDA-MB-231 derived xenograft tumors (d, n=5). Results are presented relative to β-actin expression. Experiments were performed in triplicate and data are shown as mean±SD. *p<0.05, **p<0.01.

(E) Plot showing the genome-wide association between the strength of the XBP1 binding and the occurrence of the HIF1α motif. The signal of XBP1 ChIP-seq peaks was shown as a heatmap using red (the strongest signal) and white (the weakest signal) color scheme. Each row shows ±300 bp centered on the XBP1 ChIP-seq peak summits. Rows are ranked by XBP1 occupancy. The horizontal blue lines denote the presence of the HIF1α motif.

(F-G) Chromatin extracts from control MDA-MB-231 cells or XBP1 knockdown MDA-MB-231 cells (treated with 0.1% $O_2$ for 24 h) were subjected to ChIP using anti-HIF1α antibody (F), and anti-RNA polymerase II antibody (G). The primers used to detect ChIP-enriched DNA in (F-G) were the peak pair of primers in JMJD1A, DDIT4, NDRG1, PDK1 and VEGFA promoters (Table 2). Primers in the β-actin region/promoter were used as control. Data are presented as the mean±SD.

(H) Quantitative RT-PCR analysis of VEGFA, PDK1, GLUT1, MCT4, JMJD1A and XBP1 expression after knockdown of XBP1 in Hs578T cells treated with 0.1% O2 for 24 h. Results are presented relative to β-actin expression. Experiments were performed in triplicate and data are shown as mean±SD. *p<0.05, **p<0.01.

(I) Chromatin extracts from control MDA-MB-231 cells or XBP1 knockdown MDA-MB-231 cells (treated with 0.1% O2 for 24 h) were subjected to ChIP using anti-XBP1s antibody. Data are presented as the mean±SD.

(J) Immunoblotting analysis of control MDA-MB-231 cell lysates and XBP1 knockdown lysates (treated with 0.1% O2 for 24 h) were performed using anti-HIF1α or anti-HSP90 antibody.

FIG. 7. XBP1 genetic signature is associated with human breast cancer prognosis.

(A) Heatmap showing the expression profile of genes bound by XBP1 and differentially expressed after XBP1 knockdown (B-C) Kaplan-Meier graphs demonstrating a significant association elevated expression of the XBP1 signature with shorter relapse-free survival in two cohorts of triple negative breast cancer patients (B and C). The log-rank test P values are shown.

(D). Kaplan-Meier graphs showing the significant association of expression of HIF1α gene signature with shorter relapse-free survival in a cohort of 383 TNBC patients. The log-rank test P values are shown.

DETAILED DESCRIPTION OF THE INVENTION

The unfolded protein response (UPR) is essential for tumor cells to survive the pathologic stresses intrinsic to the tumor microenvironment. Here, it is reported an unexpected function of XBP1 (X box binding protein1), a key component of the UPR, in human triple negative breast cancer (TNBC). It is shown that XBP1 is required for the transformation of immortalized mammary epithelial cells. Silencing of XBP1 significantly suppressed the growth and invasiveness of TNBCs. Activation of the XBP1 pathway is associated with poor prognosis in human TNBC patients. Intriguingly, XBP1 is preferentially activated in tumor initiating cells (TICs) and is essential for sustaining TIC self-renewal. Moreover, overexpression of the active form of XBP1 in non-TICs is sufficient to confer stem-like properties on them, while depletion of XBP1 inhibited tumor relapse due to a preferential depletion of TICs. Genome-wide mapping of the XBP1 transcriptional regulatory network revealed that XBP1 regulates the hypoxia response through controlling HIF1α transcriptional activity and the expression of HIF1α targets. The instant inventors have identified a genetic fingerprint indicative of XBP1 pathway activation that is associated with poor prognosis in human TNBC patients. These findings, for the first time, link the UPR pathway with TNBC and TIC, opening new avenues for therapeutics for TNBC patients.

Accordingly, in one aspect, the invention pertains to a method of inhibiting growth of triple negative breast cancer (TNBC) in a subject, the method comprising administering to the subject a direct or indirect inhibitor of XBP1 such that growth of the TNBC in the subject is inhibited. Non-limiting examples of direct inhibitors of XBP1 include a nucleic acid molecule that is antisense to an XBP1-encoding nucleic acid molecule, an XBP1 shRNA, an XBP siRNA, a microRNA that targets XBP1, a dominant negative XBP1 molecule and small molecule inhibitors of XBP1. Non-limiting examples of indirect inhibitors of XBP1 include agents that target IRE1, an endonuclease essential for proper splicing and activation of XBP1, such that inhibition of IRE1 leads to inhibition of the production of the spliced, active form of XBP1. Non-limiting examples of IRE1 inhibitors include a nucleic acid molecule that is antisense to an IRE1-encoding nucleic acid molecule, an IRE1 shRNA, an IRE1 siRNA, a microRNA that targets IRE1, a dominant negative IRE1 molecule and small molecule inhibitors of IRE1.

In another aspect, the invention pertains to a method of identifying a compound useful in inhibiting the growth of triple negative breast cancer (TNBC) cells, the method comprising:

a) providing an indicator composition comprising XBP1 and HIF1α, or biologically active portions thereof;

b) contacting the indicator composition with each member of a library of test compounds;

c) selecting from the library of test compounds a compound of interest that decreases the interaction of XBP1 and HIF1α, or biologically active portions thereof, wherein the ability of a compound to inhibit growth of TNBC cells is indicated by a decrease in the interaction as compared to the amount of interaction in the absence of the compound.

The indicator composition can be, for example, a cell-free preparation comprising XBP1 and HIF1α, or biologically active portions thereof (e.g., isolated recombinant proteins), or a cell comprising XBP1 and HIF1α, or biologically active portions thereof (e.g., a recombinant cell transfected to express XBP1 and HIF1α proteins). The read-out for the method to determine the amount of interaction between XBP1 and HIF1α can be, for example, a direct read-out that measures the amount of binding between XBP1 and HIF1α (e.g., one or both proteins can be labeled or tagged), such as co-immunoprecipitation, or an indirect read-out that measures the amount of transcriptional activity of the XBP1/HIF1α complex, such as use of a reporter gene responsive to the XBP1/HIF1α complex and measurement of the level of the reporter.

In yet another aspect, the invention pertains to a method for determining a prognosis status for a subject with triple negative breast cancer (TNBC), the method comprising:

a) determining an XBP1 gene signature for the TNBC of the subject; and b) correlating the XBP1 gene signature with a prognosis status for the subject, wherein higher expression of the XBP1 gene signature, relative to a control, correlates with shorter relapse-free survival of the subject and lower expression of the XBP1 gene signature, relative to a control, correlates with longer relapse-free survival of the subject.

The XBP1 gene signature can comprise, for example, a plurality of genes regulated by XBP1 in TNBC, such as a plurality of genes selected from the 133 genes shown in Table 1.

The contents of all references, patents, and published patent applications cited throughout this application, as well as the figures and the sequence listing, are hereby incorporated by reference.

Various aspects of the invention are described in further detail in the following subsections:

I. XBP1 and Triple Negative Breast Cancer

During tumor development and progression, cancer cells encounter cytotoxic conditions such as hypoxia, nutrient deprivation, and low pH due to inadequate vascularization (Hanahan, D., et al. 2011. *Cell* 144, 646-74). To maintain survival and growth in the face of these physiologic stressors, a set of adaptive response pathways are induced. One adaptive pathway well studied in other contexts is the unfolded protein response (UPR), which is induced by factors affecting the endoplasmic reticulum (ER) such as changes in glycosylation, redox status, glucose availability, calcium homeostasis or the accumulation of unfolded or misfolded proteins (Hetz, C., et al. 2011. *Physiol Rev*, 91, 1219-43). Notably, features of the tumor microenvironment, such as hypoxia and nutrient deprivation, can disrupt ER homeostasis by the perturbation of aerobic processes such as oligosaccharide modification, disulphide bond formation, isomerization, and protein quality control and export (Wouters, B. G., et al. 2008. *Nat Rev Cancer* 8, 851-64). In mammalian cells, the UPR is mediated by three ER-localized transmembrane protein sensors: Inositol-requiring transmembrane kinase/endonuclease-1 (IRE1), PKR-like ER kinase (PERK) and activating transcription factor 6 (ATF6) (Walter, P., et al. 2011. *Science* 334, 1081-6). Of these, IRE1 is the most evolutionarily conserved branch. An increase in the load of folding proteins in the ER activates IRE1, an ER-resident kinase and endoribonuclease that acts as an ER-stress sensor4. Activated IRE1 removes a 26 bp intron from XBP1 mRNA and results in a frame shift in the coding sequence, with the spliced form encoding a 226 amino acid transcriptional activation domain (Calfon, M., et al. 2002. *Nature* 415, 92-6; Yoshida, H., et al. 2001. *Cell* 107, 881-91). In contrast to the unspliced XBP1 (XBP1u), which is unstable and quickly degraded, spliced XBP1 (XBP1s) is stable and is a potent inducer of target genes that orchestrate the cellular response to ER stress (Hetz, C., et al. 2011. *Physiol Rev* 91, 1219-43). Several studies have reported on the activation of the UPR in various human tumors and its relevance to combinatorial therapy (Ma, Y., et al. 2004. *Nat Rev Cancer* 4, 966-77; De Raedt, T., et al. 2011. *Cancer Cell* 20, 400-13; Mahoney, D. J., et al. 2011. *Cancer Cell* 20, 443-56; Healy, S. J., et al. 2009. *Ear J Pharmacol* 625, 234-46; Carrasco, D. R., et al. 2007. *Cancer*

Cell 11, 349-60). However, the role of the UPR and XBP1 in the malignant mammary cell is largely unknown.

As described in detail above, the UPR is a major cellular stress response pathway activated in tumors that allows them to adapt to the stresses of the tumor microenvironment. Several studies have reported on the activation of the UPR in various human tumors and its relevance to combinatorial therapy (Carrasco, D. R., et al. 2007. *Cancer Cell* 11, 349-36; De Raedt, T., et al. 2011. *Cancer Cell* 20, 400-413; Healy, S. J., et al. 2009. *Eur J Pharmacol* 625, 234-246; Ma, Y., et al. 2004. *Nat Rev Cancer* 4, 966-977; Mahoney, D. J., et al. 2011. *Cancer Cell* 20, 443-456). However, the role of the UPR in breast cancer pathogenesis remains elusive. Here, the instant inventors have identified a previously unknown function of XBP1 in triple-negative breast cancer (TNBC). It is demonstrated that XBP1 is spliced and activated in TNBC, and that deletion of XBP1 significantly blocks triple negative breast tumor growth. Here, it is demonstrates that XBP1, a key component of the most evolutionarily conserved branch of the UPR, is essential for the transformation of mammary epithelial cells and is preferentially activated in tumor initiating cells (TICs) where it is essential for sustaining TIC self-renewal. Furthermore, XBP1 silencing suppressed tumor relapse along with depleting the breast tumor initiating cells (TICs). Genome-wide mapping of the XBP1 transcriptional regulatory network identified its key downstream target to be the hypoxia response via the transcription factor hypoxia-inducible factor 1 α (HIF1α). XBP1 regulates HIF1α transcriptional activity by controlling HIF1α binding to promoter DNA and by the recruitment of RNA polymerase 11. We generated a genetic fingerprint indicative of XBP1 pathway activation that we found to be associated with poor prognosis in human TNBC patients. Moreover, activation of the hypoxia response pathway appears to carry prognostic implications, as expression of the XBP1-dependent signature is associated with shorter survival times in patients with TNBC.

XBP1 was reported to be highly expressed in ER+ breast tumors and to activate ERα in a ligand-independent manner (Ding, L., et al. 2003. *Nucleic Acids Res* 31, 5266-5274; Fujimoto, T., et al. 2003. *Breast Cancer* 10, 301-306). Splicing of XBP1 confers estrogen independence and antiestrogen resistance to breast cancer cell lines (Gomez, B. P., et al. 2007. *Faseb J* 21, 4013-4027). Here, by manipulating the expression of XBP1 in a panel of breast cancer cell lines and in a human xenograft model, we discovered a key function for XBP1 in TNBC. TNBC is a subtype of breast tumors characterized by a of the absence of expression of ER, PR and HER2, signaling receptors known to fuel most breast cancers. TNBC is extremely aggressive and more likely to recur and metastasize than the other subtypes (Foulkes, W. D., et al. 2010. *N Engl J Med* 363, 1938-1948). While ER+, PR+ or Her2 tumors respond well to ER antagonist, aromatase inhibitor, or Her2-targeted therapies, TNBC is unresponsive to most receptor targeted treatments. TNBC is a highly heterogeneous group of cancers, the genes linked to TNBC are not well understood and thus, targeted therapies do not yet exist. We found that XBP1 was preferentially activated in TNBC cells, and that silencing of XBP1 was very effective in suppressing the tumorigenicity and progression of TNBCs.

A TNBC

Triple-negative breast cancer (TNBC) refers to any breast cancer that does not express the genes for estrogen receptor (ER), progesterone receptor (PR) or Her2/neu. Triple negative is sometimes used as a surrogate term for basal-like; however, more detailed classification may provide better guidance for treatment and better estimates for prognosis. (Hudis, C. A., et al. 2011. *The Oncologist* 16, 1-11). Triple-negative breast cancer (TNBC) is breast cancer characterized by malignant tumors. As used herein, the term "malignant" refers to a non-benign tumor or a cancer. In one embodiment a malignancy expands to other parts of the body as well (metastasizes). A malignant tumor is usually life-threatening, causing death if it remains untreated. If treated, the spread of a malignant tumor can be slowed or even arrested. Depending on the amount of tissue damage prior to treatment, tissue or organ function can be compromised.

Triple negative breast cancers have a relapse pattern that is very different from hormone-positive breast cancers: the risk of relapse is much higher for the first 3-5 years but drops sharply and substantially below that of hormone-positive breast cancers after that. This relapse pattern has been recognized for all types of triple negative cancers for which sufficient data exists although the absolute relapse and survival rates differ across subtypes. (Hudis, C. A., et al. 2011. *The Oncologist* 16, 1-11; Cheang, M. C. U., et al. 2008. *Clinical Cancer Research* 14 (5), 1368-1376).

Triple-negative breast cancers are sometimes classified into "basal-type" and other cancers; however, there is no standard classification scheme. Basal type cancers are frequently defined by cytokeratin 5/6 and EGFR staining. However no clear criteria or cutoff values have been standardized yet. (Hudis, C. A., et al. (2011). *The Oncologist* 16, 1-11). About 75% of basal-type breast cancers are triple negative. Some TNBC overexpresses epidermal growth factor receptor (EGFR). Some TNBC over expresses transmembrane glycoprotein NMB (GPNMB). On histologic examination triple negative breast tumors mostly fall into the categories secretory carcinoma or adenoid cystic types (both considered less aggressive), medullary cancers and grade 3 invasive ductal carcinomas with no specific subtype, and highly aggressive metastatic cancers. (Hudis, C. A. et al. 2011. *The Oncologist* 16, 1-11). Medullary TNBC in younger women are frequently BRCAJ-related. Rare forms of triple negative breast cancer are apocrine and squamous carcinoma. Inflammatory breast cancer is also frequently triple negative.

B. UPR

The term "Unfolded Protein Response" (UPR) or the "Unfolded Protein Response pathway" refers to an adaptive response to the accumulation of unfolded proteins in the ER and includes the transcriptional activation of genes encoding chaperones and folding catalysts and protein degrading complexes as well as translational attenuation to limit further accumulation of unfolded proteins. Both surface and secreted proteins are synthesized in the endoplasmic reticulum (ER) where they need to fold and assemble prior to being transported.

Since the ER and the nucleus are located in separate compartments of the cell, the unfolded protein signal must be sensed in the lumen of the ER and transferred across the ER membrane and be received by the transcription machinery in the nucleus. The unfolded protein response (UPR) performs this function for the cell. Activation of the UPR can be caused by treatment of cells with reducing agents like DTT, by inhibitors of core glycosylation like tunicamycin or by Ca-ionophores that deplete the ER calcium stores. First discovered in yeast, the UPR has now been described in *C. elegans* as well as in mammalian cells. In mammals, the UPR signal cascade is mediated by three types of ER transmembrane proteins: the protein-kinase and site-specific endoribonuclease IRE-1; the eukaryotic translation initiation factor 2 kinase, PERK/PEK; and the transcriptional activator ATF6. If the UPR cannot adapt to the presence of unfolded proteins in the ER, an apoptotic response is initiated leading to the activation of JNK protein kinase and caspases 7, 12, and 3. The most proximal signal from the lumen of the ER is received by a transmembrane endoribonuclease and kinase called IRE-1. Following ER stress, IRE-1 is essential for survival because it initiates splicing of the XBP-1 mRNA the spliced version of which, as shown herein, activates the UPR.

C. XBP1

The term "XBP-1" refers to a X-box binding human protein that is a DNA binding protein and has an amino acid sequence as described in, for example, Liou, H. C., et. al. 1990. Science 247, 1581-1584 and Yoshimura, T., et al. 1990. EMBO J. 9, 2537-2542, and other mammalian homologs thereof, such as described in Kishimoto T., et al. 1996. Biochem. Biophys. Res. Commun. 223, 746-751 (rat homologue). Exemplary proteins intended to be encompassed by the term "XBP-1" include those having amino acid sequences disclosed in GenBank with accession numbers A36299 [gi:105867], NP_005071 [gi:4827058], P17861 [gi:139787], CAA39149 [gi:287645], and BAA82600 [gi:5596360] or e.g., encoded by nucleic acid molecules such as those disclosed in GenBank with accession numbers AF027963 [gi: 13752783]; NM_013842 [gi: 13775155]; or M31627 [gi:184485]. XBP-1 is also referred to in the art as TREB5 or HTF (Yoshimura, T., et al. 1990. EMBO Journal. 9, 2537; Matsuzaki, Y., et al. 1995. J. Biochem. 117, 303). Like other members of the b-zip family. XBP-1 has a basic region that mediates DNA-binding and an adjacent leucine zipper structure that mediates protein dimerization.

As described above, there are two forms of XBP-1 protein, unspliced and spliced, which differ markedly in their sequence and activity. Unless the form is referred to explicitly herein, the term "XBP-1" as used herein includes both the spliced and unspliced forms. Spliced XBP-1 ("XBP1s") directly controls the activation of the UPR, while unspliced XBP-1 functions due to its ability to negatively regulate spliced XBP-1.

As used herein, the term "spliced XBP-1" ("XBP1s") refers to the spliced, processed form of the mammalian XBP-1 mRNA or the corresponding protein. Human and murine XBP-1 mRNA contain an open reading frame (ORF1) encoding bZIP proteins of 261 and 267 amino acids, respectively. Both mRNA's also contain another ORF, ORF2, partially overlapping but not in frame with ORF1. ORF2 encodes 222 amino acids in both human and murine cells. Human and murine ORF1 and ORF2 in the XBP-1 mRNA share 75% and 89% identity respectively.

As used herein, the term "unspliced XBP-1" refers to the unprocessed XBP-1 mRNA or the corresponding protein. As set forth above, unspliced murine XBP-1 is 267 amino acids in length and spliced murine XBP-1 is 371 amino acids in length. The sequence of unspliced XBP-1 is known in the art and can be found, e.g., Liou. H. C., et. al. 1990. Science 247, 1581-1584 and Yoshimura, T., et al. 1990. EMBO J. 9, 2537-2542, or at GenBank accession numbers NM_005080 [gi:14110394] or NM_013842 [gi:13775155].

II. XBP1 and Tumor Initiating Cells

TNBC typically contain a higher proportion of "stem-like" breast cancer cells, also known as tumor initiating cells (TICs), characterized by a CD4$^+$CD24$^{-/low}$ surface phenotype of and the expression of aldehyde dehydrogenase 1 (Al-Hajj, M., et al. 2003. Proc Natl Acad Sci USA 100, 3983-3988; Ginestier, C., et al. 2007. Cell Stem Cell 1, 555-567). TICs resemble stem cells, as they are capable of both indefinite self-renewal and differentiation. Relative to NTICs. TICs contribute to a significantly higher incidence of recurrence and distant metastasis, and are responsible for tumor initiation and maintenance (Smalley, M., et al. 2003. Nat Rev Cancer 3, 832-844; Stingl, J., et al. 2007. Nat Rev Cancer 7, 791-799). Although conventional therapies have shown great promise in killing the bulk of differentiated tumor cells, TICs are resistant to chemotherapy (Stingl, J., et al. 2007. Nat Rev Cancer 7, 791-799). The development of effective therapies targeting the TIC is urgently needed to treat breast cancer metastasis and relapse. Although several self-renewal regulatory pathways including the Notch, Wnt and Hedgehog pathways (Visvader, J. E., et al. 2008. Nat Rev Cancer 8, 755-768), as well as microenvironmental stress, such as hypoxia (Keith, B., et al. 2007. Cell 129, 465-472; Schwab, L. P., et al. 2012. Breast Cancer Res 14, R6), are known to be essential in promoting a stem-like phenotype, progress in targeting TICs with novel therapeutics is still hindered by our incomplete knowledge of the molecular pathways contributing to TIC identity.

Here we have demonstrated that XBP1 is essential for the self-renewal of breast TICs. In support of this claim, we showed that XBP1 was selectively activated in TICs, XBP1 inhibition blocked the formation of TICs, and depletion of XBP1 greatly suppressed the growth of mammospheres derived from human TNBC patients and various breast cancer cell lines, a key measure of TIC function. Overexpression of XBP1s in non-TICs conferred stem-like traits and tumorigenic potential at very low dilutions (10 cells). Finally, XBP1 depletion in combination with chemotherapy blocked xenograft tumor growth and relapse, which was attributed to the decreased TIC population after combinatorial treatment. Ours is the first study to demonstrate that compromising the ER stress response significantly impairs TIC growth and self-renewal. We speculate that the rapid proliferation of TICs requires robust ER protein folding, assembly, and transport, functions which rely on XBP1 activation and which are compromised in its absence. XBP1 serves as one of the major cellular adaptive mechanisms activated to protect TICs in a non-dividing dormant state, and XBP1 confers on TICs growth and survival advantages over non-TICs. The specific acquisition of XBP1 activation in TICs is intriguing and provides new insights into pathways that may be used to target this subpopulation of cancer cells.

III. XBP1 Regulates the Hypoxia Response Through HIF1α

Hypoxia is known to promote aggressive tumor phenotypes. A growing body of evidence indicates that hypoxia is required for TIC survival and tumor propagation in glioma, lymphoma and acute myeloid leukemia (Heddleston, J. M., et al. 2009. Br J Cancer 102, 789-795; Jogi, A., et al. 2002. Proc Natl Acad Sci USA 99, 7021-7026; Li., Z., et al. 2009. Cancer Cell 15, 501-513; Wang, Y., et al. 2011. Cell Stem Cell 8, 399-411). HIF transcription factors are crucial to the maintenance of the undifferentiated state of stem cells residing in hypoxic niches. TNBCs also display increased levels of hypoxia (Rakha, E. A., et al. 2009. Clin Cancer Res 15, 2302-2310; Tan, E. Y., et al. 2009. Br J Cancer 100, 405-411) and HIF1α was recently demonstrated to be essential for their maintenance of breast TICs. HIF1α promotes expansion of breast TICs in vivo, and deletion of HIF1α results in reduced mammosphere formation, primary breast tumor growth and pulmonary metastases in the MMTV-PyVT breast cancer mouse model (Schwab. L. P., et al. 2012. Breast Cancer Res 14, R6). Increased HIF1α levels are also associated with increased metastasis and decreased survival in patients with breast cancer (Bos, R., et al. 2003. *Cancer* 97, 1573-1581; Semenza, C. L., 2010. *Cell* 107, 1-3).

Our data reveal that XBP1 acts in breast TICs and TNBC through regulating the response to hypoxia. HIF1α requires XBP1 to sustain downstream target expression under hypoxic conditions. XBP1 interacts with HIF1α to co-occupy a set of, if not all, HIF1α targets. Depletion of XBP1 leads to reduction in classic HIF1α targets expression and HRE activity by blocking HIF1α binding to its target genes, which subsequently affects the recruitment of RNA polymerase II to target promoters. Hypoxia is a physiological inducer of the UPR in cancer (Wouters, B. G., et al. 2008. *Nat Rev Cancer* 8, 851-864). In this study, we found that XBP1 functions in a positive feedback loop to sustain the hypoxia response via regulating HIF1α transcriptional activity. This feed-forward circuit ensures maximum HIF activity and an efficient adaptive response to the cytotoxic microenvironment of solid tumors. HIF activity is tightly controlled during tumor progression, through translational and post-translational regulation of HIF1α but relatively little is known about how HIF1α transcriptional activity is controlled (Kaelin, W. G., Jr., et al. 2008. *Mol Cell* 30, 393-402). Our study reveals an unexpected function for XBP1 as a HIF1α transcriptional cofactor. We propose a model in which these two critical pathways, the UPR and the hypoxia response, are physically interconnected and act together to mount an appropriate adaptive response that promotes the survival of TICs in the hostile tumor microenvironment IV. Therapeutic Targeting of the UPR in TNBC We have highlighted the importance of the IRE1/XBP1 pathway in TNBC growth and metastasis, in part through regulating TICs. XBP1s expression is directly correlated with poor patient survival in human TNBC patients. Strikingly, while XBP1 is selectively activated in rapidly growing TICs, UPR pathways remain in a quiescent state in most normal unstressed cells. Hence inhibition of the UPR may offer a means to exclusively target tumor cells.

XBP1 is a transcription factor, and traditionally transcription factors other than hormone receptors have been difficult to target with small molecules. However, the upstream kinase and endoribonuclease IRE1, which drives the splicing of XBP1 mRNA, is a viable drug target. Recently, two groups have identified specific IRE1 endoribonuclease inhibitors (Papandreou, I., et al. 2011. *Blood* 117, 1311-1314; Volkmann, K., et al. 2011. *J Biol Chem* 286, 12743-12755). Intriguingly, these compounds efficiently inhibit XBP1 splicing in vivo and dramatically impair tumor growth in a xenograft model (Mahoney, D. J., et al. 2011. *Cancer Cell* 20, 443-456; Papandreou, I., et al. 2011. *Blood* 117, 1311-1314; Volkmann, K., et al. 2011. *J Biol Chem* 286, 12743-12755). While large-scale small molecule screens have provided potentially promising candidates that target the IRE1/XBP1 pathway, attention needs to be paid to the specificity and cytotoxicity of these compounds in vivo. Recent advances in solving the crystal structure of IRE1 (Korennykh, A. V., et al. 2009. *Nature* 457, 687-693; Lee, K. P., et al. 2008. *Cell* 132, 89-100; Zhou, J., et al. 2006. *Proc Natl Acad Sci USA* 103, 14343-14348) should accelerate the design of more potent and specific IRE1 inhibitors. The use of UPR inhibitors in combination with standard chemotherapy may greatly enhance the effectiveness of anti-tumor therapies.

The methods of the invention using inhibitory compounds which inhibit the expression, processing, post-translational modification, or activity of spliced XBP-1 or a molecule in a biological pathway involving XBP-1 can be used in the treatment of TNBC. In one embodiment of the invention, an inhibitory compound can be used to inhibit (e.g., specifically inhibit) the expression, processing, post-translational modification, or activity of spliced XBP-1. In another embodiment, an inhibitory compound can be used to inhibit (e.g., specifically inhibit) the expression, processing, post-translational modification, or activity of unspliced XBP-1.

Inhibitory compounds of the invention can be, for example, intracellular binding molecules that act to specifically or directly inhibit the expression, processing, post-translational modification, or activity e.g., of XBP-1 or a molecule in a biological pathway involving XBP-1 (e.g., HIF1α). As used herein, the term "intracellular binding molecule" is intended to include molecules that act intracellularly to inhibit the processing expression or activity of a protein by binding to the protein or to a nucleic acid (e.g., an mRNA molecule) that encodes the protein. Examples of intracellular binding molecules, described in further detail below, include antisense nucleic acids, intracellular antibodies, peptidic compounds that inhibit the interaction of XBP-1 or a molecule in a biological pathway involving XBP-1 and a target molecule (e.g., HIF1α), and chemical agents that specifically or directly inhibit XBP-1 activity or the activity of a molecule in a biological pathway involving XBP-1 (e.g., HIF1α).

In one embodiment, an inhibitory compound of the invention is an antisense nucleic acid molecule that is complementary to a gene encoding XBP-1 or a molecule in a signal transduction pathway involving XBP-1, e.g., a molecule with which XBP-1 interacts), or to a portion of said gene, or a recombinant expression vector encoding said antisense nucleic acid molecule. The use of antisense nucleic acids to downregulate the expression of a particular protein in a cell is well known in the art (see e.g., Weintraub, H., et al. 1986. *Reviews—Trends in Genetics*, Vol. 1(1); Askari, F. K., et al. 1996. *N. Eng. Med.* 334, 316-318; Bennett, M. R., et al. 1995. *Circulation* 92, 1981-1993; Mercola, D., et al. 1995. *Cancer Gene Mer.* 2, 47-59; Rossi, J. J., 1995. *Br. Med. Bull.* 51, 217-225; Wagner. R. W., 1994. *Nature* 372, 333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA. Given the known nucleotide sequence for the coding strand of the XBP-1 gene and thus the known sequence of the XBP-1 mRNA, antisense nucleic acids of the invention can be designed according to the rules of Watson and Crick base pairing. For example, the antisense oligonucleotide can be complementary to the region surrounding the translation start site of an XBP-1 An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. To inhibit expression in cells, one or more antisense oligonucleotides can be used.

Alternatively, an anti sense nucleic acid can be produced biologically using an expression vector into which all or a portion of a cDNA has been subcloned in an antisense orientation (i.e., nucleic acid transcribed from the inserted nucleic acid will be of an antisense orientation to a target nucleic acid of interest). The antisense expression vector can be in the form of, for example, a recombinant plasmid, phagemid or attenuated virus. The antisense expression vector can be introduced into cells using a standard transfection technique.

The antisense nucleic acid molecules of the invention are typically administered to a subject or generated in situ such that they hybridize with or bind to cellular mRNA and/or genomic DNA encoding a protein to thereby inhibit expression of the protein, e.g., by inhibiting transcription and/or translation. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein.

In yet another embodiment, an antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gautier, C., et al. 1987. *Nucleic Acids. Res.* 15, 6625-6641). The antisense nucleic acid molecule can also comprise a 2'-o-methylribonucleotide (Inoue, H., et al. 1987. *Nucleic Acids Res.* 15, 6131-6148) or a chimeric RNA-DNA analogue (Inoue, H., et al. 1987. *FEBS Lett.* 215, 327-330).

In still another embodiment, an antisense nucleic acid molecule of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff, J., et al. 1988. *Nature* 334, 585-591)) can be used to catalytically cleave mRNA transcripts to thereby inhibit translation mRNAs. Alternatively, gene expression can be inhibited by targeting nucleotide sequences complementary to the regulatory region of a gene (e.g., an XBP-1 promoter and/or enhancer) to form triple helical structures that prevent transcription of a gene in target cells. See generally, Helene, C., 1991. *Anticancer Drug Des.* 6(6), 569-84; Helene, C., et al. 1992. *Ann. N.Y. Acad. Sci.* 660, 27-36; and Maher, L. J., 1992. *Bioassays* 14(12), 807-15.

In another embodiment, a compound that promotes RNAi can be used to inhibit expression of XBP-1 or a molecule in a biological pathway involving XBP-1. The term "RNA interference" or "RNAi", as used herein, refers generally to a sequence-specific or selective process by which a target molecule (e.g., a target gene, protein or RNA) is downregulated. In specific embodiments, the process of "RNA interference" or "RNAi" features degradation of RNA molecules, e.g., RNA molecules within a cell, said degradation being triggered by an RNA agent. Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes. RNA interference (RNAi is a post-transcriptional, targeted gene-silencing technique that uses double-stranded RNA (dsRNA) to degrade messenger RNA (mRNA) containing the same sequence as the dsRNA (Sharp, P. A., et al. 2000. *Science* 287, 5462:2431-3.; Zamore, P. D., et al. 2000. *Cell* 101, 25-33. Tuschl, T., et al. 1999. *Genes Dev.* 13, 3191-3197; Cottrell T. R., et al. 2003. *Trends Microbiol.* 11, 37-43; Bushman F., 2003. *Mol Therapy* 7, 9-10; McManus M. T., et al. 2002. *Nat Rev Genet* 3, 737-47). The process occurs when an endogenous ribonuclease cleaves the longer dsRNA into shorter, e.g., 21-23-nucleotide-long RNAs, termed small interfering RNAs or siRNAs. As used herein, the term "small interfering RNA" ("siRNA") (also referred to in the art as "short interfering RNAs") refers to an RNA agent, preferably a double-stranded agent, of about 10-50 nucleotides in length (the term "nucleotides" including nucleotide analogs), preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof). The smaller RNA segments then mediate the degradation of the target mRNA. Kits for synthesis of RNAi are commercially available from, e.g. New England Biolabsor Ambion. In one embodiment one or more of the chemistries described above for use in antisense RNA can be employed in molecules that mediate RNAi.

Alternatively, compound that promotes RNAi can be expressed in a cell, e.g., a cell in a subject, to inhibit expression of XBP-1 or a molecule in a biological pathway involving XBP-1. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway. The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. shRNAs may be substrates for the enzyme Dicer, and the products of Dicer cleavage may participate in RNAi. shRNAs may be derived from transcription of an endogenous gene encoding a shRNA, or may be derived from transcription of an exogenous gene introduced into a cell or organism on a vector, e.g., a plasmid vector or a viral vector. An exogenous gene encoding an shRNA can additionally be introduced into a cell or organism using other methods known in the art, e.g., lipofection, nucleofection, etc.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides.

In certain embodiments, shRNAs of the invention include the sequences of a desired siRNA molecule described supra. In such embodiments, shRNA precursors include in the duplex stem the 21-23 or so nucleotide sequences of the siRNA, desired to be produced in vivo.

Another type of inhibitory compound that can be used to inhibit the expression and/or activity of XBP-1 or a molecule in a biological pathway involving XBP-1 (e.g., HIFα1 is an intracellular antibody specific for said protein. The use of intracellular antibodies to inhibit protein function in a cell is known in the art (see e.g., Carlson, J. R., 1988. *Mol. Cell. Biol.* 8, 2638-2646; Biocca, S., et al. 1990. *EMBO. J.* 9, 101-108; Werge, T. M., et al. 1990. *FEBS Letters* 274, 193-198; Carlson, J. R., 1993. *Proc. Natl. Acad. Sci. USA* 90, 7427-7428; Marasco, W. A., et al. 1993. *Proc. Natl. Acad. Sci. USA* 90, 7889-7893; Biocca, S., et al. 1994. *Bio/Technology* 12, 396-399; Chen, S. Y., et al. 1994. *Human Gene Therapy* 5, 595-601; Duan, L., et al. 1994. *Proc. Natl. Acad. Sci. USA* 91, 5075-5079; Chen, S. Y., et al. 1994. *Proc. Natl. Acad. Sci. USA* 91, 5932-5936; Beerli, R. R., et al. 1994. *J. Biol. Chem.* 269, 23931-23936; Beerli, R. R., et al. 1994. *Biochem. Biophys. Res. Commun.* 204, 666-672; Mhashilkar, A. M., et al. 1995. *EMBO J.* 14, 1542-1551; Richardson, J. H., et al. 1995. *Proc. Natl. Acad. Sci. USA* 92, 3137-3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of transcription factor activity according to the methods of the invention (e.g., inhibition of HIFα1, preferably an intracellular antibody that specifically binds the protein is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g., Biocca. S., et al. 1990. *EMBO J.* 9, 101-108; Mhashilkar, A. M., et al. 1995. *EMBO. J.* 14, 1542-1551). A preferred nuclear localization signal to be used for nuclear targeting of the intracellular antibody chains is the nuclear localization signal of SV40 Large T antigen (see Biocca, S., et al. 1990. *EMBO J.* 9, 101-108; Mhashilkar, A. M., et al. 1995. *EMBO J.* 14, 1542-1551).

In another embodiment, an inhibitory compound of the invention is a peptidic compound derived from the XBP-1 amino acid sequence or the amino acid sequence of a molecule in a biologicalon pathway involving XBP-1 (e.g., HIFα1). For example, in one embodiment, the inhibitory compound comprises a portion of, e.g., XBP-1 or HIFα1 (or a mimetic thereof) that mediates interaction of XBP-1, for example, with HIF1α such that contact of XBP-1 or HIF1α with this peptidic compound competitively inhibits the interaction of XBP-1 and HIF1α.

The peptidic compounds of the invention can be made intracellularly in cells by introducing into the cells an expression vector encoding the peptide. Such expression vectors can be made by standard techniques using oligonucleotides that encode the amino acid sequence of the peptidic compound. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g., liposome and the like).

In addition, dominant negative proteins (e.g., of XBP-1 or HIF1α) can be made which include XBP-1 or HIF1α molecules (e.g., portions or variants thereof) that compete with native (i.e., wild-type) molecules, but which do not have the same biological activity. Such molecules effectively decrease, e.g., XBP-1 or HIF1α activity in a cell.

Other inhibitory agents that can be used to specifically inhibit the activity of an XBP-1 or a molecule in a biological pathway involving XBP-1 are chemical compounds that directly inhibit expression, processing, post-translational modification, and/or activity of, e.g., an XBP-1 (or HIF1α) or inhibit the interaction between, e.g., XBP-1 and HIF1α. Such compounds can be identified using screening assays that select for such compounds, as described in detail above as well as using other art recognized techniques.

In exemplary embodiments, one or more of the above-described inhibitory compounds is formulated according to standard pharmaceutical protocols to produce a pharmaceutical composition for therapeutic use. A pharmaceutical composition of the invention is formulated to be compatible with its intended route of administration.

V. Prognostic Uses

Triple negative breast cancers comprise a very heterogeneous group of cancers. There is conflicting information over prognosis for the various subtypes but it is believed that, at least for more aggressive subtypes, present method of prognosis are poor. It is characterized by distinct molecular, histological and clinical features including a particularly unfavorable prognosis despite increased sensitivity to standard cytotoxic chemotherapy regimens.

The present invention is based, at least in part on the discovery of a gene expression signature indicative of XBP pathway activation that is associated with poor prognosis in patients with TNBC. As used herein, the term "gene expression signature" refers to a specific pattern of detectable signals indicative of gene expression in a sample. In one embodiment, the detectable signals are nucleic acid hybridization signals, for example, signals generated by hybridization of mRNAs in the sample to mRNA nucleic acid probes, e.g. probes having sequence complementarity to the mRNAs. Exemplary detectable labels include, but are not limited to, radioactive labels, fluorescent labels probes, colorometric labels, biotin labels, etc. Probes and/or mRNAs can be immobilized, for example, on a chip, membrane, slide, film, etc. In other embodiments, hybridization can be accomplished with one or more components in solution. In exemplary aspects of the invention, a "gene expression signature" consists of a plurality of signals of varied intensity, the pattern of which is reproducible when detected in replicate samples. In preferred aspects of the invention, a "gene expression signature" consists of a plurality of signals of increased intensity, for example, genes exhibiting increased expression in a TNBC sample or cell. In other aspects of the invention, a "gene expression signature"

consists of a plurality of signals of decreased intensity, for example, genes exhibiting decreased expression in a TNBC sample or cell. In still other aspects of the invention, a "gene expression signature" consists of a plurality of signals of increased and decreased intensity, for example, genes exhibiting increased and decreased expression in a TNBC sample or cell.

In exemplary embodiments of the invention, a "gene expression signature" is detected in a test sample (e.g., a biological sample from a patient suspected of having or at risk for developing TNBC, and compared to an appropriate control gene expression signature profile (e.g., a signature from a known TNBC sample or cell). In preferred embodiments, the "test sample" is a sample isolated, obtained or derived from a subject, e.g., a human subject. The term "subject" is intended to include living organisms but preferred subjects are mammals, and in particular, humans. In particularly preferred embodiments, the "test sample" is a sample isolated, obtained or derived from a female subject, e.g., a female human.

In some embodiments, the gene expression signature is associated with a specific stage of TNBC. In some embodiments, the gene expression signature features or consists essentially of mRNAs that are coordinately regulated. These mRNAs may be coordinately regulated, for example, by HIF1α transcriptional activity and can comprise or consist of specific HIF1α targets, i.e., genes expressed as a result of HIF1α transcriptional activity.

In preferred embodiments, a gene expression profiling test is used to analyze the patterns of a plurality of genes, e.g., those set forth in Table 1 within a sample from a TNBC subject, e.g., within a sample of cells from a breast tissue tumor in said subject or from another sample of cancer cells from said subject to help predict how likely it is that breast cancer, e.g., an early-stage breast cancer will recur after initial treatment.

In exemplary embodiments, the invention features diagnostic tests that quantify the likelihood of disease recurrence in subjects, e.g., women subjects with triple-negative breast cancer (TNBC). Such likelihood of disease recurrence is referred to herein as "prognostic significance". In referred embodiments, the diagnostic tests of the invention further assess the likely benefit from certain types of cancer therapeutics, e.g., chemotherapy. Such assessment is referred to herein as "predictive significance".

In exemplary aspects of the invention, the diagnostic tests are designed or formatted to analyzes a panel genes within a sample from a TNBC subject, e.g., cells or a tissue sample from a tumor of said subject. From such an analysis, a practitioner or other health professional (e.g., pathologist) can determine, for example, prognostic significance and/or predictive significance. In exemplary embodiments, the test provides for determination of a "recurrence score". in exemplary embodiments, a recurrence score is a numerical value, e.g., a number between 0 and 100, that corresponds to a specific likelihood of breast cancer recurrence within a certain time period after an initial diagnosis or treatment. In some embodiments, the score corresponds to a likelihood of recurrence within 5 years of the initial diagnosis or treatment. In some embodiments, the score corresponds to a likelihood of recurrence within 10 years of the initial diagnosis or treatment. Based on such a score, a subject (e.g., a TNBC patient) may be classified as low, intermediate or high risk for recurrence. Such a classification may assume that said subject follows a course of treatment including, for example, treatment with anti-hormonal therapy, such as tamoxifen or aromatase inhibitors (e.g., anastrozole), over the period of time following diagnosis or treatment. Depending on the subject risk for recurrence, treatment protocols may include anti-cancer drugs, chemotherapy, treatment with anti-hormonal therapy, such as tamoxifen or aromatase inhibitors, neoadjuvant hormonal therapy (oncology) and the like.

In exemplary embodiments of the invention, the diagnostic test is a noninvasive test that is performed on a small amount of the tissue removed during the original surgery lumpectomy, mastectomy, or core biopsy. In preferred embodiments, the tissue sample (after the surgical procedure) is fixed (e.g., formalin-fixed) and embedded (e.g., paraffin-embedded) so as to be preserved for further diagnostic testing. In other preferred embodiments, the sample (specimen) is fresh tissue sample/specimen. If using a fresh sample, the sample (from an unfixed tumor specimen) can be placed in a preservative solution within a short period of time, e.g., within an hour of surgery. Exemplary preservatives include, but are not limited to, solutions containing RNAse inhibitors.

In exemplary embodiments, a practitioner or other health professional (e.g., pathologist) prepares the samples for testing, (e.g., fixing, embedding, thin-sectioning) samples are analyzed, e.g., in a laboratory or at a testing facility, for example, via RT-PCR to determine expression of a plurality of genes, e.g., 10-20, 20-30, 30-40 or more, from a gene signature of the invention. In preferred embodiments, a panel of genes strongly correlated with recurrence-free survival is features in a diagnostic assay or kit of the invention. In exemplary embodiments of the invention, the results of the featured diagnostic tests can be integrated with other standard laboratory test results to help practitioners and/or health care professionals formulate a treatment plan based on the unique characteristics of the tumor or cell sample.

Pluralities or panels of genes featured in the diagnostic assays and/or kits of the invention can include cancer genes (those correlated with recurrence) and can include, for example, reference or control genes used to normalize the expression of the cancer genes.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value or level, of one or more genes (or mRNAs of said genes, or proteins expressed therefrom) as determined in a cell or sample positive for TNBC, as described herein. In another embodiment, a "suitable control" or "appropriate control" is a value or level, of one or more genes (or mRNAs of said genes, or proteins expressed therefrom) as determined in a cell or sample negative for TNBC, e.g., that determined in a cell or organism, e.g., a control or normal cell or organism, exhibiting, for example, normal traits. In yet another embodiment, a "suitable control" or "appropriate control" is a predefined value or level of one or more genes (or mRNAs of said genes, or proteins expressed therefrom).

VI. Screening Assays

In certain aspects, the invention features methods for identifying compounds useful in inhibiting the growth of TNBC cells, such compounds having potential therapeutic use in the treatment of TNBC. As described herein, the instant invention is based, at least in part, on the discovery of a previously unknown role for XPB1 is TNBC, such a role being linked to transcriptional activity of HIF1α. Genome-wide mapping of the XBP1 transcriptional regulatory network revealed that XBP1 regulates the hypoxia response through controlling HIF1α transcriptional activity and the expression of HIF1α targets. Accordingly, in exemplary aspects the invention features methods of identifying for identifying compounds useful in inhibiting the growth of TNBC cells, the methods featuring screening or assaying for compounds that modulate, e.g., activate or increase, or inhibit or decrease, the interaction of XBP1 and HIF1α, or biologically active portions thereof. In exemplary aspects, the methods comprise: providing an indicator composition comprising XBP1 and HIF1α, or biologically active portions thereof; contacting the indicator composition with each member of a library of test compounds; and selecting from the library of test compounds a compound of interest that decreases the interaction of XBP1 and HIF1α, or biologically active portions thereof, wherein the ability of a compound to inhibit growth of TNBC cells is indicated by a decrease in the interaction as compared to the amount of interaction in the absence of the compound As used herein, the term "contacting" (i.e., contacting a cell e.g. a cell, with a compound) includes incubating the compound and the cell together in vitro (e.g., adding the compound to cells in culture) as well as administering the compound to a subject such that the compound and cells of the subject are contacted in vivo. The term "contacting" does not include exposure of cells to an XBP-1 modulator that may occur naturally in a subject (i.e., exposure that may occur as a result of a natural physiological process).

As used herein, the term "test compound" refers to a compound that has not previously been identified as, or recognized to be, a modulator of the activity being tested. The term "library of test compounds" refers to a panel comprising a multiplicity of test compounds.

As used herein, the term "indicator composition" refers to a composition that includes a protein of interest (e.g., XBP-1 or a molecule in a biological pathway involving XBP-1, e.g., HIF1α), for example, a cell that naturally expresses the protein, a cell that has been engineered to express the protein by introducing one or more of expression vectors encoding the protein(s) into the cell, or a cell free composition that contains the protein(s) (e.g., purified naturally-occurring protein or recombinantly-engineered protein(s)).

As used herein, the term "cell" includes prokaryotic and eukaryotic cells. In one embodiment, a cell of the invention is a bacterial cell. In another embodiment, a cell of the invention is a fungal cell, such as a yeast cell. In another embodiment, a cell of the invention is a vertebrate cell, e.g., an avian or mammalian cell. In a preferred embodiment, a cell of the invention is a murine or human cell. As used herein, the term "engineered" (as in an engineered cell) refers to a cell into which a nucleic acid molecule e.g., encoding an XBP-1 protein (e.g., a spliced and/or unspliced form of XBP-1) has been introduced.

As used herein, the term "cell free composition" refers to an isolated composition, which does not contain intact cells. Examples of cell free compositions include cell extracts and compositions containing isolated proteins.

The ability of the test compound to modulate XBP-1 binding to HIF1α can also be determined. Determining the ability of the test compound to modulate XBP-binding to HIF1α can be accomplished, for example, by coupling the HIF1α with a radioisotope or enzymatic label such that binding of HIF1α to XBP-1 can be determined by detecting the labeled HIF1α in a complex. Alternatively. XBP-1 could be coupled with a radioisotope or enzymatic label to monitor the ability of a test compound to modulate XBP-1 binding to HIF1α in a complex. Determining the ability of the test compound to bind to XBP-1(or HIF1α) can be accomplished, for example, by coupling the compound with a radioisotope or enzymatic label such that binding of the compound to XBP-1(or HIF1α) can be determined by detecting the labeled compound in a complex. For example, targets can be labeled with $^{125}I$, $^{35}S$, $^{14}C$, or $^{3}H$, either directly or indirectly, and the radioisotope detected by direct counting of radioemission or by scintillation counting. Alternatively, compounds can be labeled, e.g., with, for example, horseradish peroxidase, alkaline phosphatase, or luciferase, and the enzymatic label detected by determination of conversion of an appropriate substrate to product.

It is also within the scope of this invention to determine the ability of a compound to interact with XBP-1 or HIF1α without the labeling of any of the interactants. For example, a microphysiometer can be used to detect the interaction of a compound with XBP-1 or HIF1α without the labeling of either the compound or the XBP-1 or HIF1α (McConnell, H. M., et al. 1992. *Science* 257, 1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and XBP-1 or HIF1α.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a preferred embodiment, the cell is a human cell. The cells of the invention can express endogenous XBP-1 or HIF1α or can be engineered to do so. For example, a cell that has been engineered to express the XBP-1 protein and/or HIF1α can be produced by introducing into the cell an expression vector encoding the protein. Recombinant expression vectors that can be used for expression of XBP-1 or a HIF1α.

In another embodiment, the indicator composition is a cell free composition. XBP-1 or HIF1α expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies can be used to produce a purified or semi-purified protein that can be used in a cell free composition. Alternatively, a lysate or an extract of cells expressing the protein of interest can be prepared for use as cell-free composition.

In one embodiment, the amount of binding of XBP-1 to HIF1α in the presence of the test compound is greater than the amount of binding of XBP-1 binding to HIF1α in the absence of the test compound, in which case the test compound is identified as a compound that enhances binding of XBP-1 to HIF1α. In another embodiment, the amount of binding of the XBP-1 to HIF1α in the presence of the test compound is less than the amount of binding of the XBP-1 to HIF1α in the absence of the test compound, in which case the test compound is identified as a compound that inhibits binding of XBP-1 to HIF1α.

Binding of the test compound to XBP-1 or HIFα1 can be determined either directly or indirectly as described above. Determining the ability of XBP-1(or HIF1α) protein to bind to a test compound can also be accomplished using a technology such as real-time Biomolecular Interaction Analysis (BIA) (Sjolander, S., et al. 1991. *Anal. Chem.* 63, 2338-2345; Szabo, A., et al. 1995. *Curr. Opin. Struct. Biol.* 5, 99-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In the methods of the invention for identifying test compounds that modulate an interaction between XBP-1 protein and HIF1α, the complete XBP-1(or e.g HIF1α) protein can be used in the method, or, alternatively, only portions of the protein can be used. In one embodiment of the above assay methods of the present invention, it may be desirable to immobilize either XBP-1(or HIF1α) for example, to facilitate separation of complexed from uncomplexed forms of one or both of the proteins, or to accommodate automation of the assay.

Binding of a test compound to a XBP-1 with HIF1α in the presence and absence of a test compound, can be accomplished in any vessel suitable for containing the reactants. Examples of such vessels include microtitre plates, test tubes, and micro-centrifuge tubes. In one embodiment, a fusion protein can be provided in which a domain that allows one or both of the proteins to be bound to a matrix is added to one or more of the molecules. For example, glutathione-S-transferase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or XBP-1 (or HIF1α) protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either an XBP-1 protein or HIF1α can be immobilized utilizing conjugation of biotin and streptavidin. Biotinylated protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with protein but which do not interfere with binding of the proteins can be derivatized to the wells of the plate, and unbound XBP-1 or HIF1α protein is trapped in the wells by antibody conjugation. Methods for detecting such complexes, in addition to those described above for the GST-immobilized complexes, include immunodetection of complexes using antibodies reactive with XBP-1 or HIF1α, as well as enzyme-linked assays which rely on detecting an enzymatic activity associated with the XBP-1 or HIF1α.

Another aspect of the invention pertains to kits for carrying out the screening assays, modulatory methods or diagnostic assays of the invention.

This invention is further illustrated by the following examples which should not be construed as limiting. The contents of all references, patents, and published patent applications cited throughout this application, as well as the figures and the sequence listing, are hereby incorporated by reference.

EXAMPLES

Example 1: The UPR is Activated in Human Breast Cancer Patients

Figure 1B:
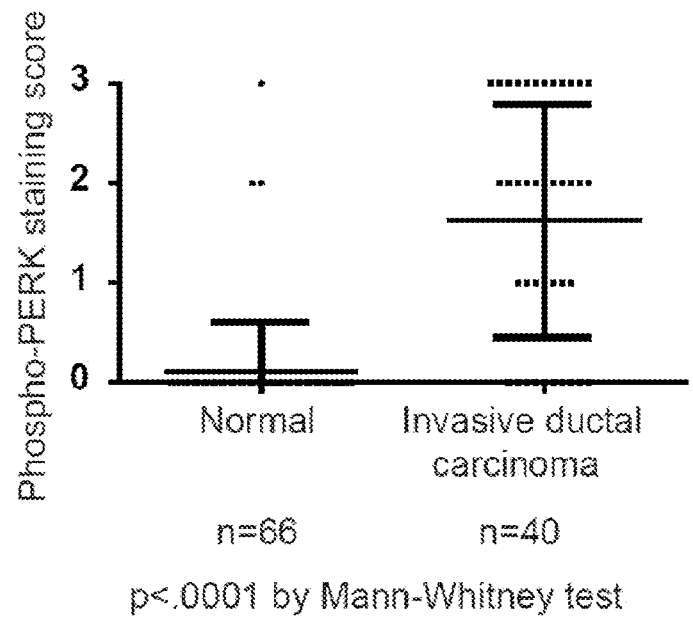
Figure 1C:
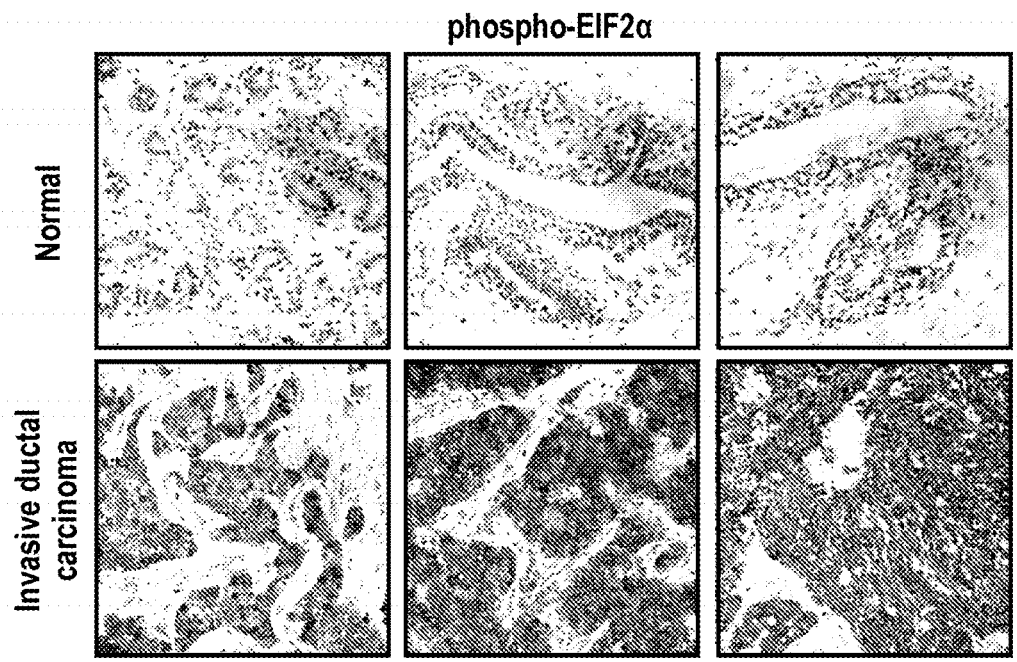
Figure 1D:
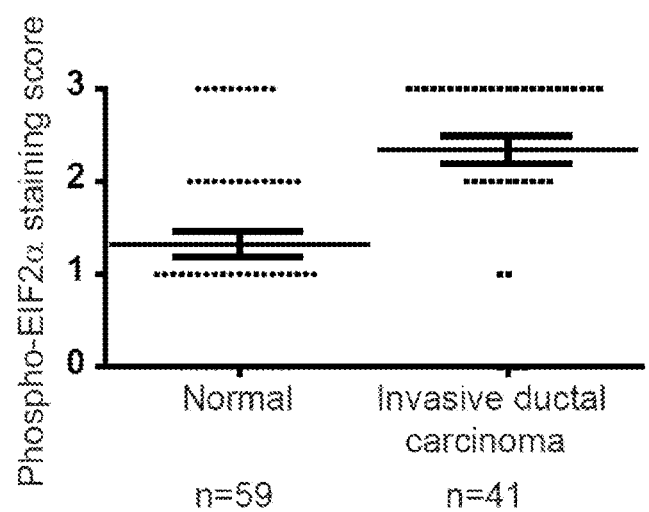

To determine whether the UPR is activated in breast cancer, we used immunohistochemistry (IHC) to examine the phosphorylation of PERK, a marker of UPR activation, in human primary breast tumor samples. By staining breast cancer tissue microarrays (TMA) containing 66 normal breast tissue samples and 40 tumor tissue samples, we found that PERK was preferentially phosphorylated in breast tumors, but not in normal breast tissue (FIG. 1A, 1B), suggesting that activation of the UPR occurs specifically in tumors. Next, the same TMA were stained with antibodies specifically recognizing phosphorylation of eukaryotic translational initiation factor 2α (eIF2α), another marker of UPR activation. Similarly, eIF2α was phosphorylated in malignant breast tumors but not normal breast tissue (FIG. 1C, 1D). Thus, the UPR is preferentially activated in breast tumors.

Figure 2C:
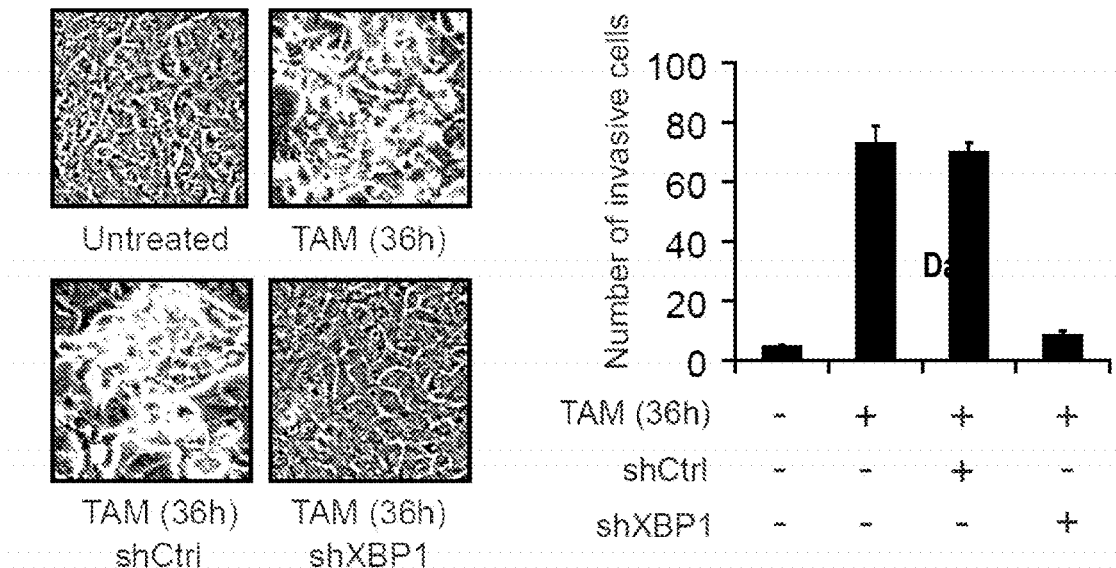
Figure 2C:
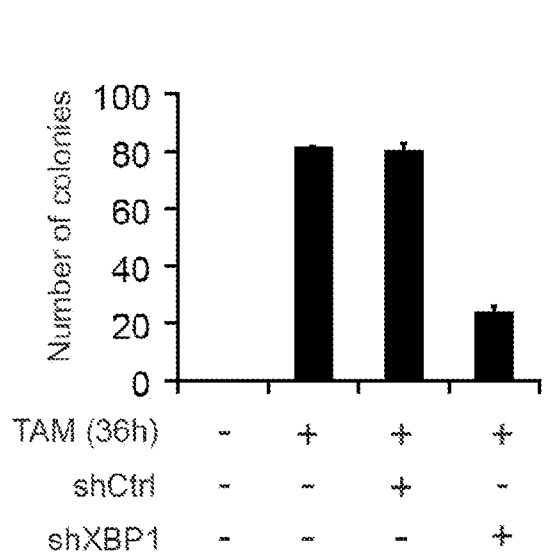
Figure 2D:
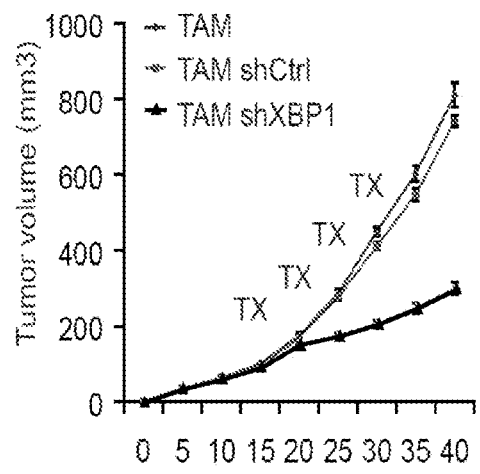
Figure 2E:
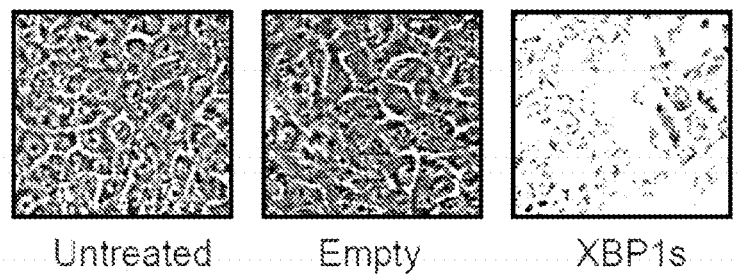
Figure 2F:
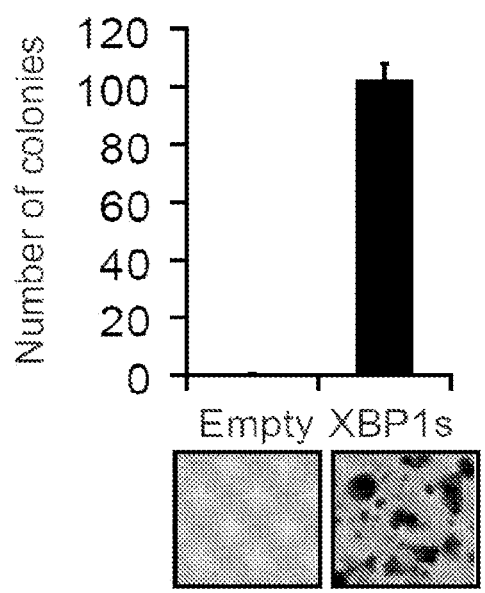

Example 2: XBP1 is Required for Transformation of Immortalized Mammary Epithelial Cells The IRE1-XBP1 axis of the UPR shows robust conservation from yeast to metazoans, including humans. To investigate the role of XBP1 in cellular transformation, we used MCF10A immortalized mammary epithelial cells that express ER-Src, a fusion of the Src kinase oncoprotein (v-Src) and the ligand binding domain of the estrogen receptor. Treatment of these cells with tamoxifen (TAM) for 36 hr results in neoplastic transformation, including the ability to form colonies in soft agar, increased motility and invasive ability, and tumor formation upon injection into nude mice (Iliopoulos, D., et al. 2009. *Cell* 139, 693-706). Knockdown of XBP1 expression with a highly effective shRNA (Figure S1) blocked the neoplastic transformation of MCF10A ER-Src cells (FIG. 2A). Furthermore, XBP1 silencing reduced the invasiveness and the ability of MCF10A ER-Src cells to form colonies in soft agar and tumors in immunodeficient mice (FIG. 2B-D). We tested the ability of enforced XBP1 expression to transform MCF10A cells by overexpression of the XBP1 spliced form (XBP1s) in MCF10A ER-Src cells in the absence of tamoxifen, XBP1 overexpression was sufficient to induce transformation in the absence of tamoxifen (FIG. 2E), Furthermore, XBP1s overexpression increased colony formation in a soft agar assay (FIG. 2F). Collectively, these results demonstrate that XBP1 is both necessary and sufficient for the transformation of mammary epithelial cells.

Example 3: XBP1 Inhibition Blocks Breast Cancer Cell Growth and Invasiveness Both Ex Vivo and In Vivo; XBP1 Silencing Blocks Triple Negative Breast Cancer Progression To further characterize the function of XBP1 in breast cancer, we first determined the activation status of XBP1 in different breast cancer cell lines. Breast cancers can be classified as luminal or basal-like, depending on their expression of different cytokeratins (Perou. C. M., et al. 2000. *Nature* 406, 747-752; Vargo-Gogola, T., et al. 2007, Cancer 7, 659-672). Unexpectedly, XBP1 was preferentially spliced and activated in basal-like breast cancer cells (FIG. 3A), which harbor a transcriptome similar to that of triple negative breast cancer (TNBC), a subtype of breast cancer that is extremely aggressive and difficult to target due to the lack of expression of the estrogen (ER), progesterone (PR) and human epidermal growth factor 2 (HER2) receptors (Foulkes, W. D, et al. 2010. *N Engl J Med* 363, 1938-1948). In particular, while XBP1 expression was readily detected in both luminal and basal-like breast cancer cells, the level of its spliced (activated) form was higher in the latter cell type (FIG. 1A), which comprises primarily TNBC (Perou, C, M., et al. 2000. *Nature* 406, 747-52; Vargo-Gogola, T., et al. 2007. *Nat Rev Cancer* 7, 659-72; Herschkowitz, J. I., et al. 2007. *Genome Biol* 8. R76). Furthermore, silencing XBP1 expression decreased the ability of different breast cancer cell lines to form colonies in soft agar (FIG. 3B).

TNBC is a highly aggressive subtype of breast cancer characterized by the absence of estrogen receptor (ER), progesterone receptor (PR) and human epidermal growth factor 2 (HER2) expression (Foulkes, W. D., et al. 2010. *N Engl J Med* 363, 1938-48). We next demonstrated that silencing of XBP1 significantly impaired soft agar colony formation (FIG. 1B) and invasiveness (FIG. 1C) of multiple TNBC cell lines (MDA-MB-231, MBD-MB-468, HBL-100, MDA-MB-436, MDA-MB-157), suggesting a potential role of XBP1 in the regulation of anchorage-independent growth and invasiveness of TNBC.

Interestingly, knockdown of XBP1 was more effective in suppressing the proliferation of basal-like (MDA-MB-231, MBD-MB-468, HBL-100, MDA-MB-157, MDA-MB-435, MDA-MB-436, SUM-159) than luminal (MCF7, BT-474, SKBR3, T47D, MDA-MB-361) breast cancer cell lines, consistent with the preferential splicing of XBP1 in basal-like cells. Similarly, knockdown of XBP1 decreased the invasiveness of breast cancer cell lines, a phenotype that was more dramatic in basal-like lines (FIG. 3C). These data suggest that. XBP1 regulates the growth and invasiveness of breast cancer cells, especially basal-like breast cancer cells.

To assess the function of XBP1 in vivo, we established an orthotopic xenograft mouse model with inducible expression of shRNA against XBP1. In particular, we infected MDA-MB-231 cells, a TNBC cell line, with lentiviruses encoding XIP1 shRNAs under the control of a doxycycline-inducible promoter. Cells infected, with a lentivirus encoding a scrambled LacZ shRNA served as a control, Doxycycline treatment of cells infected with the XBP1 shRNA lentivirus led to an 85% reduction in XBP1 mRNA levels compared to cells grown in the absence of doxycycline (FIG. 3D).

Figures 3F, 3G:
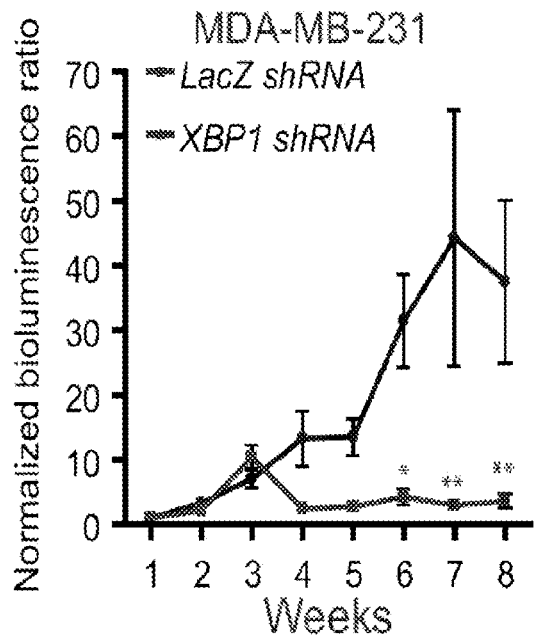
Figure 3K:
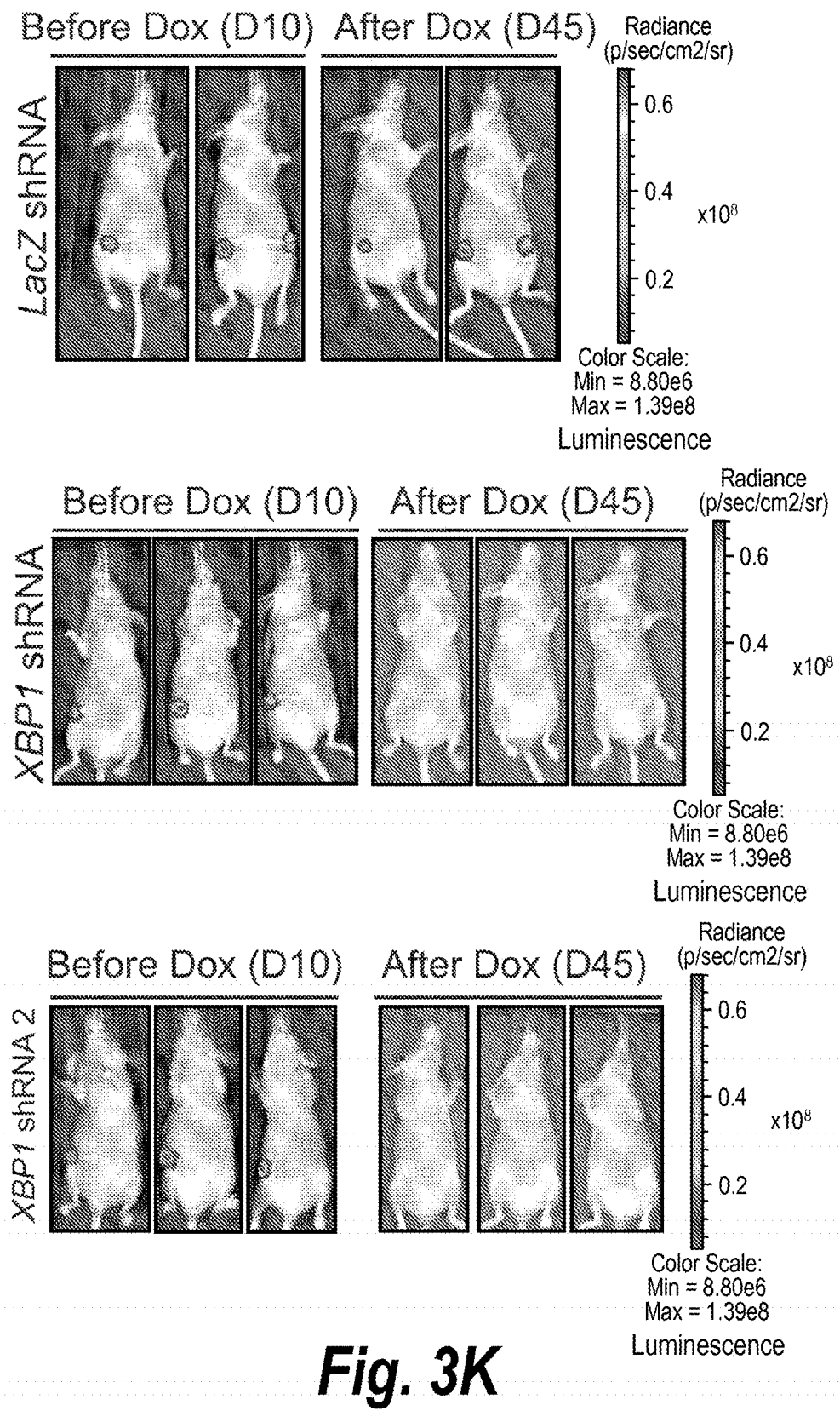
Figure 3L:
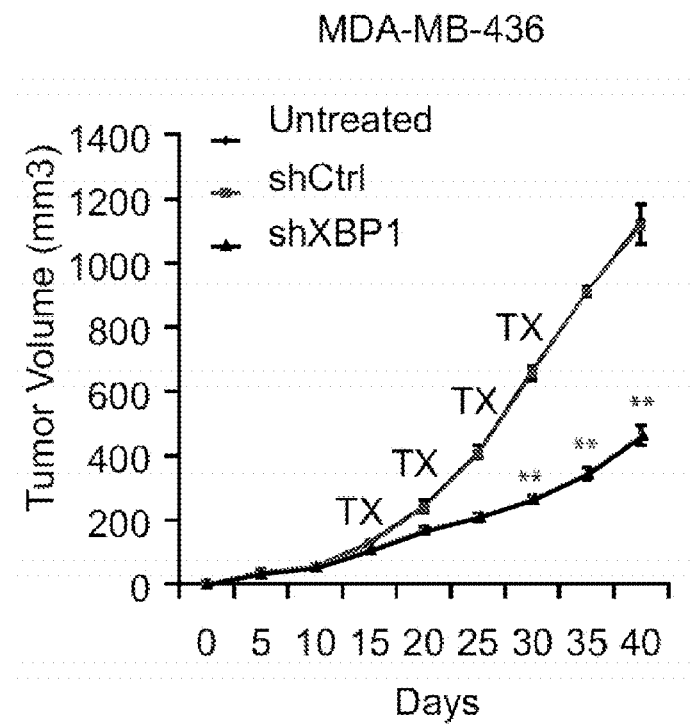
Figure 3M:
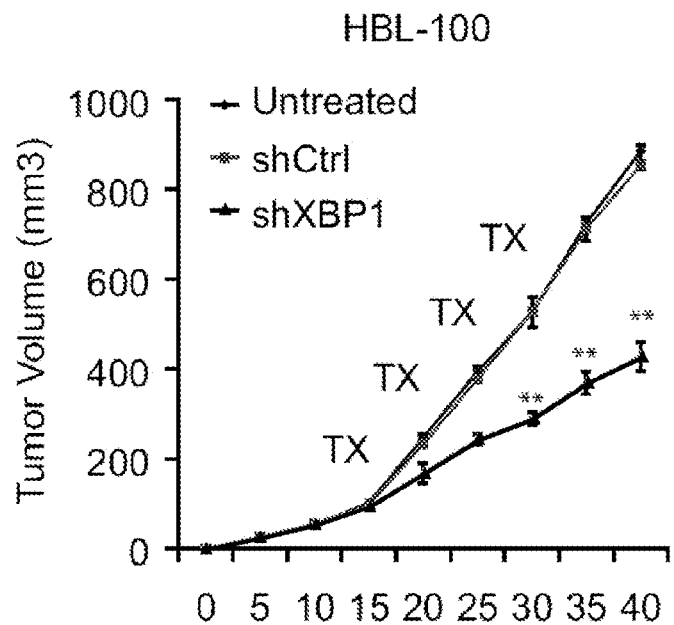

Next, these MDA-MB-231 cells infected with the shRNA lentiviruses were further infected with a retrovirus encoding luciferase. After injection with retroviruses, these cells were implanted (injected) orthotopically in the mammary glands of NOD/SCID/IL2Rγ−/− mice. The kinetics of tumor growth were monitored with bioluminescent imaging. At>two weeks after implantation (19 days), prior to induction of the XBP1 shRNA, XRP1 shRNA and control tumors exhibited similar luciferase signals (FIG. 3E). These mice were then fed chow containing doxycycline to induce the XBP1 shRNA and serially monitored using bioluminescence. After 4 weeks of XBP1 depletion a significant inhibition of tumor growth was observed (FIGS. 3E and 3F). XBP1 was efficiently silenced in the tumor (FIG. 3I). While tumors expressing control shRNA (n=8) began to metastasize to the lungs 9 weeks after transplantation, no metastasis was observed in the XRP1 shRNA xenograft tumors (n=8) (FIG. 3E). To rule out off-target effects of the XBP1 shRNA, the same assays were conducted with another inducible XBP1 shRNA construct targeting a different region of XBP1 (FIG. 3J), which yielded similar results (FIG. 3K). To exclude the possibility of cell line specific effects, subcutaneous xenograft experiments were performed using two other TNBC cell lines: MDA-MB-436 and HBL-100 cells. As expected, XBP1 silencing significantly repressed the formation of MDA-MB-436 and HBL-100 TNBC-derived tumors (FIG. 3L). Importantly, we examined the functional relevance of XBP1 in primary human breast tumor cells. We inhibited XBP1 by siRNA in a patient derived TNBC xenograft model (BCM-2147). Silencing of XBP1 in this model significantly decreased tumor incidence (FIG. 3G) and suppressed tumor growth (FIG. 3H), further supporting the role of XBP1 in TNBC. Collectively, these results demonstrate that loss of XBP1 suppresses the growth and metastasis (tumorigenicity and progression) of human triple negative breast tumors.

Figure 4H:
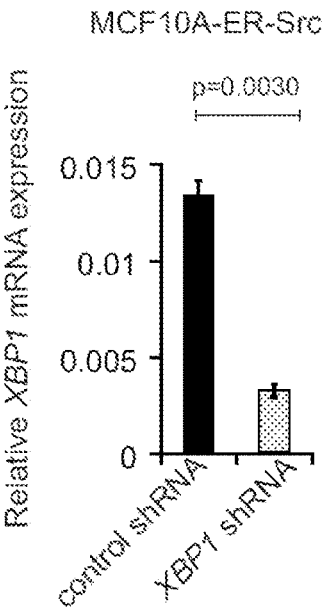
Figure 4I:
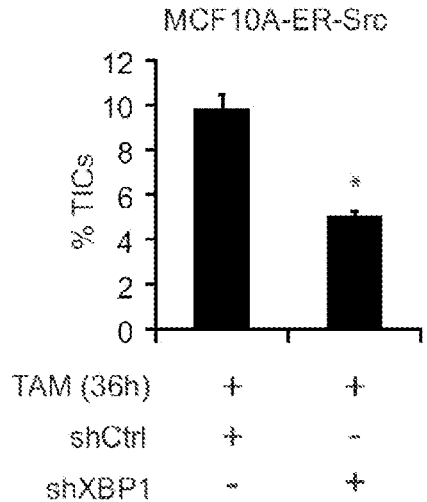
Figure 4J:
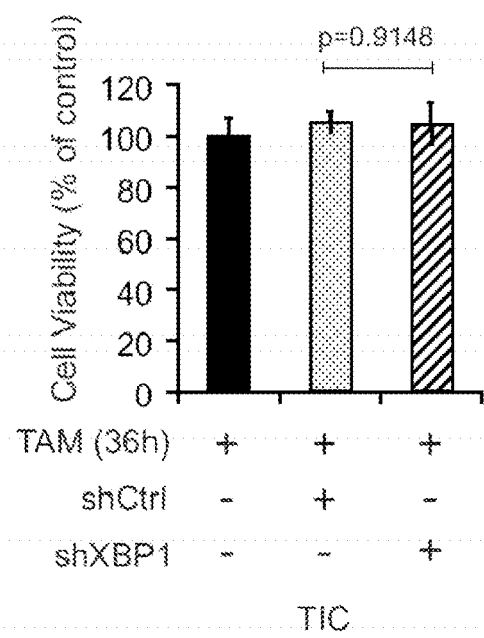
Figure 4K:
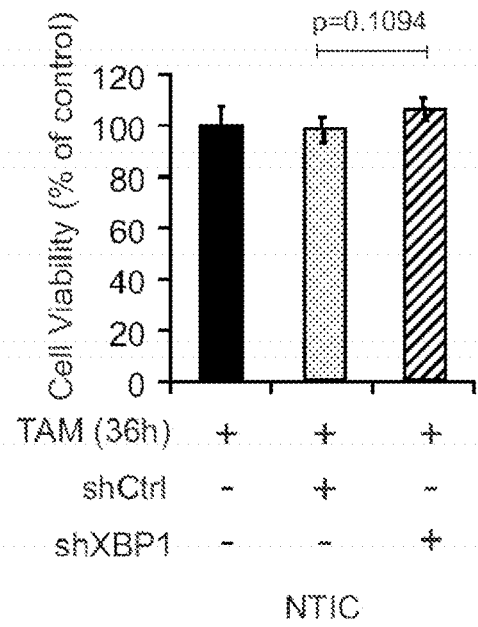

Example 4: XBP1 is Required to Sustain Tumor Initiating Cell (TIC) Self-Renewal; XBP1 is Required for Tumor Initiating Cells Previous studies have shown that basal-like breast cancer cells are more aggressive than luminal cells due to increased numbers of a stem cell-like $CD44^{high}/CD24^{low}$ subpopulation, termed tumor initiating cells (TICs) (Al-Hajj, M., et al. 2003. *Proc Natl Acad Sci USA* 100, 3983-3988; Mani, S. A., et al. 2008. *Cell* 133, 704-715). To interrogate the effect of XBP1 on TICs, we used a model of breast epithelial cells (MCF10A) carrying an inducible Src oncogene (ER-Src). in which the Src kinase oncoprotein (v-Src) was fused with the ligand binding domain of the estrogen receptor (Iliopoulos, D., et al. 2009. *Cell* 139, 693-706). Recently, it has been shown that during transformation of MCF10A ER-Src cells, there is formation of a $CD44^{high}/CD24^{low}$ population with TIC characteristics (Iliopoulos et al., 2011). In particular, Treatment of these cells with tamoxifen (TAM) for 24-36 hr results in neoplastic transformation and the gain of a CD44high/CD24low population with tumor-initiating property (Iliopoulos, D., et al. 2011. *Proc Natl Acad Set USA* 108, 1397-402). In transformed MCF10A ER-Src cells, knockdown of XBP1 blocked the formation of the $CD44^{high}/CD24^{low}$ ER-Src TIC population (reducing the $CD44^{high}/CD24^{low}$ TIC fraction)(FIG. 4B and Figures H-I). In this system, XBP1 was more highly spliced in TICs ($CD44^{high}/CD24^{low}$) relative to non-TICs (NTICs) (FIG. 4A). XBP1 silencing also suppressed the ability of transformed MCF10A ER-Src cells to form mammospheres (FIG. 4C), an assay used to assess the self-renewal of breast TICs (Dontu, et al. 2003. *Genes Dev* 17, 1253-1270). These phenotypes were not due to a direct effect of XBP1 on cell viability (FIGS. 4J-K).

To test if expression of XBP1 was sufficient to induce TIC properties in NTICs. XBP1s was overexpressed, in $CD44^{low}/CD24^{high}$ NTICs derived from MCF10A ER-Src cells. This induced the formation of a population with a TIC-like $CD44^{high}/CD24^{low}$ surface phenotype and enhanced mammosphere forming ability.

Tumorigenicity in a murine host is the gold standard for evaluating the stem cell-like properties of TICs (Clarke, M. F., et al. (2006). *Cancer Res* 66, 9339-9344). To further investigate if the TICs induced by XBP1s expression in NTICs also display TIC properties in a murine tumor formation assay, NTICs or NTICs with enforced expression of XBP1s (XBP1s-NTIC) were injected into NOD/SCID mice at a range of dilutions. Remarkably, as few as 100 XBP1s-NTICs cells were able to generate a tumor, whereas control NTICs failed to form tumors at any dilution. Thus, under these conditions, XBP1s is sufficient for the induction of functional breast TICs.

In a limiting dilution experiment, TAM-treated MCF10A-ER-Src cells bearing control shRNA were able to initiate tumors when as few as $1\times10^4$ or $1\times10^5$ cells were implanted. However, XBP1-depleted cells showed complete loss of tumor-seeding ability even when $1\times10^6$ cells were xenografted (FIG. 4D).

In addition to MCF10A ER-Src cells, we examined the effects of)(BPI inhibition in TICs derived from breast cancer cell lines. XBP1 inhibition suppressed the growth of mammospheres derived from MDA-MB-231, MDA-MB-468 and MDA-MB-436 cells (FIG. 4F).

To evaluate the functional relevance of XBP1 in human cancer patients, we sorted the CD44$^{high}$/CD24$^{low}$ subpopulation directly from human TNBC patient samples, and confirmed XBP1 splicing to be elevated in this fraction compared to the CD44low/CD24high cells (FIG. 4E). Infection of the CD44$^{high}$/CD24$^{low}$ cells with lentivirus expressing XBP1 shRNA, inhibited the formation of mammospheres derived from a number of patient-derived TNBC tissues (FIG. 4F). Conversely, overexpression of XBP1s in NTICs (CD44$^{high}$/CD24$^{low}$) sorted from primary human TNBC (or derived from breast cancer cell lines) transformed them into TICs as based on surface phenotype. Remarkably, these XBP1s-induced TICs are able to form tumors in immunodeficient mice at very low dilutions (as low as 10 xenografted cells) whereas none of the control parental NTICs were tumorigenic (FIG. 4G).

Figure 4L:
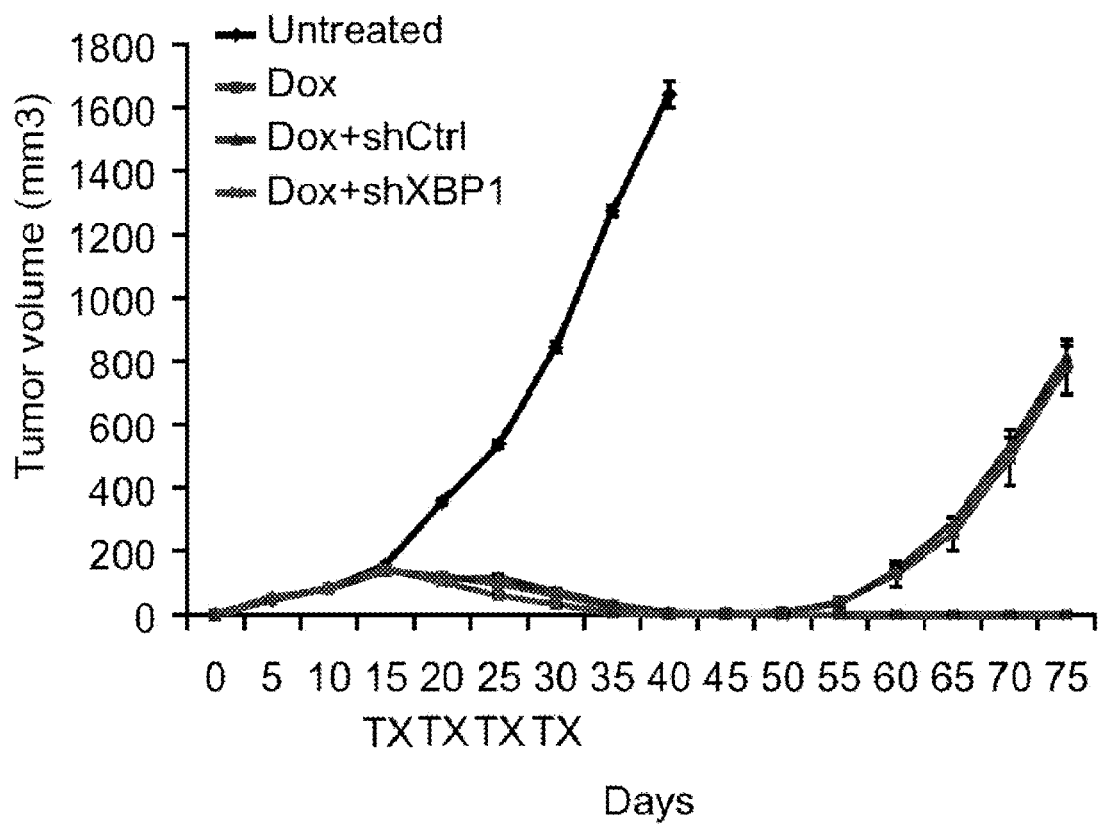
Figure 4M:
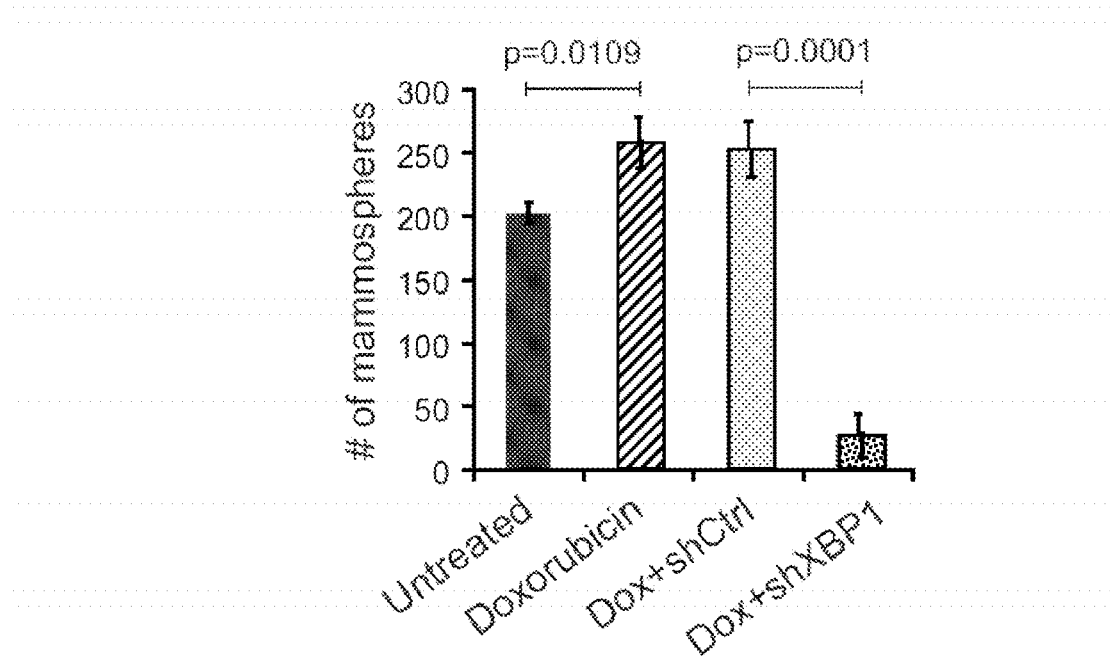

Collectively, these data establish a critical and unexpected role of XBP1 in TICs, likely contributing to its function in promoting triple-negative breast cancer Example 5: XBP1 Silencing Increases Sensitivity and Reduces Resistance to Chemotherapy; Inhibition of XBP1 Suppresses Tumor Relapse Chemotherapy is the only systemic therapy currently used clinically to treat TNBC. However, patients with TNBC have the highest rate of relapse within 1-3 years despite the use of adjuvant chemotherapy (Lehmann, B. D., et al. 2011. *J Clin Invest* 121, 2750-67). Moreover, TICs are resistant to chemotherapy and are believed to be responsible for tumor relapse after chemotherapy (Dean, M., et al., 2005. *Nat Rev Cancer* 5, 275-284). Given that XBP1 appears to induce TIC differentiation, the role of XBP1 in mediating the relapse of the MDA-MB-231 xenograft tumor after chemotherapy was evaluated. It was believed that this approach would yield further insights into the function of XBP1 in TNBC. Treatment of MDA-MB-231 xenograft tumors with doxorubicin (i.p.) every 5 days, from day 15 until day 30, suppressed tumor growth (FIG. 4M). Relapse from treatment occurred on day 60, i.e., Tumor relapse after treatment was detected from day 60 onwards. Strikingly, combinatorial treatment with doxorubicin and XBP1 shRNA not only blocked tumor growth but also inhibited tumor relapse (FIG. 4N).

The presence of tumor initiating cells (TICs), characterized by the cell surface phenotype CD44high/CD24low and the expression of ALDH1 (Ginestier. C., et al, 2007. *Cell Stem Cell* 1, 555-67), are thought to play a role in chemotherapy resistance and tumor relapse after systemic adjuvant therapy (Dean, M., et al. 2005. *Nat Rev Cancer* 5, 275-84; Al-Hajj, M., et al. 2003. *Proc Natl Acad Sci USA* 100, 3983-8; Creighton, C. J., et al, 2009. *Proc Natl Acad Sci USA* 106, 13820-5; Li. X., et al. 2008. *J Natl Cancer Inst* 100, 672-9). In order to test whether suppression of tumor relapse (this increased sensitivity to chemotherapy) is due to an effect of XBP1 on TICs, we examined mammosphere-forming ability of cells (the number of mammospheres) derived from the treated tumors (day 20). Mammosphere assays are used to assess the activity of breast TICs in vitro (Dontu, G., et al. 2003. *Genes Dev* 17, 1253-70). Consistent with the previously observed enrichment of TIC following chemotherapy (Creighton, C. J., et al. 2009. *Proc Natl Acad Sci USA* 106, 13820-5), mammosphere formation was increased in cells derived from doxorubicin treated tumors (FIG. 4L). Intriguingly, tumors treated with doxorubicin in combination with XBP1 knockdown demonstrated substantially suppressed mammosphere growth (FIG. 4M), suggesting that XBP1 silencing blunted chemotherapy-induced expansion of the TIC pool. Thus, the combination of chemotherapy and XBP1 knockdown suppresses breast tumor growth and prolongs remission in breast xenografts.

Collectively, these data demonstrate that XBP1 is required to sustain TIC self-renewal in breast cancer.

Example 6: XBP1 Interacts with HIF1α and Co-occupies the Promoters of HIF1α Targets; HIF1α is a Co-Regulator of XBP1 in TNBC Given the importance of XBP1 in the breast cancer models above and to further understand how XBP1 contributes to TNBC, we sought to identify transcriptional networks regulated by XBP1 and to dissect the underlying mechanism by mapping the physiological targets of XBP1s using ChIP coupled with high-throughput sequencing (ChIP-seq). Tumor cells are exposed to hypoxia and glucose deprivation, and these factors are appreciated to have a large impact on tumor pathophysiology (Semenza, G. L. 2003. *Nat Rev Cancer* 3, 721-32). XBP1s was highly expressed in MDA-MB-231 cells by exposure to the physiological stressors (FIG. 5J) To examine if these stressors of cellular physiology might induce XBP1 activation via splicing, MDA-MB-231 cells were grown in hypoxic and glucose deprivation conditions for 24 h. Exposure to hypoxia and glucose deprivation induced splicing of XBP1, and this resulted in a corresponding increase in the signal intensity detected in ChIP-seq experiments. Using a ChIP-seq approach (using a polyclonal antibody specifically recognizing the XBP1s protein), we identified a total of 6317 high-confidence XBP1 binding sites in MDA-MB-231 cells. 13.9% of the binding sites mapped to promoters, and 73.6% were found at distal intergenic and intronic regions (FIG. 5K). Notably, the overlap of the genes bound by XBP1 in MDA-MB-231 cells versus those bound in plasma cells or pancreatic beta cells was small (Acosta-Alvear, D., et al. 2007. *Mol Cell* 27, 53-66). Therefore, our study revealed a unique repertoire of XBP1 binding sites specific for TNBCs. As expected, XBP1 extensively bound to genes involved in the UPR pathway, such as DNAJB9, HSPA5, and EDEM. By performing microarray and gene set enrichment analysis (GSEA) of genes differentially expressed upon XBP1 depletion in MDA-MB-231 cells, we found that the UPR pathway was among the most enriched categories, with significant enrichment of genes involved in ER stress and UPR pathways indicating that XBP1 directly regulates the UPR in TNBC cells.

To determine the in vivo sequence specificity of XBP1. we derived the consensus sequence motifs by using a motif-discovery algorithm MDScan (Liu, X. S., et al. 2002. *Nat Biotechnol* 20, 835-839). Notably, the predominant motif found was a perfect match to the XBP1 consensus site GC/ACACGT (FIG. 5L), confirming the validity of the ChIP-seq dataset. Remarkably, a HIF1α binding motif showed statistically significant enrichment in our dataset (enrichment of the HIF1α binding motif in the XBP1 sites (p=1.0×10$^{-30}$)) (FIG. 5A), suggesting potential cooperation between HIF1α and XBP1, e.g., that HIF1α frequently co-localizes to the same transcriptional regulatory elements as XBP1. HIF1α is a ubiquitously expressed, $O_2$ dependent subunit of Hypoxia Induced Factor (HIF1), known to play essential roles in TNBC and in breast TICs self-renewal (Schwab, L. P., et al. 2012. Breast Cancer Res 14, R6). The enrichment of the HIF1α motif in the XBP1 ChIP-seq dataset raised the possibility that XBP1 and HIF1α might interact in the same transcriptional complex.

To assess this possibility, Flag-tagged HIF1α was co-expressed with XBP1s in 293T cells cultured under hypoxia. Treatment of cells with the proteasome inhibitor MG132 for 16 hours was necessary to inhibit the basal turnover of HIF1α. Extracts were harvested and immunoprecipitated with M2 FLAG antibody, and HIF1α was found to co-precipitate with XBP1s (FIG. 5B). This interaction could also be observed with endogenous proteins in the context of two TNBC cell lines. MDA-MB-231 and Hs578T cells were treated with tunicarnycin (TM), a potent pharmacologic ER-stress inducer that triggers robust XBP1 splicing. Nuclear extracts were harvested, and immunoprecipitation using an anti-HIF1α antibody demonstrated the co-precipitation of XBP1 (FIGS. 5C and 5M). Thus, endogenous XBP1 interacts with HIF1α in the nucleus.

Figure 5D:
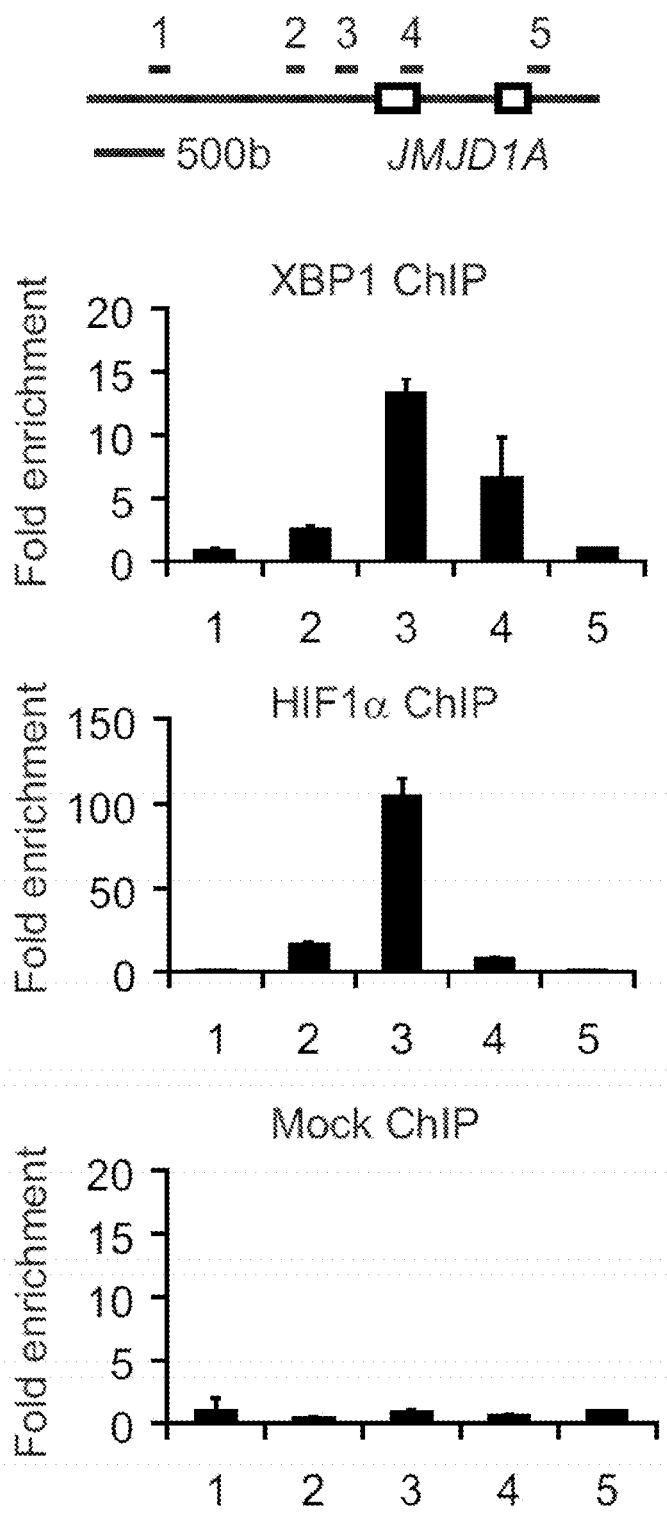
Figure 5N:
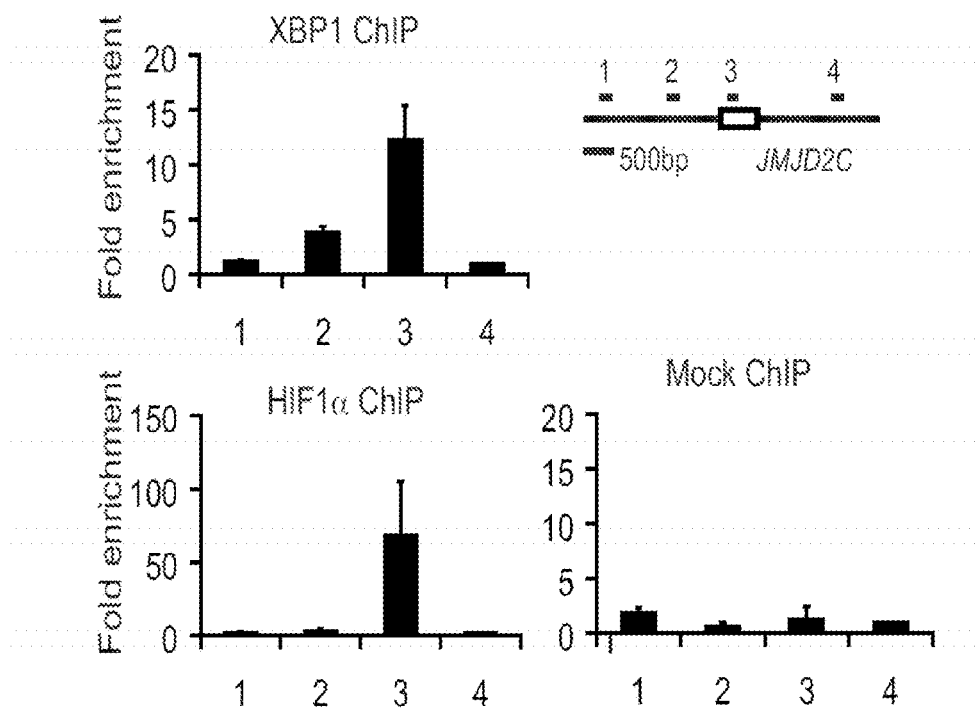

To extend these results, we next asked whether XBP1 binds together with HIF1α specifically at the site of HIF1α target genes. Direct ChIP-qPCR was performed to examine the co-occupancy XBP1 and HIF a at several well known HIF1α direct targets including VEGFA, PDK1, DDIT4, JMJD1A and JMJD2C (Xia, X, et al. 2009. Proc Natl Acad Sci USA 106, 4260-4265). As shown in FIG. 5D-F. and FIG. 5N, both XBP1 and HIF1α bind to the promoters of VEGFA, PDK1, DDIT4, JMJD1A and JMJD2C under hypoxic conditions, whereas control GST ChIP did not show any enrichment. Next, we ascertained the functional contribution of XBP1 to the regulation of HIF1α targets. As the physiologic response to tissue hypoxia is initiated by the binding of the HIF-1 transcription factor to the hypoxia response element (HRE) (Semenza, G. L., 2001, Cell 107, 1-3), a luciferase construct containing three copies of HRE (FIG. 5G) was co-transfected together with a construct encoding XBP1s into MDA-MB-231 cells. XBP1s was able to transactivate the HRE reporter in a dose dependent manner, whereas the empty vector had no effect (FIG. 5H). Conversely, depletion of XBP1 by two independent shRNA constructs dramatically reduced HRE activity under hypoxic conditions (FIG. 5I). Taken together, these data demonstrate that XBP1s interacts with HIF1α and in turn the two collaborate to regulate the promoters of HIF1α targets.

Example 7: XBP1 Regulates the Response to Hypoxia (the Hypoxia Response Pathway)

Figure 6A:
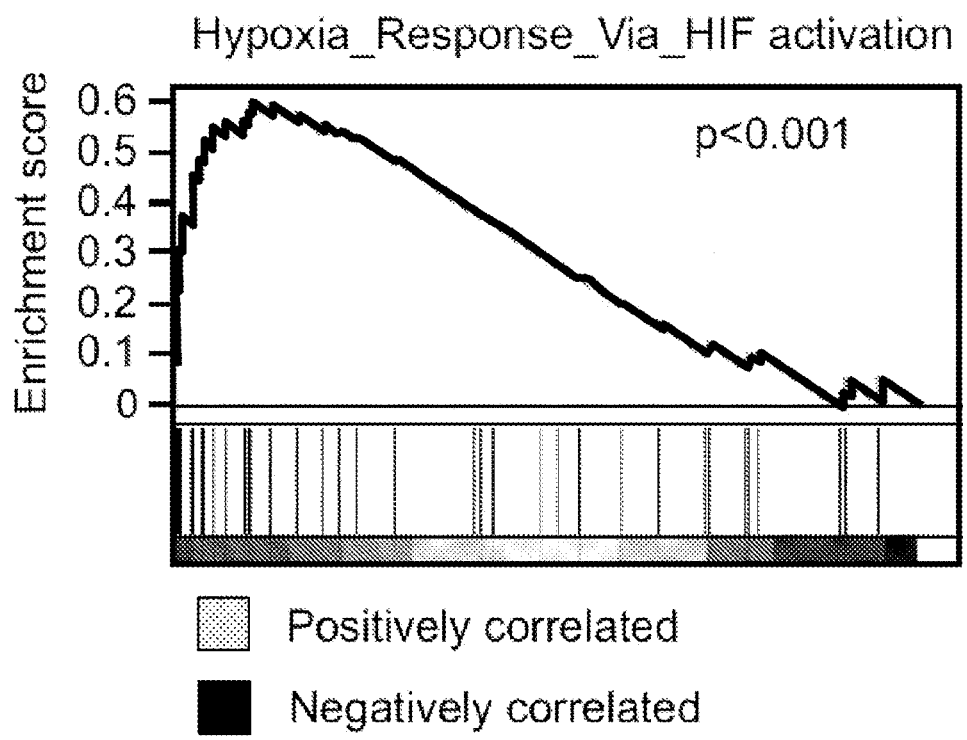
Figure 6B:
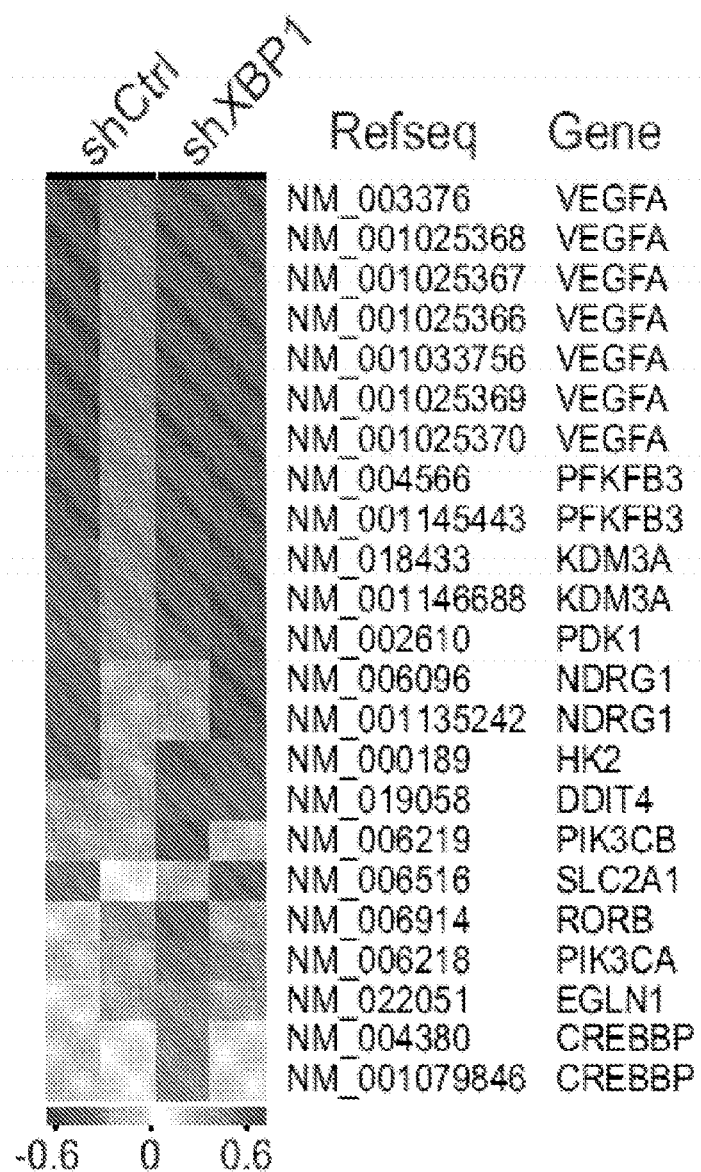
Figure 6C:
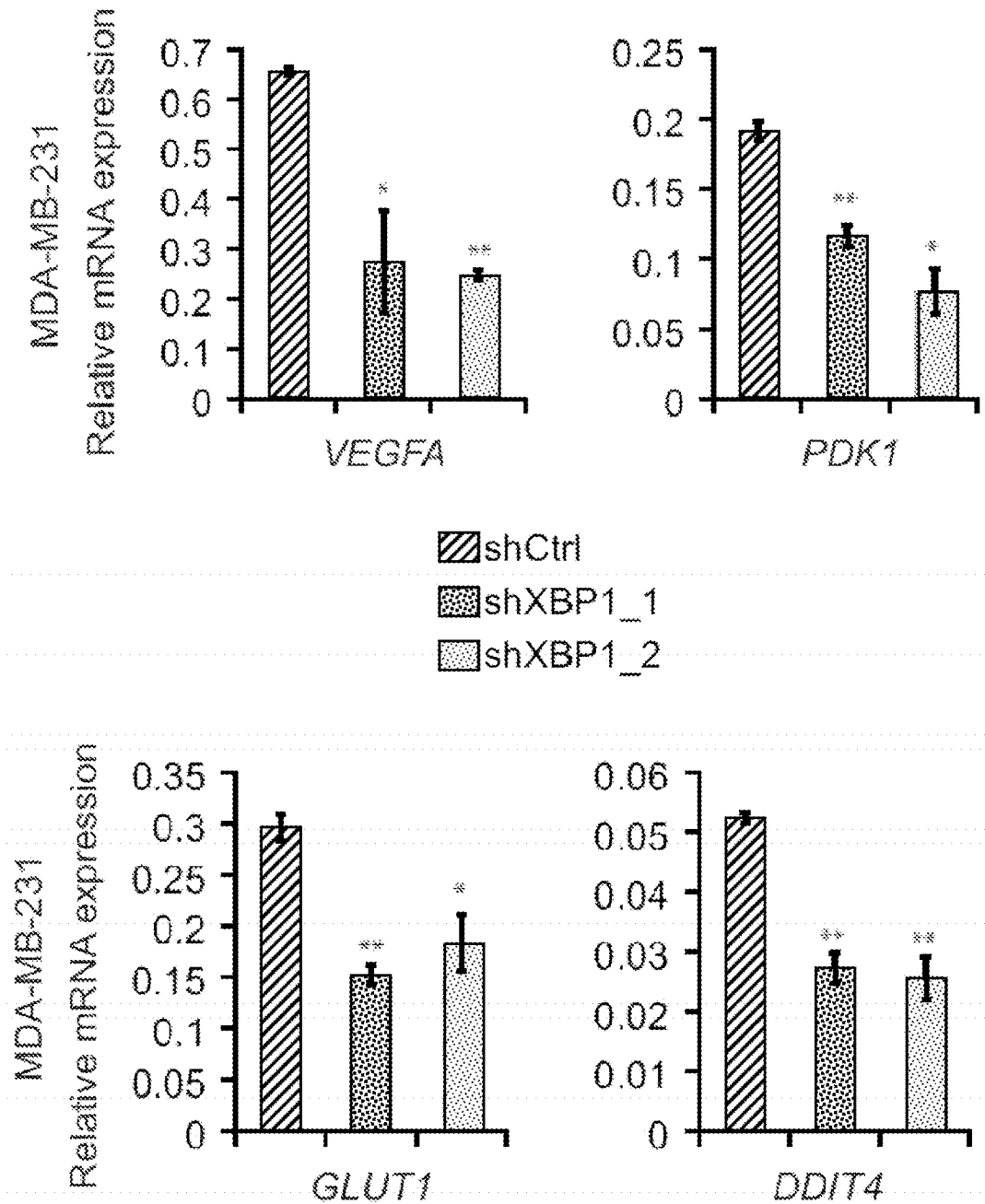
Figure 6D:
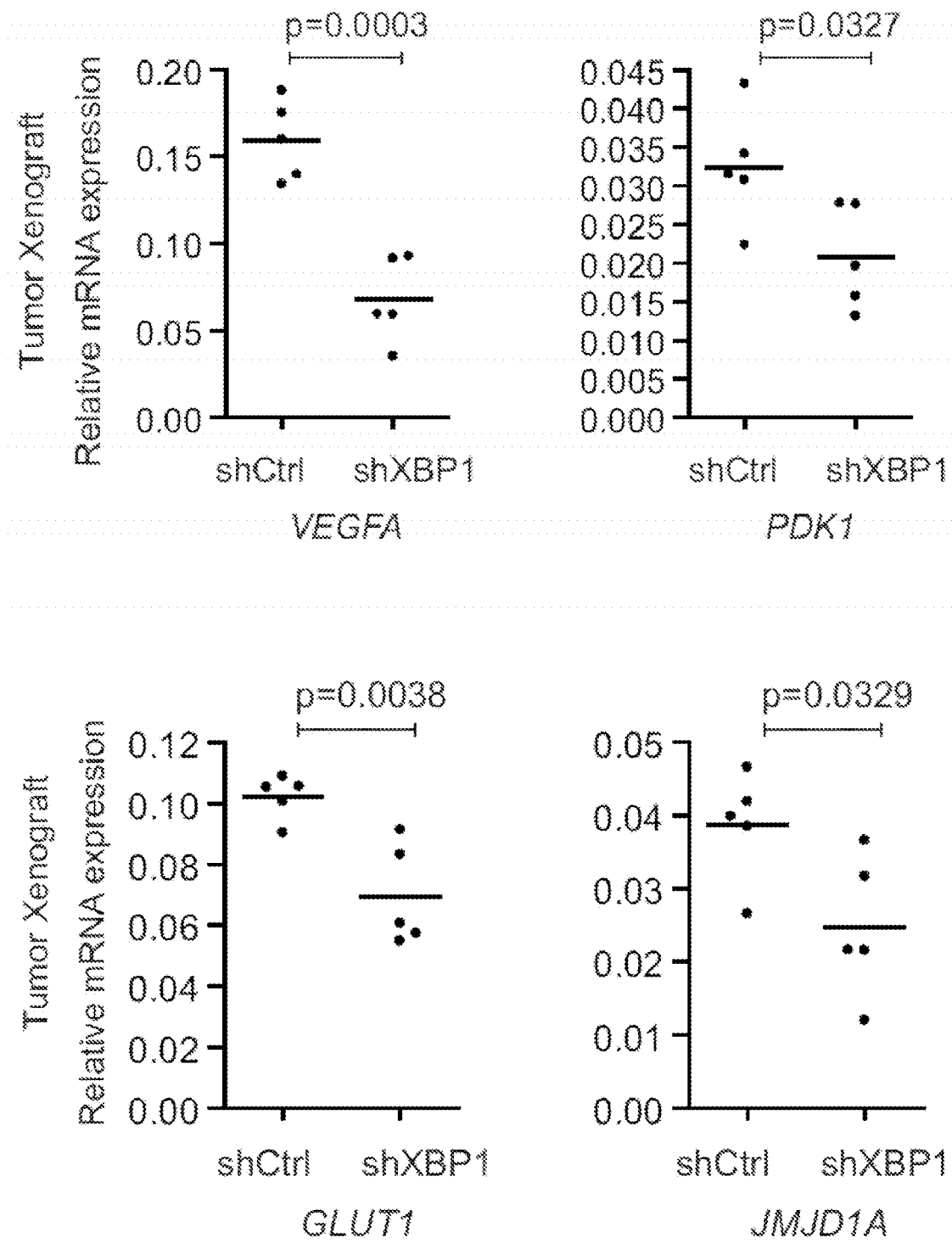

Next, we profiled the differential transcriptome regulated by XBP1 silencing in MDA-MB-231 cells using gene expression microarray analysis. In particular, to identify the transcriptional programs regulated by XBP1, we perturbed XBP1 expression in MDA-MB-231 cells by shRNA and examined the effects on gene expression by microarray analysis under the same conditions as the above ChIP-seq assay. Gene set enrichment analysis (GSEA) identified significant enrichment of genes in the hypoxia response pathway (FIG. 6A, B). To verify the regulation of the hypoxia response by XBP1, we exposed cells to hypoxia, and demonstrated that depletion of XBP1 resulted in downregulation of HIF1α targets VEGFA, PDK1, GLUT1 and DDIT4 expression (FIG. 6C, Figure S4). This result indicates that XBP1 regulates the expression of HIF1α targets under hypoxic conditions. Performing the same experiment in another TNBC cell line, HS578T, yielded similar results (FIG. 6D FIG. 6H). Thus, XBP1 is an essential mediator of the hypoxic response via its key function in regulating the expression of HIF1α target genes.

To further understand the mechanism by which XBP1 regulates HIF1α transcriptional pathways, we first examined the correlation between XBP1 and HIF1α at genome-wide level. As shown in FIG. 6E, a high level of XBP1 occupancy was associated with increased occurrence of the HIF1α motif in TNBC (p<1×10-5), suggesting a requirement of XBP1 for HIF1α occupancy. Next, we depleted XBP1 and examined the occupancy of HIF1α at HIF1α-XBP1 co-bound sites near well-established HIF1α targets. MDA-MB-231 cells infected with control shRNA or XBP1 shRNA were treated for 24 h under hypoxic conditions, and the extracts were subjected to ChIP. As expected, XBP1 knockdown reduced the occupancy of XBP1 on co-bound sites (FIG. 6I). HIF1α levels were not altered by XBP1 depletion (FIG. 6J). XBP1 depletion substantially attenuated HIF1α occupancy at the targets FIG. 6F), suggesting that the recruitment of HIF1α is dependent on XBP1

To further understand the relationship between XBP1, HIF1α and the basal transcription machinery, we examined the recruitment of RNA polymerase II at the protnoters of HIF1α target genes. In particular, we carried out ChIP against RNA polymerase IL Consistent with the redaction in HIF1α target transcripts after XBP1 depletion, the binding of RNA polymerase II to the XBP1-HIF1α co-bound sites was also significantly reduced in the absence of XBP1 (FIG. 6G). As a control, RNA polymerase II binding to β-actin, which is not occupied by XBP1, was not altered (FIG. 6G). Collectively, these data suggest that XBP1 regulates HIF1α transcriptional activity by controlling the binding of HIF1α to its targets and by the recruitment of RNA polymerase IT.

Example 8: XBP1Activation is Associated with Human Breast Cancer Prognosis

Figure 7A:
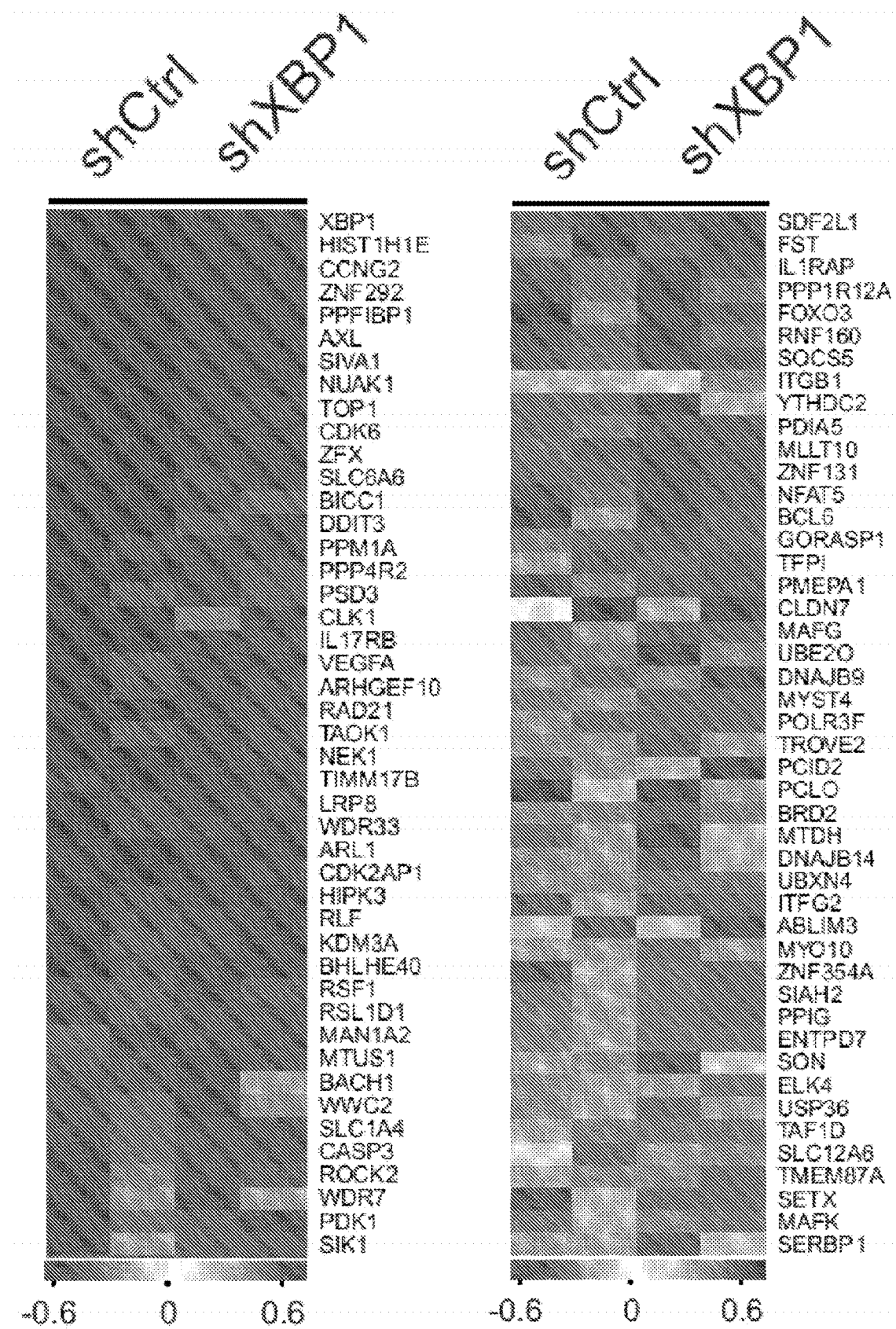

Through integrated analysis of XBP1 ChIP-sect data and gene expression profiles, we identified a plurality of genes that are directly bound and up-regulated by XBP1. This gene set was defined as the XBP1 signature (FIG. 7A). The gene signature is also defines by the genes set forth in Table 1.

TABLE 1

XBP1 gene signature

| Refseq | Gene Symbol | RP value | FDR |
|---|---|---|---|
| NM_005080 | XBP1 | 0.000308166 | 0.046 |
| NM_001079539 | XBP1 | 0.000616333 | 0.033 |
| NM_173354 | SIK1 | 0.007660895 | 0.026 |
| NM_001177 | ARL1 | 0.007856733 | 0.0225 |
| NM_015021 | ZNF292 | 0.010608268 | 0.0192 |
| NM_001113182 | BRD2 | 0.018319709 | 0.017 |
| NM_005104 | BRD2 | 0.020101806 | 0.016444444 |
| NM_024116 | TAF1D | 0.021276877 | 0.014727273 |
| NM_005321 | HIST1H1E | 0.026452097 | 0.013733333 |
| NM_134470 | IL1RAP | 0.026969403 | 0.01425 |
| NM_177444 | PPFIBP1 | 0.031355838 | 0.014380952 |

TABLE 1-continued

XBP1 gene signature

| Refseq | Gene Symbol | RP value | FDR |
|---|---|---|---|
| NM_144949 | SOCS5 | 0.031921637 | 0.014818182 |
| NM_014011 | SOCS5 | 0.032025593 | 0.014956522 |
| NM_014840 | NUAK1 | 0.032058195 | 0.015166667 |
| NM_003410 | ZFX | 0.032864181 | 0.015851852 |
| NM_012421 | RLF | 0.035372081 | 0.017483871 |
| NM_002610 | PDK1 | 0.036732609 | 0.018571429 |
| NM_001259 | CDK6 | 0.037469791 | 0.018666667 |
| NM_001134368 | SLC6A6 | 0.037723647 | 0.018918919 |
| NM_003670 | BHLHE40 | 0.038232511 | 0.018894737 |
| NM_006265 | RAD21 | 0.039985705 | 0.0195 |
| NM_012330 | MYST4 | 0.041773318 | 0.020095238 |
| NM_004792 | PPIG | 0.041827844 | 0.020232558 |
| NM_006699 | MAN1A2 | 0.042287349 | 0.020347826 |
| NM_006427 | SIVA1 | 0.043459113 | 0.020857143 |
| NM_001145306 | CDK6 | 0.046056189 | 0.022346154 |
| NM_021709 | SIVA1 | 0.046086078 | 0.022566038 |
| NR_027856 | CLK1 | 0.047788652 | 0.023758621 |
| NR_027855 | CLK1 | 0.048191354 | 0.024305085 |
| NM_004071 | CLK1 | 0.048592674 | 0.024833333 |
| NM_001162407 | CLK1 | 0.04931818 | 0.025419355 |
| NM_001135581 | SLC1A4 | 0.050712807 | 0.026338462 |
| NM_003286 | TOP1 | 0.051189956 | 0.026848485 |
| NM_018463 | ITFG2 | 0.05599817 | 0.028027778 |
| NM_020791 | TAOK1 | 0.056306819 | 0.028273973 |
| NM_004642 | CDK2AP1 | 0.058411965 | 0.028973684 |
| NM_004354 | CCNG2 | 0.059493678 | 0.029777778 |
| NM_006810 | PDIA5 | 0.059980932 | 0.030292683 |
| NM_003038 | SLC1A4 | 0.060388037 | 0.030952381 |
| NM_033026 | PCLO | 0.060740842 | 0.031035294 |
| NM_001031723 | DNAJB14 | 0.063887884 | 0.032593407 |
| NM_022044 | SDF2L1 | 0.068126387 | 0.034 |
| NM_012328 | DNAJB9 | 0.06931484 | 0.034632653 |
| NM_018386 | PCID2 | 0.070132067 | 0.035030303 |
| NM_001127203 | PCID2 | 0.07045563 | 0.03532 |
| NM_052834 | WDR7 | 0.07101882 | 0.035960784 |
| NM_015285 | WDR7 | 0.071327044 | 0.036368932 |
| NM_003432 | ZNF131 | 0.072904644 | 0.037364486 |
| NM_018725 | IL17RB | 0.073397321 | 0.038558559 |
| NM_014629 | ARHGEF10 | 0.076846594 | 0.040537815 |
| NM_005834 | TIMM17B | 0.078254854 | 0.041289256 |
| NM_001127202 | PCID2 | 0.078373692 | 0.04157377 |
| NM_178812 | MTDH | 0.078864716 | 0.042080645 |
| NM_015565 | RNF160 | 0.079551116 | 0.042384 |
| NM_173214 | NFAT5 | 0.079829972 | 0.042692913 |
| NM_138714 | NFAT5 | 0.080330418 | 0.043410853 |
| NM_138713 | NFAT5 | 0.080828942 | 0.044333333 |
| NM_020182 | PMEPA1 | 0.080955732 | 0.044820896 |
| NM_006599 | NFAT5 | 0.081325577 | 0.045066667 |
| NM_001113178 | NFAT5 | 0.081820358 | 0.046246377 |
| NM_001307 | CLDN7 | 0.08389827 | 0.046628571 |
| NM_206866 | BACH1 | 0.085201186 | 0.046822695 |
| NM_001006622 | WDR33 | 0.085351526 | 0.047070423 |
| NM_021913 | AXL | 0.085668045 | 0.047496503 |
| NM_001080512 | BICC1 | 0.086429554 | 0.047708333 |
| NM_014607 | UBXN4 | 0.086642454 | 0.048246575 |
| NM_001699 | AXL | 0.086705455 | 0.048489796 |
| NM_001186 | BACH1 | 0.087932789 | 0.050313725 |
| NM_001706 | BCL6 | 0.089419251 | 0.051261146 |
| NM_001042370 | TROVE2 | 0.089715599 | 0.051594937 |
| NM_005734 | HIPK3 | 0.09027961 | 0.0521875 |
| NM_001048200 | HIPK3 | 0.091696467 | 0.054060606 |
| NM_004641 | MLLT10 | 0.095742597 | 0.057737143 |
| NM_020354 | ENTPD7 | 0.096224921 | 0.058034091 |
| NM_001009569 | MLLT10 | 0.097206843 | 0.058905028 |
| NM_004600 | TROVE2 | 0.097239566 | 0.059233333 |
| NM_001042369 | TROVE2 | 0.097349374 | 0.059436464 |
| NM_015659 | RSL1D1 | 0.097841743 | 0.059747253 |
| NM_032991 | CASP3 | 0.098056014 | 0.060174863 |
| NM_004346 | CASP3 | 0.098873885 | 0.0605 |
| NM_002360 | MAFK | 0.100285797 | 0.061659574 |
| NM_013409 | FST | 0.100786927 | 0.061978836 |
| NM_033300 | LRP8 | 0.102030543 | 0.062492147 |
| NM_003376 | VEGFA | 0.102146358 | 0.06307772 |
| NM_022066 | UBE2O | 0.103051603 | 0.063897959 |
| NM_017522 | LRP8 | 0.103179158 | 0.064304569 |
| NM_004083 | DDIT3 | 0.104217214 | 0.06504 |
| NM_004631 | LRP8 | 0.104316037 | 0.065792079 |
| NM_001001925 | MTUS1 | 0.105039098 | 0.066868293 |
| NM_199170 | PMEPA1 | 0.105246837 | 0.06763285 |
| NM_032711 | MAFG | 0.10539111 | 0.068210526 |
| NM_001018054 | LRP8 | 0.105441559 | 0.068580952 |
| NM_199169 | PMEPA1 | 0.105647608 | 0.069549296 |
| NM_001001924 | MTUS1 | 0.106466031 | 0.070608295 |
| NM_033668 | ITGB1 | 0.107856482 | 0.071909502 |
| NM_001025368 | VEGFA | 0.108110645 | 0.072198198 |
| NM_001025367 | VEGFA | 0.109049116 | 0.07275 |
| NM_005067 | SIAH2 | 0.109127465 | 0.072915556 |
| NM_199171 | PMEPA1 | 0.109425982 | 0.073274336 |
| NM_001025366 | VEGFA | 0.109980443 | 0.073929825 |
| NM_006287 | TFPI | 0.112000579 | 0.07525 |
| NM_018433 | KDM3A | 0.112719 | 0.075476395 |
| NM_001455 | FOXO3 | 0.113000887 | 0.075794872 |
| NM_001146688 | KDM3A | 0.113091614 | 0.076153191 |
| NM_025090 | USP36 | 0.113105469 | 0.076559322 |
| NM_012224 | NEK1 | 0.113246019 | 0.077268908 |
| NM_002359 | MAFG | 0.113434126 | 0.077548117 |
| NM_001033756 | VEGFA | 0.114262021 | 0.078248963 |
| NM_201559 | FOXO3 | 0.115000173 | 0.079853659 |
| NM_004850 | ROCK2 | 0.11677596 | 0.08116 |
| NM_177951 | PPM1A | 0.117567808 | 0.081698413 |
| NM_015640 | SERBP1 | 0.117780863 | 0.082086957 |
| NM_001018069 | SERBP1 | 0.118092488 | 0.082433071 |
| NM_001018068 | SERBP1 | 0.118404096 | 0.083276265 |
| NM_001018067 | SERBP1 | 0.118715685 | 0.08355814 |
| NM_015497 | TMEM87A | 0.118930277 | 0.084030769 |
| NM_001025369 | VEGFA | 0.119400069 | 0.084557252 |
| NM_001973 | ELK4 | 0.120484396 | 0.085222642 |
| NM_022828 | YTHDC2 | 0.121842701 | 0.087516484 |
| NM_016578 | RSF1 | 0.121898417 | 0.087744526 |
| NM_206909 | PSD3 | 0.122170784 | 0.08792 |
| NM_006466 | POLR3F | 0.123368602 | 0.088527076 |
| NM_012334 | MYO10 | 0.123689567 | 0.088834532 |
| NM_014945 | ABLIM3 | 0.123956467 | 0.089039427 |
| NM_015046 | SETX | 0.127055781 | 0.091531469 |
| NM_174907 | PPP4R2 | 0.127746035 | 0.092090278 |
| NM_006350 | FST | 0.128346778 | 0.092914089 |
| NM_005135 | SLC12A6 | 0.128533103 | 0.093130137 |
| NM_005649 | ZNF354A | 0.128561915 | 0.093372414 |
| NM_024949 | WWC2 | 0.129706945 | 0.09427027 |
| NM_031899 | GORASP1 | 0.130596765 | 0.095006711 |
| NM_138927 | SON | 0.132138364 | 0.097980456 |
| NM_001143886 | PPP1R12A | 0.133036549 | 0.099647436 |

In exemplary embodiments, subset of the genes listed in Table 1 can be selected to constitute a more simple gene signature. For example, a subset of genes, e.g., 10-20, 20-30 or more genes from Table 1 (or, for example, 5%, 10%, 15% 20% or more of the genes in Table 1) can be selected having a high degree of expression or representation in the gene signature. Alternatively, a subset of genes, e.g., 10-20, 20-30 or more genes from Table 1 (or, for example, 5%, 10%, 15% 20% or more of the genes in Table 1) can be selected having a low degree of expression or representation in the gene signature.

Differentially expressed genes (DEGs) can be selected based on low false discovery rate (FDR) (e.g., FDR for p-values from t-test.) For example, genes with a RP value of <0.1, <0.09, <0.08, <0.07, <0.06, <0.05, <0.04 or <0.02 can be selected as DEGs. Alternatively, genes with a FDR <0.05, <0.04, <0.1 or <0.2 can be selected as DEGs. Alternatively, or in combination, DEGs can be selected based on rank product (RP) value A lower absolute value for RP indicates a higher degree of differential expression. The genes in Table 1 were ranked in descending order of the absolute RP value.

RP ranking can characterize up-regulated genes and down-regulated genes under one class. To obtain one RP value per gene for comparison within results (or for comparison with ranking according to other methods), a lower value can be defined as a net value for a gene. A small net value for RP is therefore evidence of differential expression. (See e.g., Kadota K et al. (2009). *Algorithm Mol Biol.* 4:7.)

To investigate the correlation of the XBP1 gene signature with patient relapse-free survival, we performed survival analysis using an aggregate breast cancer dataset that contains the gene expression profile and the survival information for 109 TNBC patient samples from 21 datasets (Lehmann, B. D., et al. 2011. *J Clin Invest* 121, 2750-2767) Of the plurality of genes in the XBP1 signature, a subset of genes were represented on the TNBC microarray datasets (FIG. 7A, Table 1).

Figure 7B:
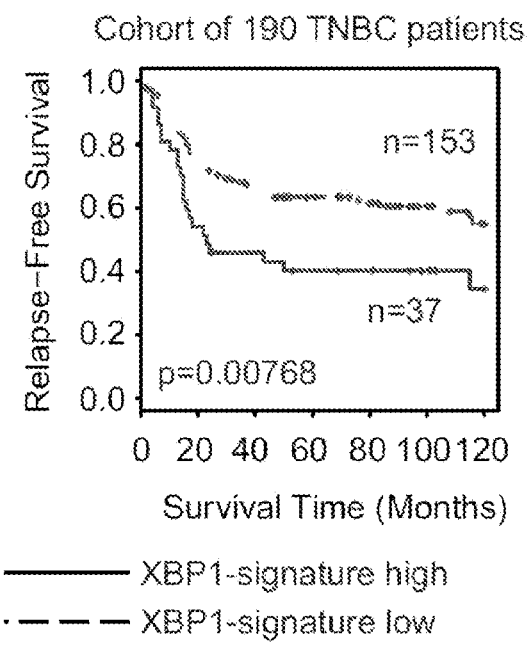
Figure 7C:
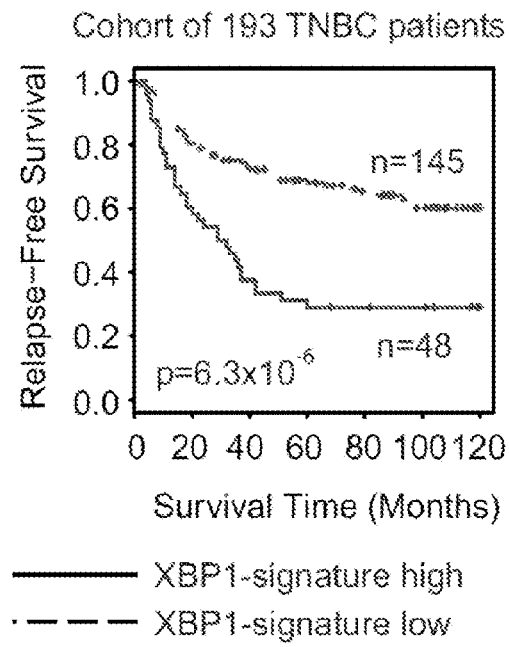

As shown in FIG. 7B, the activation of the XBP1 pathway, as represented by the higher expression of the XBP1 signature, correlates with shorter relapse-free survival (Log-rank test, p=0.00768). These findings were confirmed in an independent validation cohort of 193 TNBC patients (FIG. 7C. Log-rank test, $p=6.3 \times 10^{-6}$).

Figure 7D:
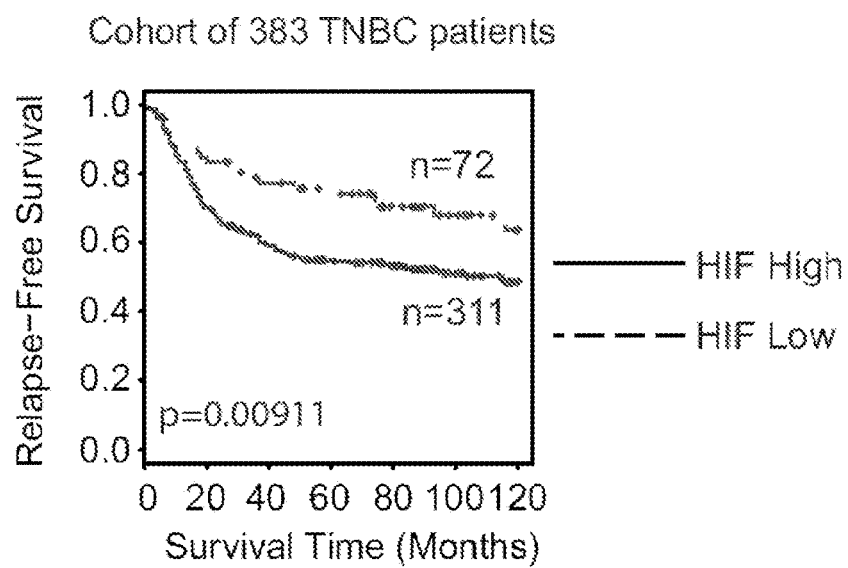

We have identified both the UPR and the hypoxia response as XBP1 dependent pathways in TNBC. Interestingly, growing evidence indicates that increased expression of HIF1α and HIF1α targets, such as CA9 and GLUT1, are associated with worse clinical outcome in basal-like human breast tumors (Bos, R., et al. 2003. *Cancer* 97, 1573-1581; Hussein. Y. R., et al. 2011. *Transl Oncol* 4, 321-327; Semenza, G. L., 2010. *Oncogene* 29, 625-634; Tan, E. Y., et al. 2009. *Br J Cancer* 100, 405-411), consistent with the association of XBP1 with TNBC. To understand the clinical relevance of these two XBP1-regulated pathways in TNBC. we examined mRNA expression levels of multiple UPR markers in TICs and NTICs derived from five human TNBC patients. This analysis (survival analysis) revealed up-regulation of these marker genes in TICs relative to NTICs, indicative of an association of the UPR pathway with TICs and TNBC. Intriguingly, we also found that an elevated expression of the UPR gene signature in TNBC was associated with decreased relapse free survival (Log-rank test. p=0.00911) (FIG. 7D).

Collectively these data demonstrate that activation of XBP1 in TNBC patients is associated with poor clinical outcome.

Discussion

Patients with TNBC have a relatively poorer prognosis and are more likely to recur and develop metastatic disease than other breast cancer subtypes (Foulkes, W. D., et al. 2010. *N Engl J Med* 363, 1938-48; Lehmann, B. D., et al. 2011. *J Clin Invest* 121, 2750-67). The genes linked to TNBC are not well understood and thus, unlike other breast cancer subtypes, effective targeted therapies have not yet been identified for TNBC (Foulkes, W. D., et al. 2010. *N Engl J Med* 363, 193848). Here, by manipulating the expression of XBP1, the key component of the most evolutionarily conserved branch of the UPR, in a panel of breast cancer cell lines and in the patient-derived xenograft model, a key function for XBP1 in TNBC was discovered. XBP1 was activated in TNBC cells, and silencing of XBP1 was very effective in suppressing the tumorigenicity and progression of TNBCs. In addition to its essential role in TNBC, it is expected that XBP1 may also affect other subtypes of human breast cancer. TNBC typically contains a higher proportion of tumor-initiating cells (TICs) (Blick, T., et al. 2010. *J Mammary Gland Bial Neoplasia* 15, 235-52; Ricardo, S., et al. 2011. *J Clin Pathol* 64, 937-46). Relative to NTICs, TICs are resistant to chemotherapy, and contribute to a significantly higher incidence of recurrence and distant metastasis (Smalley, M., et al 2003. *Nat Rev Cancer* 3, 832-44; Stingl, J., et al. 2007. *Nat Rev Cancer* 7, 791-9). Progress in targeting this subpopulation with novel therapeutics continues to be hampered by our incomplete knowledge of the molecular pathways contributing to TIC identity. It is thus demonstrated herein that XBP1 is a novel regulator for breast TICs.

These studies are the first to demonstrate that compromising the ER stress response significantly impairs the TIC population. It is speculated that TICs residing in the stem cell niche require robust UPR activation to cope with external stress. Hence TICs rely on XBP1 activation and their function is compromised in its absence. The increased activation of XBP1 in TICs is intriguing and provides potentially novel strategies to target this subpopulation of cancer cells. Hypoxia is known to promote aggressive tumor phenotypes and HIF1α was recently demonstrated to be essential for TNBC and breast TICs (Schwab, L. P., et al. 2012, *Breast Cancer Res* 14, R6; Conley, S. J., et al. 2012. *Proc Natl Acid Sci USA* 109, 2784-9; Montagner, M., et al. 2012. *Nature* 487, 380-4). Increased HIF1α levels are also associated with increased metastasis and decreased survival in patients with TNBC (Semenza, G. L., 2010. *Oncogene* 29, 625-34; Bos, R., et al. 2003. *Cancer* 97, 1573-81). The data presented herein reveal that XBP1 in TNBC through regulating the HIF1α transcriptional program. HIF1α requires XBP1 to sustain downstream target expression. Hypoxia is a physiological inducer of the UPR in cancer (Wouters, B. G., et al. 2008. *Nat Rev Cancer* 8, 851-64). In the studies, it was found that XBP1 functions in a positive feedback loop to sustain the hypoxia response via regulating HIF1α transcriptional activity. This feed-forward circuit ensures maximum HIF activity and an efficient adaptive response to the cytotoxic, microenvironment of solid tumors. HIF activity is tightly controlled during tumor progression, through translational and post-translational regulation of HIF1α, but relatively less is known about how HIF1α transcriptional activity is controlled (Kaelin, W. G., Jr., et al. 2008. *Mol Cell* 30, 393-402). These studies reveal a novel function for XBP1 as a HIF1α transcriptional cofactor. Herein is proposed a model in which these two critical pathways, the UPR and the hypoxia response, are physically interconnected and act together to mount an appropriate adaptive response to perpetuate cancer cells in the hostile tumor microenvironment. These data highlight the importance of XBP1 in TN BC progression and recurrence. Activation of the XBP1 pathway is correlated with poor patient survival in human TNBC patients, hence inhibition of this pathway may offer novel treatment strategies for this aggressive subtype of breast cancer. The use of UPR inhibitors in combination with standard chemotherapy may greatly enhance the effectiveness of anti-tumor therapies.

Experimental Procedures

Detailed protocols for all experimental procedures are provided below.

Cell Culture and Treatments

The non transformed breast cell line MCF10A cells contains ER-Src, an integrated fusion of the v-Src oncoprotein, and the ligand-binding domain of estrogen receptor (ER) (Iliopoulos, D., et al., 2009, *Cell* 139, 693-706). These cells were grown in DMEM/F12 medium supplemented with 5% donor horse serum (Invitrogen), 20 ng/ml epidermal growth factor (EGF) (R&D systems), 10 ug/ml insulin (Sigma), 100 ug/ml hydrocortisone (Sigma), 100 ng/ml cholera toxin (Sigma), 50 units/ml pen/step (Gibco), with the addition of puromycin (Sigma). Src induction and cellular transformation was achieved by treatment with 1 uM 4-OH tamoxifen (TAM), typically for 36 h as described previously (Iliopoulos, D., et al. 2009. *Cell* 139, 693-706; Iliopoulos, D., et al. 2010. *Mol Cell* 39, 761-72).

All breast cancer cells were cultured according to Neve, R. M., et al. 2006. *Cancer Cell* 10, 515-27. Following retroviral or lentiviral infection, cells were maintained in the presence of puromycin (2 ug/ml) (Sigma). For all hypoxia experiments, cells were maintained in an anaerobic chamber (Coy laboratory) with 0.1% $O_2$. For glucose deprivation experiments, cells were maintained in DMEM without glucose medium (Gibco) with 10% FBS (Gibco) and 50 units/nl of penicillin/streptomycin.

Orthotopic Tumor Growth Assays

Six week old female NOD/SCID/IL2Rγ-/- mice (Taconic) were used for xenograft studies. Approximately $1.5 \times 10^6$ viable tumor cells were resuspended in 40 ul growth factor reduced Matrigel (BD Biosciences) and injected orthotopically into mammary gland four as previously described (Zhang, Q., et al. 2009. *Cancer Cell* 16, 413-424). Mice were supplied with chow containing 6 g doxycycline/kg (Bioserv) for treatment. For bioluminescent detection and quantification of cancer cells. mice were given a single i.p. injection of a mixture of luciferin (50 mg/kg), ketamine (150 mg/kg), and xylazine (12 mg/kg) in sterile water. Five minutes later, mice were placed in a light tight chamber equipped with a charge coupled device IVIS imaging camera (Xenogen). Photons were collected for a period of 1-60 s, and images were obtained by using LIVING IMAGE 2.60.1 software (Xenogen) and quantified using IGOR Pro 4.09A image analysis software (WaveMatrics). The imaging intensity was normalized to the luminescence signal of each individual mouse taken before the Doxycycline chow treatment. The average luminescence ratio of treatment group (LacZ or XBP1 shRNA) was plotted over the course of doxycycline chow treatment. Results are presented as mean±standard error of the mean (SEM).

Sorting of TICs and NTICs (General)

To separate TICs from NTICs, flow cytometric cell sorting was performed on single-cell suspensions that were stained with CD44 antibody (FITC-conjugated) and with CD24 antibody (PE-conjugated) (BD Biosciences) for 30 min. As used throughout, TICs are defined by the minority $CD44^{high}/CD24^{low}$ population, whereas NTICs are defined by the majority $CD44^{low}/CD24^{high}$.

Purification of TICs and NTICs from Patients with TNBC (Detailed)

Five human invasive triple negative ductal carcinoma tissues (stage III) were used in our TIC experiments (Iliopoulos, D., et al. 2011. *Pro Natl Acad Sci USA* 108, 1397-402), Immunomagnetic purification of TICs and NTICs was performed according to Shipitsin, M., et al. 2007. *Cancer Cell* 11, 259-73. Briefly, the breast tissues were minced into small pieces (1 mm) using a sterile razor blade. The tissues were digested with 2 mg/ml collagenase I (C0130, Sigma) and 2 mg/ml hyaluronidase (1-13506. Sigma) in 370 C for 3 h. Cells were filtered, washed with PBS and followed by Percoll gradient centrifugation. The first purification step was to remove the immune cells by immunomagnetic purification using an equal mix of CD45 (leukocytes), CD15 (granulocytes), CD14 (monocytes) and CD19 (B cells) Dynabeads (Invitrogen). The second purification step was to isolate fibroblasts from the cell population by using CD10 beads for magnetic purification. The third step was to isolate the endothelial cells by using an "endothelial cocktail" of beads (CD3) BD Pharmingen cat no. 555444, CD146 P1H12 MCAM BD Pharmingen cat no. 550314, CD105 Abeam cat no. Ab2529, Cadherin 5 Immunotech cat no. 1597, and CD34 BD Pharmingen cat no. 555820). In the final step the CD44high cells were purified from the remaining cell population using CD44 beads.

These cells were sorted for CD44high/CD24low (TIC) cells, CD24high cells were also purified using CD24 beads. These cells were sorted for CD44low/CD24high (NTICs) cells. These TIC and NTIC populations were sorted again with CD44 antibody (FITC-conjugated) (555478, BD Biosciences) and CD24 antibody (PE-conjugated) (555428, BD Biosciences) in order to increase their purity (>99.2% in all cases).

Mammosphere Formation Assay

Mammospheres were generated by placing cell lines in suspension (1,000 cells/ml) in serum-free DMEM/F12 media, supplemented with B27 (1:50, Invitrogen), 0.4% BSA, 20 ng/mL EGF, and 4 µg/ml insulin. After 6 days of incubation, mammospheres were typically >75 mM in size with 97% bearing the $CD44^{high}/CD24^{low}$ phenotype. For serial passaging, 6-day old mammospheres were harvested using a 70 urn cell strainer, whereupon they were dissociated to single cells with trypsin and then re-grown in suspension for 6 days.

ChIP and ChIP-seq

ChIP assays were carried out as described previously (Chen, X., et al. 2008. *Cell* 133, 1106-1117). Briefly, cells were crosslinked with 1% formaldehyde for 10 min at room temperature, and formaldehyde was then inactivated by the addition of 125 mM glycine. Chromatin extracts containing DNA fragments with an average size of 500 bp were immunoprecipitated by using the antibodies described below. All ChIP experiments were repeated at least three times.

ChIP was performed with XBP1 antibody (Biolegend, 619502); HIF1α antibody (Abeam, ab2185), RNA Polymerase II antibody (Millipore, 05-623) or GST antibody (Santa Cruz, sc-33613). The primers used in FIG. 6 are listed in Table 2.

Supplementary Table 2
ChIP primer sequence

| Gene | Forward |
| --- | --- |
| JMJD1A 1 | TGTTGCTTCAGGTTCAATAGAATTTTTCCC (SEQ ID NO: 1) |
| JMJD1A 2 | CATCATTCATTATGGCCTTCAACTACTTTA (SEQ ID NO: 2) |
| JMJD1A 3 | CTTTCCTGTGAGATTCTTCCGCCA (SEQ ID NO: 3) |
| JMJD1A 4 | GGGTCCGGGAGGTCTGTGCGTGTCTTGTGAG (SEQ ID NO: 4) |
| JMJD1A 5 | TCGCACACCGACGTTACCAAGAAGGATCTG (SEQ ID NO: 5) |
| JMJD2C 1 | AAGTTCAAGGGGAATCTATGTATTGTTCAT (SEQ ID NO: 6) |
| JMJD2C 2 | TCCCGTTAGCCTTAGCTCAATTAATCACAT (SEQ ID NO: 7) |
| JMJD2C 3 | TCCTTCTACGCGAGTATCTTTCCC (SEQ ID NO: 8) |
| JMJD2C 4 | GATTATCGCTTGCTTTCTTACCTTGCTGGC (SEQ ID NO: 9) |

-continued

Supplementary Table 2
ChIP primer sequence

| | | |
|---|---|---|
| VEGFA | TCTTCGAGAGTGAGGAGGTGTGT (SEQ ID NO: 10) | |
| PDK1 | CGCCCTGTCCTTGAGCC (SEQ ID NO: 11) | |
| DDIT4 | CTAGAGCTCGCGGTCTGGTCTGGTCT (SEQ ID NO: 12) | |
| NDRG1 | AAGACGTGAGCTAAGCTGTCCGA (SEQ ID NO: 13) | |
| BETA-ACTIN | GGGACTATTTGGGGGTGTCT (SEQ ID NO: 14) | |
| Control | TGAGGGTTCATCAAGGTGGTCTCT (SEQ ID NO: 15) | |
| JMJD1A 1 | Reverse | Reference |
| JMJD1A 2 | TGGCCTATCCTAAGGTGACGCTATGA (SEQ ID NO: 16) | |
| JMJD1A 3 | GAAGAAAGGCGTGGATTACTGGATA (SEQ ID NO: 17) | Xia et al., 2009 |
| JMJD1A 4 | CCGCGAAATCGGTTATCAACTTTGGG (SEQ ID NO: 18) | |
| JMJD1A 5 | CGGCGCTTTCACCTTTCTCTCCCTCT (SEQ ID NO: 19) | |
| JMJD2C 1 | ACTCGGCTCTATACAACCATTCCAAA (SEQ ID NO: 20) | |
| JMJD2C 2 | CTACTAGAAAATCAACTGGACTCATGGCAC (SEQ ID NO: 21) | |
| JMJD2C 3 | CTGGGICCCTTGTGGCGTTTTCTCTA (SEQ ID NO: 22) | Xia et al., 2009 |
| JMJD2C 4 | GTCACGTGGGCTTACAAACAGCTT (SEQ ID NO: 23) | |
| VEGFA | ACTGTATTACCAAGTTTGCGGGATACTGTA (SEQ ID NO: 24) | Lee et al., 2009 |
| PDK1 | AAGGCGGAGAGCCGGAC (SEQ ID NO: 25) | Lee et al., 2009 |
| DDIT4 | CGGTATGGAGCGTCCCCT (SEQ ID NO: 26) | |
| NDRG1 | GGCGAAGAGGAGGTGGACGACGACGAG (SEQ ID NO: 27) | Xia et al., 2009 |
| BETA-ACTIN | ATGGAGGCAGAAGGAACATGTGAG (SEQ ID NO: 28) | Gromak et al., 2006 |
| Control | TCCCATAGGTGAAGGCAAAG (SEQ ID NO: 29) | Xia at al., 2009 |

The ChIP-seq library was prepared using ChIP-Seq DNA Sample Prep Kit (Illumina) according to the manufacturer's instructions. XBP1 ChIP-seq peaks were identified using MACS package (Zhang, Y., et al. 2008. *Genome Biol* 9, 8137) with a p-value cutoff of $1\times10^{-7}$, Tumor Initiation Assay Using Patient-Derived Tumors Tumorgraft line BCM-2147 was derived by transplantation of a fresh patient breast tumor biopsy (ER-PR-HER2-) into the cleared mammary gland fat pad of immune-compromised SCID/Beige mice and retained the patient biomarker status and morphology across multiple transplant generations in mice. To overcome the challenge of limited cell viability by dissociation of solid tumors. 10 mg tumor pieces containing $1.3\times10^5$ cells were transplanted with basal membrane extract (Trevigen, Gaithersburg, MD). The cell number was calculated as average cell yield $1.3\times10^7$ cells/gram$\times0.01$ gram=$1.3\times10^5$ cells. For sustained siRNA release in the first two weeks following transplantation, porous silicon particles loaded with siRNA (scrambled control or XBP 1 siRNA) packaged in nanoliposomes were injected into the tumor tissue with basal membrane extract at the time of transplantation. Scrambled sequence [5' CGAAGUGUGUGUGUGUGGCdTdT 3'; SEQ ID NO:30]: XBP 1 siRNA sequence [5' CACCCUGAAUUCAUUGU-CUdTdT 3'; SEQ ID NO:31]. Two weeks post-transplantation, nanoliposomes containing siRNA (15 mg per mouse) were injected I.V. twice weekly for 8 weeks. Mice were monitored thrice weekly for tumor development, and tumors were calipered and recorded using LABCAT Tumor Analysis and Tracking System v6.4 (Innovative Programming Associates, Inc., Princeton, NJ). Tumor incidence is reported 10 weeks post-transplantation.

Invasion Assay

We performed invasion assays according to 49. Invasion of the matrigel was conducted by using standardized conditions with BD BioCoat growth factor reduced MATRIGEL invasion chambers (PharMingen). Assays were conducted according to manufacturer's protocol, by using 5% horse serum (GIBCO) and 20 ng/ml EGF (R&D Systems) as chemoattractants.

Colony Formation Assay $1\times105$ breast cancer cells were mixed 4:1 (v/v) with 2.0% agarose in growth medium for a final concentration of 0.4% agarose. The cell mixture was plated on top of a solidified layer of 0.8% agarose in growth medium. Cells were fed every 6 to 7 days with growth medium containing 0.4% agarose. The number of colonies was counted after 20 days. The experiment was repeated three times and the statistical significance was calculated using Student's t test.

Subcutaneous Xenograft Experiments

MCF10A ER-Src TAM-treated (36 h) cells or MDA-MB-436 or HBL-100 breast cancer cells were injected subcutaneously in the right flank of athymic nude mice (Charles River Laboratories). Tumor growth was monitored every five days and tumor volumes were calculated by the equation $V(mm^3)=a\times b^2/2$, where a is the largest diameter and b is the perpendicular diameter. When the tumors reached a size of ~100 $mm^3$ (15 days) mice were randomly distributed into 3 groups (5 mice/group), The first group was used as control (non-treated), the second group was intratumorally treated with shCtrl and the third group was intratumorally treated with shXBP1. For each injection 10 ug of shRNA was mixed with 2 ul of vivo-jetPEI (polyethylenimine) reagent (cat. no 201-50G, PolyPlus Transfection SA) in a final volume of 100 ul. These treatments were repeated every five days for 4 cycles (days 15, 20, 25, 30). In addition, in vivo dilution xenotransplantation assays were performed in NOD/SCID/IL2Rγ-/- mice. Mice were evaluated on a weekly basis for tumor formation. All mice were maintained in accordance with Dana-Farber Cancer Institute Animal Care and Use Committee procedures and guidelines.

Gene Expression Microarray Analysis

MDA-MB-231 cells infected with control shRNA or XBP1 shRNA lentiviruses grown in glucose free medium were treated in 0.1% $O_2$ in a hypoxia chamber for 24 h. Total RNA was extracted by using RNeasy mini kit with on column DNase digestion (QIAGEN). Biotin labeled cRNA was prepared from 1 ug of total RNA, fragmented, and hybridized to Affymetrix human U133 plus 2.0 expression array. All Gene expression microarray data were normalized and summarized using RMA (Irizarry, R. A., et al. 2003. *Nucleic Acids Res* 31, e15). The differentially expressed genes were identified using Limina (Smyth, G. K., et al. 2003. *Methods Mol Biol* 224, 111-36) (q≤10%, fold change ≥1.5).

Motif Analysis

Flanking sequences around the summits (±300 bp) of the top 1,000 XBP1 binding sites were extracted and the repetitive regions in these flanking sequences were masked. The consensus sequence motifs were derived using Seqpos(Lupien, M., et al. 2008. *Cell* 132, 958-70).

XBP1 Signature Generation

The XBP1 signature was generated by integrative analysis of ChIP-seq and differential expression data using the method as previously described (Tang. Q., et al. 2011. *Cancer Res* 71, 6940-7). Briefly, we first calculated the regulatory potential for a given gene, Sg, as the sum of the nearby binding sites weighted by the distance from each site to the TSS of the gene;

$$S_g = \Sigma_{i=1}^{k} e^{-(0.5+4\Delta_i)}$$

where k is the number of binding sites within 100 kb of gene g and Δi is the distance between site i and the TSS of gene g normalized to 100 kb (e.g., 0.5 for a 50 kb distance). We then applied the Breitling's rank product method (Breitling, R., et al. 2004. *FEBS Lett* 573, 83-92; Klisch, T. J., et al. 2011. *Proc Natl Acad Sci USA* 108, 3288-93) to combine regulatory potentials with differential expression t-values to rank all genes based on the probability that they were XBP1 targets. Only genes with at least one binding site within 100 kb from its TSS and a differential expression t-value above the 75th percentile were considered (Tang, Q, et al. 2011. *Cancer Res* 71, 6940-7). The FDR of XBP1 target prediction was estimated by permutation (Breitling, R., et al. 2004. *FEBS Lett* 573, 83-92). At a FDR cutoff of 10% and differential expression fold-change cutoff of 1.5, we obtained 119 up-regulated genes (HUGO gene symbol) as direct targets of XBP1.

Survival Analysis (General)

Principle component analysis (PCA) was applied to patient expression profiles of genes of interest and separated the samples into 2 groups based on the median value of the first component. Kaplan-Meier survival analysis was used to assess the significance of survival difference. In cases where XBP1 signature genes were the relevant gene set, a correlation value was calculated between the relevant gene expression indexes of each patient and those of the MDA-MB-231 cell line, and the correlations of the 2 groups were compared and the significance of difference was assessed. by t-test.

Survival Analysis (Detailed)

We performed survival analysis using an aggregated compendium of gene expression profiles of 383 TNBC samples from 21 breast cancer datasets (Rody, A., et al. 2011. *Breast Cancer Res* 13, R97). Of the 119 XBP1 signature genes, 91 genes had corresponding probes in this dataset. To avoid potential confounding factors such as heterogeneity among the samples, we randomly split all 383 TNBC samples into two datasets with similar size (190 and 193 cases) and evaluated the correlation of the XBP1 gene signature with relapse free survival using these two datasets respectively. We separated patients into two subgroups: one with higher and the other with lower expression of XBP1 signature. The subgroup classification was performed as described previously (Matotta, L. L., et al. 2011. *J Clin Invest* 121, 2723-35). Patients were considered to have higher XBP1 signature if they had average expression values of all the genes in the XBP1 signature above the 60th percentile (Marotta, L. L., et al. 2011. *J Clin Invest* 121, 2723-35). Kaplan-Meier survival analysis was performed and log-rank test was used to assess the statistical significance of survival difference between these 2 groups. A similar analysis was performed for the HIF pathway signature (VEGFA. PDK1, DDIT4, SLC2A1, KDM3A, NDRG1, PFKFB3, PIK3CA, RORB, CREBBP, PIK3CB and EGLN1).

Virus Production and Infection.

The Phoenix packaging cell line was used for the generation of ecotropic retroviruses and all retroviral infections were carried out as described previously (Martinon, F., et al., 2010. *Nat Immunol* 11, 411-8). The 293T packaging cell line was used for lentiviral amplification and all lentiviral infections were carried out as previously described (Martinon, F., et al. ., 2010. *Nat Immunol* 11, 411-8). In brief, viruses were collected 48 and 72 hr after transfection, filtered, and used for infecting cells in the presence of 8 mg/ml polybrene prior to drug selection with puromycin (2 µg/ml). shRNA constructs were generated by The Broad Institute. Targeting of GFP mRNA with shRNA served as a control. Optimal targeting sequences identified for human XBP1 were 5'-GACCCAGTCATGTTCTTCAAA-3' SEQ ID NO:32). and 5'-GAACAGCNAGIGGTAGATITA-3' (SEQ ID NO:33), respectively. Knockdown efficiency was assessed by real-time PCR for XBP 1.

Luciferase Assay

For FIG. 5H, MDA-MB-231 cells were co-transfected with 3×HRE luciferase (3×HRE-Luc) plasmid (Yan, Q., et al. 2007; *Mol Cell Biol* 27, 2092-102) and XBP1s overexpression construct (Kaser, A. et al. 2008. *Cell* 134, 743-56) or control vector by using Lipofectamine 2000 (Invitrogen). A *Renilla* luciferase plasmid (pRL-CMV from Promega) was co-transfected as an internal control. Cells were harvested 36 hr after transfection, and the luciferase activities of the cell lysates were measured by using the Dual-luciferase Reporter Assay System (Promega). For FIG. 5L MDA-MB-231 cells were co-transfected with 3×HRE-Luc and two inducible XBP1 shRNA construct (in pLKO-Tet-On vector) or control shRNA construct by using Lipofectamine 2000 (Invitrogen). Cells were treated with doxycycline for 48 h and hypoxia for 24 h before the luciferase activities of the cell lysates were measured.

Statistical Analysis

The significance of differences between treatment groups were identified with a Student's t-test. P values of less than 0.05 were considered statistically significant.

Coimmunoprecipitation

Transfected cells were lysed in cell lysis buffer (50 mM Tris HCl, pH 8.0, 150 mM NaCl, 1 mM EDTA, 1% Nonidet P-40, and 10% glycerol with protease inhibitor cocktail) for 1 hour. M2 beads (Sigma) were incubated with the whole cell extracts at 4° C. for overnight. The beads were washed with cell lysis buffer four times. Finally, the beads were boiled in 2× sample buffer for 10 minutes. The eluents were analyzed by Western blot. Nuclear extracts were used to perform the endogenous co-IP as described previously (Xu, J., a al. 2010. *Genes Dev* 24, 783-98). Briefly, 5 mg of nuclear extracts were incubated with 5 ug of anti-HIF1α antibody (Novus Biologicals, NB100-479) at 4° C. for overnight. The protein complexes were precipitated by addition of protein A agarose beads (Roche) with incubation for 4 hr at 4° C. The beads were washed four times and boiled for 5 min in 2× sample buffer.

Real-Time PCR Analysis

1ug of RNA sample was reverse-transcribed to form cDNA, which was subjected to SYBR Green based real-time PCR analysis. Primers used for β-actin forward:5'-CCTG- TACGCCCAACACAGTGC-3' (SEQ ID NO:34) and reverse 5'-ATACTCCTGCTIGCTGATCC-3' (SEQ ID NO:35); for VEGFA forward 5'-CACACAGGATGGCTT-GAAGA-3' (SEQ ID NO:36) and reverse 5'-AGGGCA-GAATCATCACGAAG-3' (SEQ ID NO:37); for PDK1 forward 5'-GGAGGTCTCAACACGAGGIC-3' (SEQ ID NO:38) and reverse 5'-GTICATGICACGCTGGGTAA-3' (SEQ ID NO:39); for GLUT1 forward 5'-TGGACCCAT-GTCTGGTTGTA-3' (SEQ ID NO:40) and reverse 5'-ATG-GAGCCCAGCAGCAA-3' (SEQ ID NO:41); for JMJD1A forward 5'-TCGGTGACTTTCGTTCAGC-3' (SEQ ID NO:51) and reverse 5'-CACCGACGTTACCAAGAAGG-3' (SEQ ID NO:42); for DDIT4 forward 5'-CATCAGGTTG-GCACACAAGT-3' (SEQ ID NO:43) and reverse 5'-CCTG-GAGAGCTCGGACTG-3' (SEQ ID NO:44); for MCT4 forward 5'-CCTGGAGAGCTCGGACTG-3' (SEQ ID NO:45) and reverse 5'-CTGCAGTTCGAGGTGCTCAT-3' (SEQ ID NO:46); for XBP1 splicing forward 5'-CCTGGT-TGCTGAAGAGGAGG-3'(SEQ ID NO:47) and reverse 5'-CCATGGGGAGATGTICTGGAG-3' (SEQ ID NO:48); for XBP1 total forward 5'-AGGAGTTAAGACAGCGCT-TGGGGATGGAT-3' (SEQ ID NO:49) and reverse 5'-CT-GAATCTGAAGAGTCAATACCGCCAGAAT-3' (SEQ ID NO:50).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

This invention is further illustrated by the following examples which should not be construed as limiting.

EQUIVALENTS

Those skilled in the art will recognize. or be able to ascertain using no more than routine experimentation, many equivalents to the specific embodiments of the invention described herein. Such equivalents are intended to be encompassed by the following claims.

---

The invention claimed is:

1. A method for treating triple negative breast cancer (TNBC) in a subject, the method comprising administering to the subject a direct inhibitor of X-box binding protein 1 (XBP1) and doxorubicin each in an amount effective to inhibit growth of cancer cells in said subject, such that TNBC in the subject is treated;

wherein the direct inhibitor of XBP1 is an XBP1 shRNA.

2. The method of claim 1, wherein the direct inhibitor of XBP1 is administered to breast tissue of said subject.

3. The method of claim 2, wherein the direct inhibitor of XBP1 is administered directly to the breast tissue of the subject.

4. The method of claim 1, wherein the treatment promotes longer relapse-free survival of the subject.

5. The method of claim 1, wherein the treating comprises reducing the population of chemotherapy-resistant tumor initiating breast cancer cells in the subject.

6. The method of claim 1, wherein the comprises depleting breast tumor initiating breast cancer cells in the subject.

* * * * *

UNITED STATES PATENT AND TRADEMARK OFFICE
CERTIFICATE OF CORRECTION

Page 1 of 2

PATENT NO. : 10,655,130 B2
APPLICATION NO. : 15/441103
DATED : May 19, 2020
INVENTOR(S) : Glimcher et al.

It is certified that error appears in the above-identified patent and that said Letters Patent is hereby corrected as shown below:

On the Title Page

On page 6, in Column 2, under "Other Publications", Line 2, delete "Allografl" and insert --Allograft-- therefor On page 6, in Column 2, under "Other Publications", Line 2, delete "Rais" and insert --Rats-- therefor On page 6, in Column 2, under "Other Publications", Line 43, delete "Allografl" and insert --Allograft-- therefor On page 6, in Column 2, under "Other Publications", Line 69, delete "inftuenza" and insert --influenza-- therefor On page 7, in Column 1, under "Other Publications", Line 19, delete "Nonrnal" and insert --Normal-- therefor On page 7, in Column 1, under "Other Publications", Line 48, delete "apolipoprolein B100" and insert --apolipoprotein Blood-- therefor On page 7, in Column 2, under "Other Publications", Line 8, delete "actor" and insert --factor-- therefor On page 8, in Column 2, under "Other Publications", Line 36, delete "Nith" and insert --With-- therefor On page 8, in Column 2, under "Other Publications", Line 21, delete "Allografl" and insert --Allograft--

On page 9, in Column 2, under "Other Publications", Line 2, delete "actor" and insert --factor-- therefor Signed and Sealed this
Twenty-fourth Day of November, 2020

Andrei Iancu
*Director of the United States Patent and Trademark Office*

CERTIFICATE OF CORRECTION (continued)
U.S. Pat. No. 10,655,130 B2

On page 9, in Column 2, under "Other Publications", Line 8, delete "cis-Acling" and insert --cis-Acting-- therefor In the Claims In Column 58, Line 24, in Claim 6, after "the", insert --treating--

SEQUENCE LISTING

<160> NUMBER OF SEQ ID NOS: 51

<210> SEQ ID NO 1
<211> LENGTH: 30
<212> TYPE: DNA
<213> ORGANISM: Artificial Sequence
<220> FEATURE:
<223> OTHER INFORMATION: A synthetic oligonucleotide primer

<400> SEQUENCE: 1
tgttccttca ggttcaatag aatttttccc          30

<210> SEQ ID NO 2
<211> LENGTH: 30
<212> TYPE: DNA
<213> ORGANISM: Artificial Sequence
<220> FEATURE:
<223> OTHER INFORMATION: A synthetic oligonucleotide primer

<400> SEQUENCE: 2
catcattcat tatggccttc aactacttta          30

<210> SEQ ID NO 3
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 3
ctttcctgtg agattcttcc gcca          24

<210> SEQ ID NO 4
<211> LENGTH: 30
<212> TYPE: DNA
<213> ORGANISM: Artificial Sequence
<220> FEATURE:
<223> OTHER INFORMATION: A synthetic oligonucleotide primer

<400> SEQUENCE: 4
gggtccggga ggctgtgcgt gtcttgtgag          30

<210> SEQ ID NO 5
<211> LENGTH: 30
<212> TYPE: DNA
<213> ORGANISM: Artificial Sequence
<220> FEATURE:
<223> OTHER INFORMATION: A synthetic oligonucleotide primer

<400> SEQUENCE: 5
tcccacaccg acgttaccaa gaaggatctg                                    30

<210> SEQ ID NO 6
<211> LENGTH: 30
<212> TYPE: DNA
<213> ORGANISM: Artificial Sequence
<220> FEATURE:
<223> OTHER INFORMATION: A synthetic oligonucleotide primer

<400> SEQUENCE: 6
aacttcaagg ggaatctatg tattgttcat                                    30

<210> SEQ ID NO 7
<211> LENGTH: 30
<212> TYPE: DNA
<213> ORGANISM: Artificial Sequence
<220> FEATURE:
<223> OTHER INFORMATION: A synthetic oligonucleotide primer

<400> SEQUENCE: 7
tcccgttagc cttagctcaa ttaatcacat                                    30

<210> SEQ ID NO 8
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 8
tccttctacg cgagtatctt tccc                                          24

<210> SEQ ID NO 9
<211> LENGTH: 30
<212> TYPE: DNA
<213> ORGANISM: Artificial Sequence
<220> FEATURE:
<223> OTHER INFORMATION: A synthetic oligonucleotide primer

<400> SEQUENCE: 9
gattatcgct tgctttctta ccttgctggc                                    30

<210> SEQ ID NO 10
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 10
tcttcgagag tgaggacgtg tgt                                           23

<210> SEQ ID NO 11
<211> LENGTH: 17
<212> TYPE: DNA
<213> ORGANISM: Artificial Sequence
<220> FEATURE:

```
<223> OTHER INFORMATION: A synthetic oligonucleotide primer

<400> SEQUENCE: 11
cgccctgtcc ttgagcc                                                  17

<210> SEQ ID NO 12
<211> LENGTH: 26
<212> TYPE: DNA
<213> ORGANISM: Artificial Sequence
<220> FEATURE:
<223> OTHER INFORMATION: A synthetic oligonucleotide primer

<400> SEQUENCE: 12
ctagagctcg cggtctggtc tggtct                                        26

<210> SEQ ID NO 13
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 13
aacacgtgag ctaagctgtc cga                                           23

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 14
gggactattt gggggtgtct                                               20

<210> SEQ ID NO 15
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 15
tgagggttca tcaagctggt gtct                                          24

<210> SEQ ID NO 16
<211> LENGTH: 26
<212> TYPE: DNA
<213> ORGANISM: Artificial Sequence
<220> FEATURE:
<223> OTHER INFORMATION: A synthetic oligonucleotide primer

<400> SEQUENCE: 16
tggcctatcc taaggtgacg ctatga                                        26

<210> SEQ ID NO 17
<211> LENGTH: 26
<212> TYPE: DNA
<213> ORGANISM: Artificial Sequence
<220> FEATURE:
<223> OTHER INFORMATION: A synthetic oligonucleotide primer

<400> SEQUENCE: 17
gaagaaaggc gtggagttac tggata                                        26
```

-continued

<210> SEQ ID NO 18
<211> LENGTH: 26
<212> TYPE: DNA
<213> ORGANISM: Artificial Sequence
<220> FEATURE:
<223> OTHER INFORMATION: A synthetic oligonucleotide primer

<400> SEQUENCE: 18
ccgcgaaatc ggttatcaac tttggg                                26

<210> SEQ ID NO 19
<211> LENGTH: 27
<212> TYPE: DNA
<213> ORGANISM: Artificial Sequence
<220> FEATURE:
<223> OTHER INFORMATION: A synthetic oligonucleotide primer

<400> SEQUENCE: 19
cggcgctttc acctttctct cccctct                               27

<210> SEQ ID NO 20
<211> LENGTH: 26
<212> TYPE: DNA
<213> ORGANISM: Artificial Sequence
<220> FEATURE:
<223> OTHER INFORMATION: A synthetic oligonucleotide primer

<400> SEQUENCE: 20
actcggctct atacaaccat tccaaa                                26

<210> SEQ ID NO 21
<211> LENGTH: 30
<212> TYPE: DNA
<213> ORGANISM: Artificial Sequence
<220> FEATURE:
<223> OTHER INFORMATION: A synthetic oligonucleotide primer

<400> SEQUENCE: 21
ctactagaaa atcaactgga ctcatggcac                            30

<210> SEQ ID NO 22
<211> LENGTH: 26
<212> TYPE: DNA
<213> ORGANISM: Artificial Sequence
<220> FEATURE:
<223> OTHER INFORMATION: A synthetic oligonucleotide primer

<400> SEQUENCE: 22
ctgggtccct tgtggcgttt tctcta                                26

<210> SEQ ID NO 23
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 23
gtcacgtggg cttacaaaca gctt                                  24

<210> SEQ ID NO 24
<211> LENGTH: 30
<212> TYPE: DNA
<213> ORGANISM: Artificial Sequence
<220> FEATURE:
<223> OTHER INFORMATION: A synthetic oligonucleotide primer

```
<400> SEQUENCE: 24
actgtattac caagtttgcg ggatactgta                                      30

<210> SEQ ID NO 25
<211> LENGTH: 17
<212> TYPE: DNA
<213> ORGANISM: Artificial Sequence
<220> FEATURE:
<223> OTHER INFORMATION: A synthetic oligonucleotide primer

<400> SEQUENCE: 25
aaggcggaga gccggac                                                    17

<210> SEQ ID NO 26
<211> LENGTH: 18
<212> TYPE: DNA
<213> ORGANISM: Artificial Sequence
<220> FEATURE:
<223> OTHER INFORMATION: A synthetic oligonucleotide primer

<400> SEQUENCE: 26
cggtatggag cgtcccct                                                   18

<210> SEQ ID NO 27
<211> LENGTH: 27
<212> TYPE: DNA
<213> ORGANISM: Artificial Sequence
<220> FEATURE:
<223> OTHER INFORMATION: A synthetic oligonucleotide primer

<400> SEQUENCE: 27
ggcgaagagg aggtggacga cgacgag                                         27

<210> SEQ ID NO 28
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 28
atggaggcag aaggaacatg tgag                                            24

<210> SEQ ID NO 29
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 29
tcccataggt gaaggcaaag                                                 20

<210> SEQ ID NO 30
<211> LENGTH: 21
<212> TYPE: RNA
<213> ORGANISM: Artificial Sequence
<220> FEATURE:
<223> OTHER INFORMATION: A synthetic RNA sequence
<221> NAME/KEY: misc_feature
<222> LOCATION: 20,21
<223> OTHER INFORMATION: n = dT

<400> SEQUENCE: 30
cgaagugugu guguguggcn n                                               21
```

<210> SEQ ID NO 31
<211> LENGTH: 21
<212> TYPE: RNA
<213> ORGANISM: Artificial Sequence
<220> FEATURE:
<223> OTHER INFORMATION: A synthetic RNA sequence
<221> NAME/KEY: misc_feature
<222> LOCATION: 20,21
<223> OTHER INFORMATION: n = dT

<400> SEQUENCE: 31
cacccugaau ucauugucun n                                              21

<210> SEQ ID NO 32
<211> LENGTH: 21
<212> TYPE: DNA
<213> ORGANISM: Homo sapiens

<400> SEQUENCE: 32
gacccagtca tgttcttcaa a                                              21

<210> SEQ ID NO 33
<211> LENGTH: 21
<212> TYPE: DNA
<213> ORGANISM: Homo sapiens

<400> SEQUENCE: 33
gaacagcaag tggtagattt a                                              21

<210> SEQ ID NO 34
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 34
cctgtacgcc aacacagtgc                                                20

<210> SEQ ID NO 35
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 35
atactcctgc ttgctgatcc                                                20

<210> SEQ ID NO 36
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 36
cacacaggat ggcttgaaga                                                20

<210> SEQ ID NO 37
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 37
agggcagaat catcacgaag                                                  20

<210> SEQ ID NO 38
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 38
ggaggtctca acacgaggtc                                                  20

<210> SEQ ID NO 39
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 39
gttcatgtca cgctgggtaa                                                  20

<210> SEQ ID NO 40
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 40
tggacccatg tctggttgta                                                  20

<210> SEQ ID NO 41
<211> LENGTH: 17
<212> TYPE: DNA
<213> ORGANISM: Artificial Sequence
<220> FEATURE:
<223> OTHER INFORMATION: A synthetic oligonucleotide primer

<400> SEQUENCE: 41
atggagccca gcagcaa                                                     17

<210> SEQ ID NO 42
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 42
caccgacgtt accaagaagg                                                  20

<210> SEQ ID NO 43
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 43
catcaggttg gcacacaagt                                                  20

<210> SEQ ID NO 44
<211> LENGTH: 18

```
<212> TYPE: DNA
<213> ORGANISM: Artificial Sequence
<220> FEATURE:
<223> OTHER INFORMATION: A synthetic oligonucleotide primer

<400> SEQUENCE: 44
cctggagagc tcggactg                                                 18

<210> SEQ ID NO 45
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 45
tacatgtaga cgtgggtcgc                                               20

<210> SEQ ID NO 46
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 46
ctgcagttcg aggtgctcat                                               20

<210> SEQ ID NO 47
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 47
cctggttgct gaagaggagg                                               20

<210> SEQ ID NO 48
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 48
ccatggggag atgttctgga g                                             21

<210> SEQ ID NO 49
<211> LENGTH: 29
<212> TYPE: DNA
<213> ORGANISM: Artificial Sequence
<220> FEATURE:
<223> OTHER INFORMATION: A synthetic oligonucleotide primer

<400> SEQUENCE: 49
aggagttaag acagcgcttg gggatggat                                     29

<210> SEQ ID NO 50
<211> LENGTH: 30
<212> TYPE: DNA
<213> ORGANISM: Artificial Sequence
<220> FEATURE:
<223> OTHER INFORMATION: A synthetic oligonucleotide primer

<400> SEQUENCE: 50
```

```
ctgaatctga agagtcaata ccgccagaat                                         30

<210> SEQ ID NO 51
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 51
tcaggtgact ttcgttcagc                                                    20
```